US012195470B2

(12) United States Patent
Frei et al.

(10) Patent No.: US 12,195,470 B2
(45) Date of Patent: Jan. 14, 2025

(54) 7-PHENOXY-N-(3-AZABICYCLO[3.2.1]-OCTAN-8-YL-6,7-DIHYDRO-5H-PYRROLO-[1,2-B][1,2,4]TRIAZOL-2-AMINE DERIVATIVES AND RELATED COMPOUNDS AS GAMMA- SECRETASE MODULATORS FOR THE TREATMENT OF ALZHEIMER'S DISEASE

(71) Applicant: Hoffmann-La Roche Inc., Little Falls, NJ (US)

(72) Inventors: Beat Frei, Basel (CH); Hasane Ratni, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 771 days.

(21) Appl. No.: 17/413,413

(22) PCT Filed: Dec. 11, 2019

(86) PCT No.: PCT/EP2019/084538
§ 371 (c)(1),
(2) Date: Jun. 11, 2021

(87) PCT Pub. No.: WO2020/120521
PCT Pub. Date: Jun. 18, 2020

(65) Prior Publication Data
US 2022/0056036 A1 Feb. 24, 2022

(30) Foreign Application Priority Data

Dec. 13, 2018 (EP) .................................... 18212199

(51) Int. Cl.
*C07D 487/04* (2006.01)
*C07D 471/04* (2006.01)
*A61K 31/46* (2006.01)
*A61P 25/28* (2006.01)
*A61P 27/16* (2006.01)

(52) U.S. Cl.
CPC ......... *C07D 487/04* (2013.01); *C07D 471/04* (2013.01)

(58) Field of Classification Search
CPC ..... C07D 487/04; C07D 471/04; A61P 25/28; A61P 27/16; A61K 31/46
See application file for complete search history.

(56) References Cited

U.S. PATENT DOCUMENTS

| 7,875,611 | B2 | 1/2011 | Bain et al. |
| 8,252,935 | B2 | 8/2012 | Ho et al. |
| 8,486,967 | B2 | 7/2013 | Baumann et al. |
| 8,673,900 | B2 | 3/2014 | Zhu et al. |
| 8,703,753 | B2 | 4/2014 | Sredni et al. |
| 8,703,763 | B2 | 4/2014 | Baumann et al. |
| 8,754,100 | B2 | 6/2014 | Kitazawa et al. |
| 8,891,284 | B2 | 11/2014 | Williams et al. |
| 9,115,143 | B2 | 8/2015 | Minne et al. |
| 9,637,491 | B2 | 5/2017 | Almstetter et al. |
| 10,562,903 | B2 | 2/2020 | Bartels et al. |
| 10,941,147 | B2* | 3/2021 | Bartels ..................... A61P 25/28 |
| 2005/0020481 | A1 | 1/2005 | Bain et al. |
| 2005/0119315 | A1 | 6/2005 | Fedida et al. |
| 2007/0047181 | A1 | 1/2007 | Bain et al. |
| 2007/0190156 | A1 | 8/2007 | Beatch et al. |
| 2008/0070911 | A1 | 3/2008 | Bain et al. |
| 2010/0029639 | A1 | 2/2010 | Bain et al. |
| 2011/0190269 | A1 | 8/2011 | Baumann et al. |
| 2011/0207730 | A1 | 8/2011 | Bain et al. |
| 2018/0237432 | A1 | 8/2018 | Baumann et al. |

FOREIGN PATENT DOCUMENTS

| CN | 103403003 A | 11/2013 |
| CN | 107922437   | 4/2018 |
| CN | 108137579 A | 6/2018 |

(Continued)

OTHER PUBLICATIONS

Chowdhury EA, Understanding the brain uptake and permeability of small molecules through the BBB: A technical overview. J Cereb Blood Flow Metab. Aug. 2021;41(8): 1797-1820. doi: 10.1177/0271678X20985946. Epub Jan. 1, 20214. PMID: 33444097; PMCID: PMC8327119. (Year: 2021).*
Steeg PS, Camphausen KA, Smith QR. Brain metastases as preventive and therapeutic targets. Nat Rev Cancer. May 2011;11(5): 352-63. doi: 10.1038/nrc3053. Epub Apr. 7, 2011. PMID: 21472002; PMCID: PMC7351203. (Year: 2011).*
Belikov, V.G. "Pharmaceutical Chemistry," Tutorial, 4th, revised and expanded edition, Moscow, MEDPress-Inform, 2007, pp. 27-29 (including English Translation).
"International Preliminary Report on Patentability—PCT/EP2019/073303" (Report Issuance Date: Mar. 9, 2021, Chapter I),:pp. 1-8 (Mar. 18, 2021).
"International Search Report—PCT/EP2019/073303" (w/Written Opinion),:pp. 1-12 (Oct. 7, 2019).
Guidance on preclinical studies of drugs, 2012, 1-24.
(Continued)

*Primary Examiner* — Bruck Kifle
*Assistant Examiner* — Kevin S Martin
(74) *Attorney, Agent, or Firm* — Vasily Ignatenko

(57) ABSTRACT

The invention provides 7-phenoxy-N-(3-azabicyclo[3.2.1] octan-8-yl)-6,7-dihydro-5H-pyrrolo[1,2-b][1,2,4]triazol-2-amine derivatives and related compounds of the general formula (I) wherein $R^1$, Ar, n and m are as described herein, compositions including the compounds, processes of manufacturing the compounds and the compounds for use in methods of medical treatment. The present compounds are as gamma-secretase modulators for the treatment of diseases associated with the deposition of β-amyloid in the brain, such as Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica and Down syndrome. The present description discloses the preparation of exemplary compounds as well as pharmacological data thereof (e.g. pages 54 to 74; examples 1 to 64; table). An exemplary compound is e.g. (R)-7-(3,5-difluorophenoxy)-N-((1R,5S,8s)-3-(6-methoxypyridazin-4-yl)-3-azabicyclo [3.2.1]octan-8-yl)-6,7-dihydro-5H-pyrrolo[1,2-b][1,2,4]triazol-2-amine (example 1).

47 Claims, No Drawings

(56) References Cited

FOREIGN PATENT DOCUMENTS

| WO | 1999/21560 | | 5/1999 |
|---|---|---|---|
| WO | 2000/47547 | A2 | 8/2000 |
| WO | 00/71528 | A1 | 11/2000 |
| WO | 2001/32170 | A1 | 5/2001 |
| WO | 2008/138753 | | 11/2008 |
| WO | 2010/138901 | A1 | 12/2010 |
| WO | 2011/092272 | A1 | 8/2011 |
| WO | 2011/101304 | A2 | 8/2011 |
| WO | 2012/116965 | A1 | 9/2012 |
| WO | 2014/060112 | A1 | 4/2014 |
| WO | 2017/042114 | A1 | 3/2017 |
| WO | 2018/001918 | A1 | 1/2018 |
| WO | 2018/060300 | A1 | 4/2018 |
| WO | 2018/083050 | A1 | 5/2018 |
| WO | 2018/087018 | A1 | 5/2018 |
| WO | 2018/111926 | A2 | 6/2018 |
| WO | 2019/141832 | A1 | 7/2019 |

OTHER PUBLICATIONS

Ulrika Yngve et al., "Triazolopyrimidinones as g-secretase modulators: structure-activity relationship, modulator profile, and in vivo profiling" MedChemComm 4(2):422 (Jan. 1, 2013).

Akhapkina, V. et al., "Fundamental Principles of the Modulatory Concept and Classification of Modulatory Drugs (English translation)" (English Abstract),: 933-951 ( 2012).

Bastin, R. et al., "Salt Selection and Optimisation Procedures for Pharmaceutical New Chemical Entities" Organic Process Research & Development 4(5):427-435 ( 2000).

Dyson, G. et al., "Chemistry of Synthetic Drugs", 12-19 ( 1964) (English Abstract).

"International Search Report—PCT/EP2019/084538" (w/Written Opinion),:pp. 1-13 (Mar. 5, 2020).

"International Preliminary Report on Patentability—PCT/EP2019/084538" (Report Issuance Date: Jun. 8, 2021; Chapter I),:pp. 1-8 (Jun. 24, 2021).

Kummerer, K., "Pharmaceuticals in the Environment" Ann Rev Environ Res 35:57-75 (Nov. 1, 2010).

* cited by examiner

7-PHENOXY-N-(3-AZABICYCLO[3.2.1-]OCTAN-8-YL-6,7-DIHYDRO-5H-PYRROLO[-1,2-B][1,2,4]TRIAZOL-2-AMINE DERIVATIVES AND RELATED COMPOUNDS AS GAMMA- SECRETASE MODULATORS FOR THE TREATMENT OF ALZHEIMER'S DISEASE

FIELD OF THE INVENTION

The present invention relates to bicyclic heteroaryl compounds useful as gamma-secretase modulators, their manufacture, pharmaceutical compositions comprising said compounds and their use as medicaments for the therapeutic and/or prophylactic treatment of diseases associated with the deposition of β-amyloid in the brain, such as Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica and Down syndrome.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain lengths, e.g. Aβ38, Aβ40 and Aβ42. The latter one is regarded to be the more pathogenic amyloid peptide because of its strong tendency to form neurotoxic aggregates. β-Secretase is a typical aspartyl protease.

γ-Secretase is a high molecular weight complex that consists of four essential subunits: presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, *Nature*, 525 (2015), 212-217). The presenilins are bearing the catalytic site and represent a group of atypical aspartyl proteases which cleave their substrates within the TM and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e. ablation of the presenilin genes, and by low-molecular weight inhibitory compounds. According to the amyloid cascade hypothesis for AD the production and deposition of Aβ is the ultimate cause for the disease. Therefore, it is believed that selective and potent inhibition of γ-secretase might be useful for the prevention and treatment of AD.

An alternative mode of treatment is the modulation of the γ-secretase activity which results in a selective reduction of the Aβ42 production. This would lead to an increase of shorter Aβ isoforms, such as Aβ38, A1337 or others, which have no or reduced capability for aggregation and plaque formation, and are not or less neurotoxic. Compounds modulating γ-secretase activity include certain non-steroidal anti-inflammatory drugs (NSAIDs) and related analogues (Weggen et al., *Nature*, 414 (2001) 212-216).

Numerous documents describe the current knowledge on γ-secretase modulation, such as the following publications: Morihara et al., *J. Neurochem.*, 83 (2002), 1009-12; Jantzen et al., *J. Neuroscience*, 22 (2002), 226-54; Takahashi et al., *J. Biol. Chem.*, 278 (2003), 18644-70; Beher et al., *J. Biol. Chem.*, 279 (2004), 43419-26; Lleo et al., *Nature Med.*, 10 (2004), 1065-6; Kukar et al., Nature Med., 11 (2005), 545-50; Perretto et al., J. Med. Chem., 48 (2005), 5705-20; Clarke et al., *J. Biol. Chem.*, 281 (2006) 31279-89; Stock et al., *Bioorg. Med. Chem. Lett.*, 16 (2006) 2219-2223; Narlawar et al., *J. Med. Chem.*, 49 (2006) 7588-91; Ebke et al., *J. Biol. Chem.*, 286 (2011) 37181-86; Oehlich, Gijsen et al., *J. Med. Chem.*, 54 (2011), 669-698; Li et al., *Biochemistry*, 52 (2013), 3197-3216; Hall et al., *Progress in Med. Chem.*, 53 (2014) 101-145; Bursavich et al., *J. Med. Chem.*, 59 (2016); WO 2018/111926.

Therefore, modulating the γ-secretase activity is a promising therapeutic strategy for the treatment or prevention of diseases associated with the deposition of β-amyloid in the brain, such as Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica and Down syndrome.

There is a need for new compounds, formulations, treatments and therapies to treat diseases and disorders associated with the deposition of β-amyloid in the brain. It is, therefore, an object of this invention to provide compounds useful for the treatment or prevention or amelioration of such diseases and disorders with improved therapeutic properties.

SUMMARY OF THE INVENTION

A first object of the present invention is a compound of formula (I)

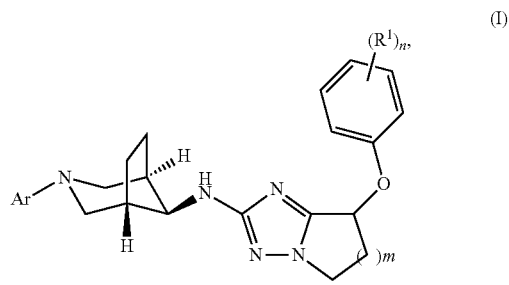

wherein
R¹ is halogen, lower alkyl, lower alkyl substituted by halogen, lower alkoxy, or lower alkoxy substituted by halogen,
and R¹ may be different if n=2 or 3;
m is 1, 2 or 3;
n is 1, 2 or 3;
Ar is a six membered heteroaryl group, selected from

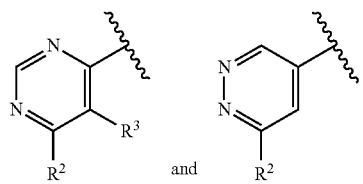

wherein
R² is hydrogen, halogen, lower alkyl, lower alkyl substituted by halogen, or lower alkoxy;
R³ is hydrogen or halogen;
or a pharmaceutically acceptable salt thereof.

A further object of the invention is a process for the preparation of a compound of formula (I) as described herein, or a pharmaceutically acceptable salt thereof, comprising reacting a compound 7

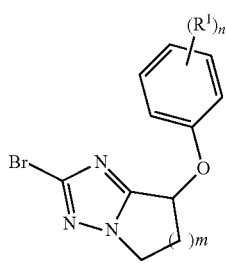

with an amine 8

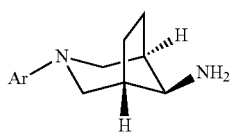

wherein Ar, R¹, n and m are as defined above,
to form said compound of formula (I), and if desired, converting the compounds obtained into a pharmaceutically acceptable salt thereof.

A further object of the present invention is a compound of formula (I) as described herein, or a pharmaceutically acceptable salt thereof, when manufactured according to the process as described above.

A further object of the present invention is a compound of formula (I) as described herein, or a pharmaceutically acceptable salt thereof, for use as therapeutically active substance.

A further object of the present invention is a pharmaceutical composition comprising a compound of formula (I) as described herein, or a pharmaceutically acceptable salt thereof, and a pharmaceutically acceptable excipient.

A further object of the present invention is a compound of formula (I) as described herein, or a pharmaceutically acceptable salt thereof, for use in the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome.

A further object of the present invention is the use of a compound of formula (I) as described herein, or a pharmaceutically acceptable salt thereof, for the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome.

A further object of the present invention is the use of a compound of formula (I) as described herein, or a pharmaceutically acceptable salt thereof, for the preparation of a medicament for the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome.

A further object of the present invention is a method for the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome, which method comprises administering an effective amount of a compound of formula (I) as described herein, or a pharmaceutically acceptable salt thereof.

DETAILED DESCRIPTION OF THE INVENTION

The following definitions of the general terms used in the present description apply irrespectively of whether the terms in question appear alone or in combination with other groups.

The term "lower alkyl", alone or in combination with other groups, refers to saturated straight- or branched-chain alkyl group, with single or multiple branching, wherein the alkyl group in general comprises 1 to 7 carbon atoms ("$C_{1-7}$-alkyl"), for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular lower alkyl groups have 1 to 4 carbon atoms ("$C_{1-4}$-alkyl").

The term "lower alkyl substituted by halogen" denotes an alkyl group as defined above, wherein at least one hydrogen atom is replaced by halogen, preferably fluorine, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$ and the like. The preferred group is $CF_3$.

The term "alkoxy", alone or in combination, denotes a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy and tert-butyloxy.

The term "lower alkoxy substituted by halogen" denotes a lower alkoxy group as defined above, wherein at least one hydrogen atom is replaced by halogen, preferably fluorine.

The terms "halogen" or "halo", alone or in combination, denotes fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein.

Particularly preferred pharmaceutically acceptable salts of compounds of formula (I) are the salts of hydrochloric acid, hydrobromic acid, sulfuric acid, phosphoric acid and methanesulfonic acid.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The terms "asymmetric carbon atom" and "asymmetric center" mean a carbon atom with four different substituents. According to the Cahn-Ingold-Prelog Convention, an asymmetric carbon atom can be of the "R" or "S" configuration.

The following abbreviations are used in the present text:
Boc=tert-butyloxycarbonyl, CAS RN=chemical abstracts registration number, DIAD=diisopropyl azodicarboxylate, DMF=dimethylformamide, EtOAc=ethyl acetate, EtOH=ethanol, FCS=fetal calf serum, GCMS=gas chromatography mass spectrometry, h=hour(s), Hal=halogen, Hept=heptane, HPLC=high-performance liquid chromatography, IMDM=Iscove's modified Dulbecco's medium, LCMS=liquid chromatography mass spectrometry, MeCN=acetonitrile, MeOH=methanol, Me$_2$SO=dimethylsulfoxide (DMSO), MOM=methoxymethyl, min=minute(s), ml=milliliter, μl=microliter, MS=mass spectrum, NaOMe=sodium methoxide, NaOtBu=sodium tert-butyloxide, nBuLi=n-butyllithium, NEt$_3$=triethylamine (TEA), NMP=N-methyl-2-pyrrolidone, OAc=Acetoxy, Pd$_2$(dba)$_3$=tris(dibenzylideneacetone)dipalladium(0), p-TsOH=p-toluenesulfonic acid, R=any group, RT=room temperature, SFC=supercritical fluid chromatography, tBuXPhos=2-di-tert-butylphosphino-2',4',6'-triisopropylbiphenyl, TBME=tert-butylmethylether, TEA=triethylamine, TFA=trifluroacetic acid, THF=tetrahydrofuran, THP=tetrahydropyran.

Compounds of the Invention

In a first aspect, the present invention provides a compound of formula (I)

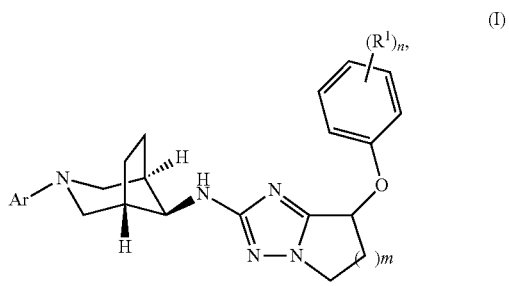

wherein
$R^1$ is halogen, lower alkyl, lower alkyl substituted by halogen, lower alkoxy, or lower alkoxy substituted by halogen,
and $R^1$ may be different if n=2 or 3;
m is 1, 2 or 3;
n is 1, 2 or 3;
Ar is a six membered heteroaryl group, selected from

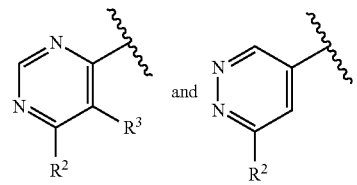

wherein
$R^2$ is hydrogen, halogen, lower alkyl, lower alkyl substituted by halogen, or lower alkoxy;
$R^3$ is hydrogen or halogen;
or a pharmaceutically acceptable salt thereof.

In one embodiment, there is provided a compound of formula (I) as described herein, wherein the compound of formula (I) is a compound of formula (Ia):

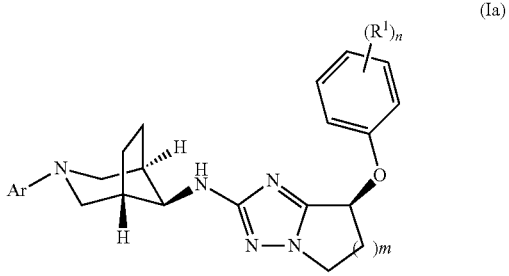

wherein $R^1$, m, n and Ar are as defined above,
or a pharmaceutically acceptable salt thereof.

In one embodiment, there is provided a compound of formula (I) as described herein, wherein the compound of formula (I) is a compound of formula (Ib):

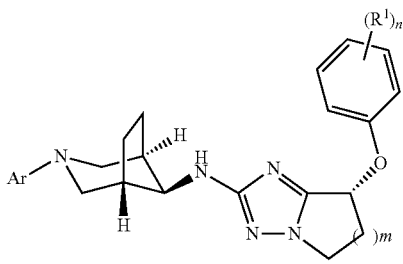

(Ib)

wherein R¹, m, n and Ar are as defined above, or a pharmaceutically acceptable salt thereof.

In one embodiment, R¹ is halogen.

In one embodiment, R¹ is fluorine or chlorine.

In one embodiment, m is 1 or 2.

In one embodiment, there is provided a compound of formula (I) as described herein, or a pharmaceutically acceptable salt thereof, wherein Ar is a six membered heteroaryl group, selected from

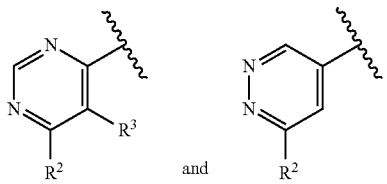

wherein $R^2$ is lower alkyl or lower alkoxy;

$R^3$ is hydrogen.

In a further embodiment, there is provided a compound of formula (I) as described herein, or a pharmaceutically acceptable salt thereof, wherein Ar is a six membered heteroaryl group, selected from

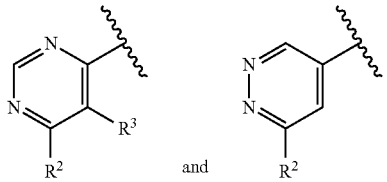

wherein $R^2$ is methyl or methoxy;

$R^3$ is hydrogen.

In a further embodiment, there is provided a compound of formula (I) as described herein, or a pharmaceutically salt thereof, wherein:

R¹ is halogen;

m is 1 or 2;

n is 1, 2 or 3;

Ar is a six membered heteroaryl group, selected from

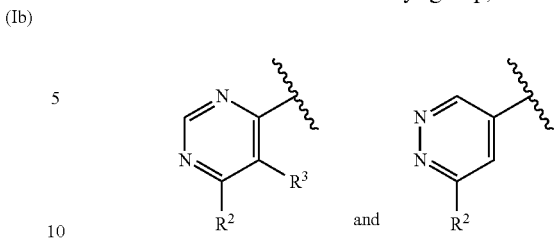

wherein $R^2$ is lower alkyl or lower alkoxy;

$R^3$ is hydrogen.

In a further embodiment, there is provided a compound of formula (I) as described herein, or a pharmaceutically acceptable thereof, wherein:

R¹ is fluorine or chlorine, m is 1 or 2;

n is 1, 2 or 3;

Ar is a six membered heteroaryl group, selected from

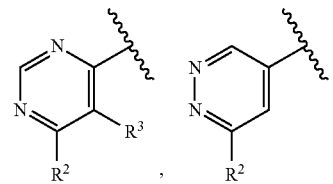

wherein $R^2$ is methyl or methoxy;

$R^3$ is hydrogen.

The compound of formula (I), or pharmaceutically acceptable salts thereof, may contain one or more asymmetric centers and can be present in the form of optically pure enantiomers, mixtures of enantiomers such as, for example, racemates, mixtures of diastereoisomers, diastereoisomeric racemates or mixtures of diastereoisomeric racemates.

In a further embodiment, there is provided a compound of formula (I) as described herein, selected from:

(R)-7-(3,5-difluorophenoxy)-N-((1R,5S,8s)-3-(6-methoxy-pyridazin-4-yl)-3-azabicyclo[3.2.1]octan-8-yl)-6,7-di-hydro-5H-pyrrolo[1,2-b][1,2,4]triazol-2-amine;

(S)-7-(3,5-difluorophenoxy)-N-((1R,5S,8s)-3-(6-methoxy-pyridazin-4-yl)-3-azabicyclo[3.2.1]octan-8-yl)-6,7-di-hydro-5H-pyrrolo[1,2-b][1,2,4]triazol-2-amine;

(R)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;

(S)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;

(R)—N-((1R,5S,8s)-3-(6-methoxypyridazin-4-yl)-3-azabi-cyclo[3.2.1]octan-8-yl)-7-(2,3,4-trifluorophenoxy)-6,7-dihydro-5H-pyrrolo[1,2-b][1,2,4]triazol-2-amine;

(S)—N-((1R,5S,8s)-3-(6-methoxypyridazin-4-yl)-3-azabi-cyclo[3.2.1]octan-8-yl)-7-(2,3,4-trifluorophenoxy)-6,7-dihydro-5H-pyrrolo[1,2-b][1,2,4]triazol-2-amine;

(R)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-8-(3,5-difluorophenoxy)-N-((1R,5S,8s)-3-(6-methoxy-pyridazin-4-yl)-3-azabicyclo[3.2.1]octan-8-yl)-5,6,7,8-tetrahydro-[1,2,4]triazolo[1,5-a]pyridin-2-amine;

(S)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)—N-((1R,5S,8S)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(S)—N-((1R,5S,8S)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(R)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;

(S)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;

(R)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;

(S)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;

(R)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(S)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(R)-8-(2,4-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(2,4-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(S)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(R)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(S)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(R)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(S)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(R)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(S)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(R)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(S)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(R)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;

(S)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;

(R)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(S)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(R)-9-(4-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine;
(S)-9-(4-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine;
(R)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine;
(S)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine;
(R)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine; (S)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine;
or a pharmaceutically acceptable salt thereof.

In a further embodiment, there is provided a compound of formula (I) as described herein, selected from:
(R)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(S)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(R)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(S)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(R)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;
(S)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;
(R)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)—N-((1R,5S,8S)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(S)—N-((1R,5S,8S)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(R)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(S)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(R)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(S)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(R)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine; and
(S)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
or a pharmaceutically acceptable salt thereof.

Processes of Manufacturing

Processes for the manufacture of compounds of formula (I), or pharmaceutically acceptable salts thereof, as described herein are also an object of the present invention.

The preparation of compounds of formula (I) as described herein may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

If one of the starting materials, intermediates or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can, for example, be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

In one embodiment, compounds of formula (I), as described herein or a pharmaceutically acceptable salt thereof, may be prepared by a process comprising reacting a compound 7

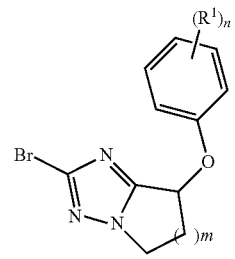

with an amine 8

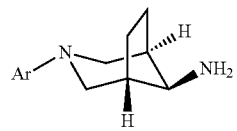

wherein Ar, $R^1$, n and m are as described herein,
to form said compound of formula (I), and if desired, converting the compounds obtained into a pharmaceutically acceptable salt thereof.

In one embodiment, the process according to the invention can be carried out in the presence of a catalyst, e.g. palladium, optionally in the presence of a ligand, e.g. 2-di-tert-butylphosphino-2',4',6'-triisopropylbiphenyl.

In a further embodiment, the process according to the invention can further comprise a step of performing a chiral separation to obtain compounds of formulas (Ia) and (Ib).

In one embodiment, compounds of formula (I) wherein $R^1$, n, m and Ar are as described herein and their intermediates may be prepared in analogy to literature procedures and/or depicted for example in schemes 1 and 2 respectively.

Scheme 1

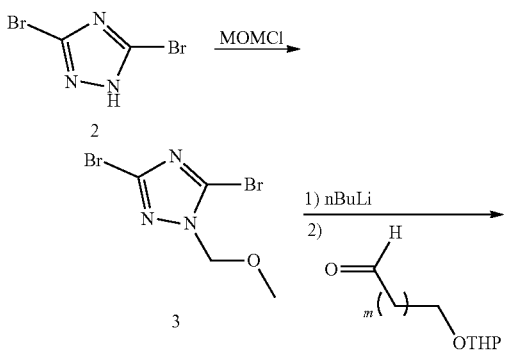

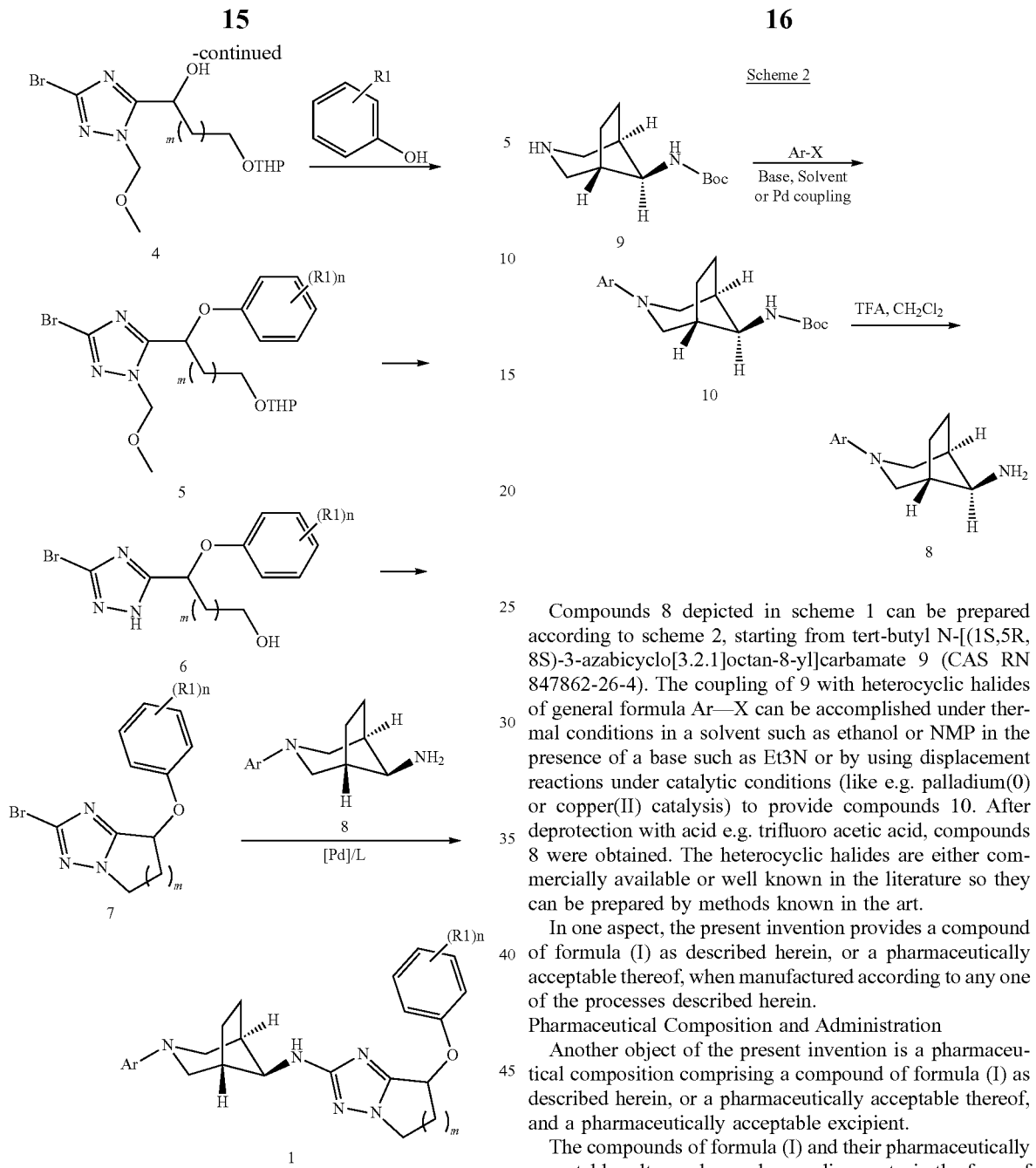

Scheme 2

Compounds 8 depicted in scheme 1 can be prepared according to scheme 2, starting from tert-butyl N-[(1S,5R,8S)-3-azabicyclo[3.2.1]octan-8-yl]carbamate 9 (CAS RN 847862-26-4). The coupling of 9 with heterocyclic halides of general formula Ar—X can be accomplished under thermal conditions in a solvent such as ethanol or NMP in the presence of a base such as Et3N or by using displacement reactions under catalytic conditions (like e.g. palladium(0) or copper(II) catalysis) to provide compounds 10. After deprotection with acid e.g. trifluoro acetic acid, compounds 8 were obtained. The heterocyclic halides are either commercially available or well known in the literature so they can be prepared by methods known in the art.

In one aspect, the present invention provides a compound of formula (I) as described herein, or a pharmaceutically acceptable thereof, when manufactured according to any one of the processes described herein.

Pharmaceutical Composition and Administration

Another object of the present invention is a pharmaceutical composition comprising a compound of formula (I) as described herein, or a pharmaceutically acceptable thereof, and a pharmaceutically acceptable excipient.

The compounds of formula (I) and their pharmaceutically acceptable salts can be used as medicaments, in the form of pharmaceutical preparations. The pharmaceutical preparations can be administered internally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions). The administration can also be effected topically, e.g. transdermal administration, or in form of eye drops or ear drops.

The compounds of formula (I) and their pharmaceutically acceptable salts can be processed with pharmaceutically inert, inorganic or organic carriers for the production of pharmaceutical preparations, such as tablets, coated tablets, dragées, hard gelatin capsules, injection solutions or topical formulations. Lactose, corn starch or derivatives thereof, talc, stearic acids or salts thereof, and the like can be used, The preparation of compounds of formula (I) may start with the protection of 3,5-dibromo-1H-1,2,4-triazole 2 with a MOM group to yield 3. A regioselective halo lithiation with nBuLi followed by the addition of an aldehyde as electrophile containing a carbon chain of different length (m=1, 2 or 3) afforded alcohol 4. A Mitsunobu coupling was then performed using different phenols to provide the aryl ether derivatives 5. After concomitant deprotection of the THP protected primary alcohol and of the MOM protected triazole under acidic condition, derivatives 6 were obtained. An intramolecular cyclisation was then performed using cyanomethylenetrimethylphosphorane to yield 7. Finally, a Buchwald type coupling with amine of formula 8 in a presence of palladium and a ligand afforded the compounds of formula (I). The preparative chiral HPLC allowed the separation of the enantiomers.

for example, as such carriers for tablets, coated tablets, dragées and hard gelatin capsules.

Suitable carriers for soft gelatin capsules are, for example, vegetable oils, waxes, fats, semi-solid substances and liquid polyols and the like. Depending on the nature of the active substance no carriers are, however, usually required in the case of soft gelatin capsules.

Suitable carriers for the production of solutions and syrups are, for example, water, alcohols, polyols, saccharose, glucose, invert sugar, vegetable oil, etc.

Suitable carriers for injection solutions are, for example, water, alcohols, polyols, glycerol, vegetable oils, etc.

Suitable carriers for suppositories are, for example, natural or hardened oils, waxes, fats, semi-liquid or liquid polyols, etc.

Suitable carriers for topical ocular formulations are, for example, cyclodextrins, mannitol or many other carriers and excipients known in the art.

Moreover, the pharmaceutical preparations can contain preservatives, solubilizers, viscosity increasing substances, stabilizers, wetting agents, emulsifiers, sweeteners, colorants, flavorants, salts for varying the osmotic pressure, buffers, masking agents or antioxidants. They can also contain other therapeutically valuable substances.

Medicaments containing a compound of formula (I) or a pharmaceutically acceptable salt thereof and a pharmaceutically acceptable excipient are also an object of the present invention, as is a process for their production, which comprises bringing one or more compounds of formula (I) and/or pharmaceutically acceptable salts thereof and, if desired, one or more other therapeutically valuable substances into a galenical administration form together with one or more pharmaceutically acceptable excipients.

The dosage can vary within wide limits and will, of course, have to be adjusted to the individual requirements in each particular case. In general, in the case of oral administration a daily dosage of about 0.1 mg to 20 mg per kg body weight, preferably 0.5 mg to 4 mg per kg body weight (e.g. about 300 mg per person), divided into preferably 1-3 individual doses, which can consist, for example, of the same amounts, should be appropriate. In the case of topical administration, the formulation can contain 0.001% to 15% by weight of medicament and the required dose, which can be between 0.1 and 25 mg, and can be administered either by single dose per day or per week, or by multiple doses (2 to 4) per day, or by multiple doses per week. It will, however, be clear that the upper or lower limit given herein can be exceeded when this is shown to be indicated.

The pharmaceutical composition according to the invention may be prepared as follows.

Preparation of Pharmaceutical Compositions Comprising Compounds of the Invention

| Tablet Formulation (Wet Granulation) | | | | |
|---|---|---|---|---|
| | mg/tablet | | | |
| Ingredient | 5 | 25 | 100 | 500 |
| 1) Compound of formula (I) | 5 | 25 | 100 | 500 |
| 2) Lactose Anhydrous DTG | 125 | 105 | 30 | 150 |
| 3) Sta-Rx 1500 | 6 | 6 | 6 | 30 |
| 4) Microcrystalline Cellulose | 30 | 30 | 30 | 150 |
| 5) Magnesium Stearate | 1 | 1 | 1 | 1 |
| Total | 167 | 167 | 167 | 831 |

Manufacturing Procedure:
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

| Capsule Formulation | | | | |
|---|---|---|---|---|
| | mg/capsule | | | |
| Ingredient | 5 | 25 | 100 | 500 |
| 1) Compound of formula (I) | 5 | 25 | 100 | 500 |
| 2) Hydrous Lactose | 159 | 123 | 148 | — |
| 3) Corn Starch | 25 | 35 | 40 | 70 |
| 4) Talc | 10 | 15 | 10 | 25 |
| 5) Magnesium Stearate | 1 | 2 | 2 | 5 |
| Total | 200 | 200 | 300 | 600 |

Manufacturing Procedure:
1. Mix ingredients 1, 2 and 3 in a suitable mixer for 30 minutes.
2. Add ingredients 4 and 5 and mix for 3 minutes.
3. Fill into a suitable capsule.

Indications

Also an object of the present invention is a compound of formula (I) as described herein, or a pharmaceutically acceptable thereof, for use as therapeutically active substance.

As described above, compounds of formula (I) and their pharmaceutically acceptable salts are useful as gamma-secretase modulators.

In one aspect, the present invention provides compounds of formula (I) as described herein, or a pharmaceutically acceptable salt thereof, for use in the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome.

In one embodiment, the present invention provides compounds of formula (I) as described herein, or a pharmaceutically acceptable thereof, for use in the therapeutic and/or prophylactic treatment of Alzheimer's disease.

In a further aspect, the present invention provides the use of compounds of formula (I) as described herein, or a pharmaceutically acceptable salt thereof, for the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome.

In one embodiment, the present invention provides the use of compounds of formula (I) as described herein, or a pharmaceutically acceptable salt thereof, for the therapeutic and/or prophylactic treatment of Alzheimer's disease.

In a further aspect, the present invention provides the use of compounds of formula (I) as described herein, or a pharmaceutically acceptable salt thereof, for the preparation of a medicament for the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome.

In one embodiment, the present invention provides the use of compounds of formula (I) as described herein, or a pharmaceutically acceptable salt thereof, for the preparation of a medicament for the therapeutic and/or prophylactic treatment of Alzheimer's disease.

In a further aspect, the present invention provides a method for the therapeutic and/or prophylactic treatment of Alzheimer's disease, cerebral amyloid angiopathy, cochlear synaptopathy, hearing loss, hereditary cerebral hemorrhage with amyloidosis-Dutch type (HCHWA-D), multi-infarct dementia, dementia pugilistica, or Down syndrome, which method comprises administering an effective amount of a compound of formula (I) as described herein, or a pharmaceutically acceptable salt thereof.

In one embodiment, the present invention provides a method for the therapeutic and/or prophylactic treatment of Alzheimer's disease which method comprises administering an effective amount of a compound of formula (I) as described herein, or a pharmaceutically acceptable salt thereof.

EXAMPLES

The invention will be more fully understood by reference to the following examples. The claims should not, however, be construed as limited to the scope of the examples.

1) Preparative Examples

1.1) General

Analytical Method: HPLC (Method LCMS_fastgradient)

Column: Agilent Zorbax Eclipse Plus C18, Rapid Resolution HT, 2.1×30 mm, 1.8 μm

Solvent A: Water 0.01% Formic Acid; Solvent B: acetonitrile (MeCN)

Gradients:

| Time [min] | Flow Rate [ml/min] | % A | % B |
| --- | --- | --- | --- |
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

1.2) Preparation of Intermediates 1.2.1) Intermediates of Type 7, with m=1

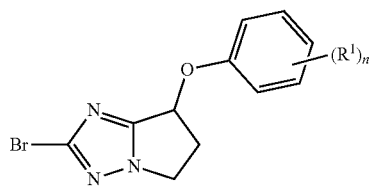

Intermediate 7-1

2-bromo-7-(3,5-difluorophenoxy)-6,7-dihydro-5H-pyrrolo[1,2-b][1,2,4]triazole

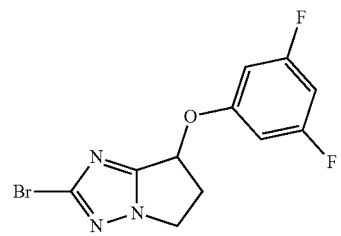 [SMILES: Fc1cc(F)cc(OC2CCn3nc(Br)nc32)c1]

Step 1: 3,5-dibromo-1H-1,2,4-triazole (10 g, 44.1 mmol, Eq: 1) was combined with DMF (175 ml) to give a light yellow solution. Under stirring and argon, sodium hydride (60% in oil) (2.12 g, 52.9 mmol, Eq: 1.2) was added in portions (max. 250 mg) over a period of 45 min. at max. 25° C. and was then stirred 1 h at RT. Chloro(methoxy)methane (3.55 g, 3.35 ml, 44.1 mmol, Eq: 1) was added dropwise over a period of 20 min. at max 25° C. and then stirred under argon at RT for 2 h. The reaction mixture was poured into iced water (400 ml) and extracted 3 times with TBME (600 ml). The organic layers were washed with water (300 ml) and then with brine (300 ml). The organic layers were combined, dried over sodium sulfate, filtered and evaporated in vacuo. The residue was purified by column chromatography (Hept: EtOAc 95:5 to 50:50) to afford 3,5-dibromo-1-(methoxymethyl)-1H-1,2,4-triazole as a white solid (10.2 g 85%). MS (ES+) m/z: 272.1 [(M+H)$^+$].

Step 2: 3,5-dibromo-1-(methoxymethyl)-1H-1,2,4-triazole (3 g, 11.1 mmol, Eq: 1) was combined with THF (27 ml) to give a colorless solution and then cooled in a dry ice/acetone bath to −75° C. N-butyllithium 1.6 M in hexane (7.34 ml, 11.7 mmol, Eq: 1.06) was added dropwise over a period of 20 min. The yellow solution was stirred 45 min. at −75° C. Now a solution of 3-((tetrahydro-2H-pyran-2-yl)oxy)propanal (2.1 g, 13.3 mmol, Eq: 1.2) in THF (27 ml) was added dropwise over a period of 30 min and then stirred for 45 min at −75° C. The dry-ice/acetone bath was removed and the reaction was let to warm over 1 h to ca. 15° C. and then quenched with 60 ml of a saturated NH$_4$Cl-solution, followed by 45 ml water and 90 ml EtOAc. The mixture was stirred 5 min. The layers were separated. The aqueous layer was back extracted with EtOAc (2×90 ml). The organic layers were washed with brine (60 ml). The organic layers were combined, dried over sodium sulfate, filtered and evaporated in vacuo. The residue was purified by ISCO chromatography (Hept: EtOAc 80:20 to 0:100) to afford 1-(3-bromo-1-(methoxymethyl)-1H-1,2,4-triazol-5-yl)-3-((tetrahydro-2H-pyran-2-yl)oxy)propan-1-ol as a colorless oil (3.25 g 83.8%). MS (ES+) m/z: 352.0 [(M+H)$^+$].

Step 3: 1-(3-bromo-1-(methoxymethyl)-1H-1,2,4-triazol-5-yl)-3-((tetrahydro-2H-pyran-2-yl)oxy)propan-1-ol (500 mg, 1.43 mmol, Eq: 1) was combined with extra dry THF (25 ml) to give a colorless solution and under stirring and argon, 3,5-difluorophenol (223 mg, 1.71 mmol, Eq: 1.2) and triphenylphosphine (468 mg, 1.78 mmol, Eq: 1.25) were added. The reaction mixture was cooled under stirring and argon in an ice bath. DIAD (361 mg, 347 μl, 1.78 mmol, Eq: 1.25) was added dropwise over a period of 2-3 min. at max +3-5° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3,5-difluorophenoxy)-3-((tetrahydro-2H-pyran-2-yl)oxy)propyl)-1-(methoxymethyl)-1H-1,2,4-triazole as a colorless oil (542 mg, 82%). MS (ES+) (−THP) m/z: 378.1/380.1 [(M+H)+].

Step 4: 3-bromo-5-(1-(3,5-difluorophenoxy)-3-((tetrahydro-2H-pyran-2-yl)oxy)propyl)-1-(methoxymethyl)-1H-1,2,4-triazole (535 mg, 1.16 mmol, Eq: 1) was combined with methanol (9 ml) to give a colorless solution. Under stirring and argon, 37% HCl in water (4.56 g, 3.8 ml, 46.3 mmol, Eq: 40) was added. The reaction mixture was stirred 30 min without heating, followed by 1 h at reflux. Then the reaction mixture was cooled to RT and poured into ice water (30 ml), neutralized with solid sodium bicarbonate and extracted with EtOAc (80 ml). The aqueous layer was back extracted with EtOAc (2×50 ml). The organic layers were combined, dried over sodium sulfate, filtered and evaporated in vacuo. The residue was purified by ISCO chromatography (Hept: EtOAc 90:10 to 0:100) to afford 3-(3-bromo-1H-1,2,4-triazol-5-yl)-3-(3,5-difluorophenoxy)propan-1-ol as a white solid (350 mg, 90%). MS (ES+) m/z: 334.0 [(M+H)+].

Step 5: 3-(3-bromo-1H-1,2,4-triazol-5-yl)-3-(3,5-difluorophenoxy)propan-1-ol (350 mg, 1.05 mmol, Eq: 1) was combined with extra dry THF (11 ml) to give a colorless solution. Under stirring and argon, cyanomethylenetrimethylphosphorane solution in THF (0.5M) (2.62 ml, 1.31 mmol, Eq: 1.25) was added dropwise over a period of 5 min. The reaction mixture was stirred 1.5 h at reflux. Then the reaction mixture was cooled to RT and extracted with EtOAc (80 ml) and saturated sodium bicarbonate solution (15 ml). The aqueous layer was back extracted with EtOAc (2×60 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-7-(3,5-difluorophenoxy)-6,7-dihydro-5H-pyrrolo[1,2-b][1,2,4]triazole as a colorless oil (255 mg, 77%). MS (ES+) m/z: 315.9 [(M+H)+].

in vacuo and purified by ISCO chromatography (Hept: EtOAc 95:5 to 50:50) to afford 3-bromo-5-(1-(3-chloro-5-fluorophenoxy)-3-((tetrahydro-2H-pyran-2-yl)oxy)propyl)-1-(methoxymethyl)-1H-1,2,4-triazole as a colorless oil (605 mg, 88%). GCMS (FI+) m/z: 478.9 [(M+H)+]

Step 2: 3-bromo-5-(1-(3-chloro-5-fluorophenoxy)-3-((tetrahydro-2H-pyran-2-yl)oxy)propyl)-1-(methoxymethyl)-1H-1,2,4-triazole (600 mg, 1.25 mmol, Eq: 1) was combined with methanol (9.5 ml) to give a colorless solution. Under stirring and argon, 37% HCl in water (4.94 g, 4.12 ml, 50.1 mmol, Eq: 40) was added. The reaction mixture was stirred for 30 min without heating, followed by 1 h at reflux. Cooled to RT and poured into ice water (30 ml), neutralized with solid sodium bicarbonate and extracted with EtOAc (80 ml). The aqueous layer was back extracted with EtOAc (2×50 ml). The organic layers were combined, dried over sodium sulfate, filtered and evaporated in vacuo. The residue was purified by ISCO chromatography (Hept: EtOAc 90:10 to 0:100) to afford 3-(3-bromo-1H-1,2,4-triazol-5-yl)-3-(3-chloro-5-fluorophenoxy)propan-1-ol as a colorless foam (405 mg, 92%). MS (ES+) m/z: 351.9 [(M+H)+].

Step 3: 3-(3-bromo-1H-1,2,4-triazol-5-yl)-3-(3-chloro-5-fluorophenoxy)propan-1-ol (405 mg, 1.16 mmol, Eq: 1) was combined with extra dry THF (12.5 ml) to give a colorless solution. Under stirring and argon, cyanomethylenetrimethylphosphorane solution in THF (0.5M) (2.89 ml, 1.44 mmol, Eq: 1.25) was added dropwise over a period of 5 min. The reaction mixture was stirred 1.5 h at reflux. Then the reaction mixture was cooled to RT and extracted with EtOAc (80 ml) and saturated sodium bicarbonate solution (15 ml). The aqueous layer was back extracted with EtOAc (2×60 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-7-(3-chloro-5-fluorophenoxy)-6,7-dihydro-5H-pyrrolo[1,2-b][1,2,4]triazole as a colorless oil (284 mg, 73%). MS (ES+) m/z: 333.9 [(M+H)+].

Intermediate 7-2

2-bromo-7-(3-chloro-5-fluorophenoxy)-6,7-dihydro-5H-pyrrolo[1,2-b][1,2,4]triazole Intermediate 7-3

2-bromo-7-(2,3,4-trifluorophenoxy)-6,7-dihydro-5H-pyrrolo[1,2-b][1,2,4]triazole

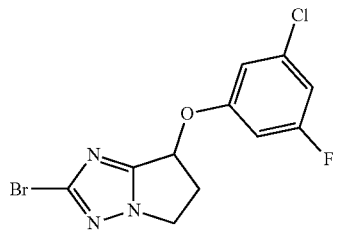 [SMILES: Fc1cc(Cl)cc(OC2CCn3nc(Br)nc32)c1]

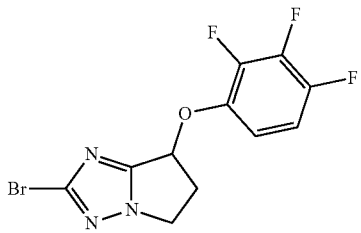 [SMILES: Fc1ccc(OC2CCn3nc(Br)nc32)c(F)c1F]

Step 1: 1-(3-bromo-1-(methoxymethyl)-1H-1,2,4-triazol-5-yl)-3-((tetrahydro-2H-pyran-2-yl)oxy)propan-1-ol (500 mg, 1.43 mmol, Eq: 1, described herein above), 3-chloro-5-fluorophenol (209 mg, 1.43 mmol, Eq: 1) and triphenylphosphine (468 mg, 1.78 mmol, Eq: 1.25) were combined with extra dry THF (25 ml) to give a colorless solution. The reaction mixture was cooled under stirring and Argon, in an ice bath. DIAD (361 mg, 347 µl, 1.78 mmol, Eq: 1.25) was added dropwise over a period of 5 min at max +3° C. The ice bath was removed and the reaction mixture was stirred 2 h at RT. The reaction mixture was evaporated Step 1: 1-(3-bromo-1-(methoxymethyl)-1H-1,2,4-triazol-5-yl)-3-((tetrahydro-2H-pyran-2-yl)oxy)propan-1-ol (504 mg, 1.44 mmol, Eq: 1, described herein above), 2,3,4-trifluorophenol (256 mg, 1.73 mmol, Eq: 1.2) and triphenylphosphine (472 mg, 1.8 mmol, Eq: 1.25) were combined with THF (25 ml) to give a colorless solution. The reaction mixture was cooled under stirring and argon, in an ice bath. DIAD (364 mg, 350 µl, 1.8 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-1-(methoxymethyl)-5-(3-((tetrahydro-2H-pyran-2-yl)oxy)-1-(2,3,4-trifluorophenoxy)propyl)-1H-1,2,4-triazole as a light yellow oil (632 mg, 91%). GCMS (FI+) m/z: 479.0 [(M+H)+].

Step 2: 3-bromo-1-(methoxymethyl)-5-(3-((tetrahydro-2H-pyran-2-yl)oxy)-1-(2,3,4-trifluorophenoxy)propyl)-1H-1,2,4-triazole (154 mg, 321 μmol, Eq: 1) was combined with methanol (2.5 ml) to give a colorless solution. Under stirring and argon 37% HCl in water (1.26 g, 1.05 ml, 12.8 mmol, Eq: 40) was added. The reaction mixture was stirred 30 min without heating, followed by 1 h at reflux. Then the reaction mixture was cooled to RT and poured into ice water (10 ml), neutralized with solid sodium bicarbonate and extracted with EtOAc (30 ml). The aqueous layer was back extracted with EtOAc (2×50 ml). The organic layers were combined, dried over sodium sulfate, filtered and evaporated in vacuo. The residue was purified by ISCO chromatography (Hept: EtOAc 90:10 to 0:100) to afford 3-(3-bromo-1H-1,2,4-triazol-5-yl)-3-(2,3,4-trifluorophenoxy)propan-1-ol as a colorless viscous oil (106 mg, 93%). MS (ES+) m/z: 353.9 [(M+H)+].

Step 3: 3-(3-bromo-1H-1,2,4-triazol-5-yl)-3-(2,3,4-trifluorophenoxy)propan-1-ol (102 mg, 290 μmol, Eq: 1) was combined with extra dry THF (3 ml) to give a colorless solution. Under stirring and argon, cyanomethylenetrimethylphosphorane solution in THF (0.5 M) (724 μl, 362 μmol, Eq: 1.25) was added dropwise over a period of 5 min. The reaction mixture was stirred 1.5 h at reflux. The reaction mixture was then cooled to RT and extracted with EtOAc (20 ml) and saturated sodium bicarbonate solution (3 ml). The aqueous layer was back extracted with EtOAc (2×20 ml). The organic layers were combined, dried over sodium sulfate, filtered and evaporated in vacuo. The residue was purified by ISCO chromatography (Hept: EtOAc 95:5 to 0:100) to afford 2-bromo-7-(2,3,4-trifluorophenoxy)-6,7-dihydro-5H-pyrrolo[1,2-b][1,2,4]triazole as a colorless oil (70 mg, 72%). MS (ES+) m/z: 333.9 [(M+H)+].

Intermediate 7-4

2-bromo-7-(4-chlorophenoxy)-6,7-dihydro-5H-pyrrolo[1,2-b][1,2,4]triazole

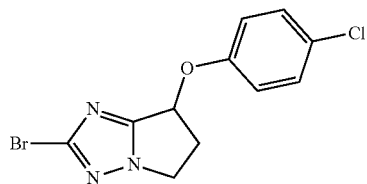 [SMILES: Clc1ccc(OC2CCn3nc(Br)nc32)cc1]

Step 1: 1-(3-bromo-1-(methoxymethyl)-1H-1,2,4-triazol-5-yl)-3-((tetrahydro-2H-pyran-2-yl)oxy)propan-1-ol (500 mg, 1.43 mmol, Eq: 1, described herein above), 4-chlorophenol (220 mg, 1.71 mmol, Eq: 1.2) and triphenylphosphine (468 mg, 1.78 mmol, Eq: 1.25) were combined with THF (25 ml) to give a colorless solution. The reaction mixture was cooled under stirring and argon in an ice bath. DIAD (361 mg, 347 μl, 1.78 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-1-(methoxymethyl)-5-(3-((tetrahydro-2H-pyran-2-yl)oxy)-1-(2,3,4-trifluorophenoxy)propyl)-1H-1,2,4-triazole as a colorless oil (520 mg, 79%). MS (ES+) m/z: 462.1 [(M+H)+].

Step 2: 3-bromo-5-(1-(4-chlorophenoxy)-3-((tetrahydro-2H-pyran-2-yl)oxy)propyl)-1-(methoxymethyl)-1H-1,2,4-triazole (517 mg, 1.12 mmol, Eq: 1) was combined with MeOH (9 nil) to give a colorless solution. Under stirring and argon, 37% HCl in water (4.42 g, 3.69 ml, 44.9 mmol, Eq: 40) was added. The reaction mixture was stirred 30 min without heating, followed by 1 h at reflux. Then the reaction mixture was cooled to RT and poured into ice water (35 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 3-(3-bromo-1H-1,2,4-triazol-5-yl)-3-(4-chlorophenoxy)propan-1-ol as a white foam (335 mg, 89%). MS (ES+) m/z: 331.9 [(M+H)+].

Step 3: 3-(3-bromo-1H-1,2,4-triazol-5-yl)-3-(4-chlorophenoxy)propan-1-ol (323 mg, 971 μmol, Eq: 1) was combined with extra dry THF (10 ml) to give a colorless solution. Under stirring and argon, cyanomethylenetrimethylphosphorane solution in THF (0.5 M) (2.43 ml, 1.21 mmol, Eq: 1.25) was added dropwise over a period of 5 min. The reaction mixture was stirred 1.5 h at reflux. Cooled to RT and extracted with EtOAc (80 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-7-(4-chlorophenoxy)-6,7-dihydro-5H-pyrrolo[1,2-b][1,2,4]triazole as a white solid (240 mg, 78%) MS (ES+) m/z: 315.9 [(M+H)+].

Intermediate 7-5

2-bromo-7-(3-chlorophenoxy)-6,7-dihydro-5H-pyrrolo[1,2-b][1,2,4]triazole

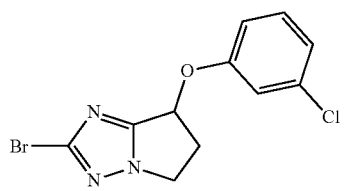 [SMILES: Clc1cccc(OC2CCn3nc(Br)nc32)c1]

Step 1: 1-(3-bromo-1-(methoxymethyl)-1H-1,2,4-triazol-5-yl)-3-((tetrahydro-2H-pyran-2-yl)oxy)propan-1-ol (500 mg, 1.43 mmol, Eq: 1, described herein above), 3-chlorophenol (220 mg, 1.71 mmol, Eq: 1.2) and triphenylphosphine (468 mg, 1.78 mmol, Eq: 1.25) (468 mg, 1.78 mmol, Eq: 1.25) were combined with THF (25 ml) to give a colorless solution. The reaction mixture was cooled under stirring and argon, in an ice bath. DIAD (361 mg, 347 μl, 1.78 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-

(3-chlorophenoxy)-3-((tetrahydro-2H-pyran-2-yl)oxy)propyl)-1-(methoxymethyl)-1H-1,2,4-triazole as a colorless oil (545 mg, 82%). MS (ES+) m/z: 462.1 [(M+H)+].

Step 2: 3-bromo-5-(1-(3-chlorophenoxy)-3-((tetrahydro-2H-pyran-2-yl)oxy)propyl)-1-(methoxymethyl)-1H-1,2,4-triazole (540 mg, 1.17 mmol, Eq: 1) was combined with MeOH (9 ml) to give a colorless solution. Under stirring and argon, 37% HCl in water (4.62 g, 3.85 ml, 46.9 mmol, Eq: 40) was added. The reaction mixture was stirred 30 min without heating, followed by 1 h at reflux. Then the reaction mixture was cooled to RT and poured into ice water (35 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 3-(3-bromo-1H-1,2,4-triazol-5-yl)-3-(3-chlorophenoxy)propan-1-ol as a colorless viscous oil (360 mg, 92%). MS (ES+) m/z: 331.9 [(M+H)+].

Step 3: 3-(3-bromo-1H-1,2,4-triazol-5-yl)-3-(3-chlorophenoxy)propan-1-ol (355 mg, 1.07 mmol, Eq: 1) was combined with extra dry THF (11 ml) to give a colorless solution. Under stirring and argon, cyanomethylenetrimethylphosphorane solution in THF (0.5 M) (2.67 ml, 1.33 mmol, Eq: 1.25) was added dropwise over a period of 5 min. The reaction mixture was stirred 1.5 h at reflux. Then the reaction mixture was cooled to RT and extracted with EtOAc (80 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-7-(3-chlorophenoxy)-6,7-dihydro-5H-pyrrolo[1,2-b][1,2,4]triazole as a colorless oil (249 mg, 74%) MS (ES+) m/z: 315.9 [(M+H)+].

Intermediate 7-6

2-bromo-7-(3,5-dichlorophenoxy)-6,7-dihydro-5H-pyrrolo[1,2-b][1,2,4]triazole

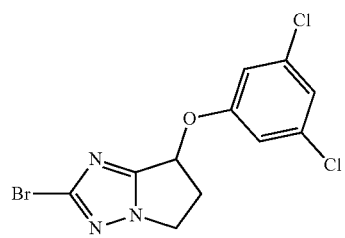

Step 1: 1-(3-bromo-1-(methoxymethyl)-1H-1,2,4-triazol-5-yl)-3-((tetrahydro-2H-pyran-2-yl)oxy)propan-1-ol (500 mg, 1.43 mmol, Eq: 1, described herein above), 3,5-dichlorophenol (279 mg, 1.71 mmol, Eq: 1.2) and triphenylphosphine (468 mg, 1.78 mmol, Eq: 1.25) were combined with THF (25 ml) to give a colorless solution. The reaction mixture was cooled under stirring and Argon, in an ice bath. DIAD (361 mg, 347 µl, 1.78 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3,5-dichlorophenoxy)-3-((tetrahydro-2H-pyran-2-yl)oxy)propyl)-1-(methoxymethyl)-1H-1,2,4-triazole as a colorless oil (625 mg, 82%). GCMS m/z: 494.0 [(M+H)+].

Step 2: 3-bromo-5-(1-(3,5-dichlorophenoxy)-3-((tetrahydro-2H-pyran-2-yl)oxy)propyl)-1-(methoxymethyl)-1H-1,2,4-triazole (620 mg, 1.25 mmol, Eq: 1) was combined with MeOH (10 ml) to give a colorless solution. Under stirring and argon, 37% HCl in water (4.93 g, 4.11 ml, 50.1 mmol, Eq: 40) was added. The reaction mixture was stirred 30 min without heating, followed by 1 h at reflux. The reaction was then cooled to RT and poured into ice water (35 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 3-(3-bromo-1H-1,2,4-triazol-5-yl)-3-(3,5-dichlorophenoxy)propan-1-ol as a white foam (408 mg, 88%). MS (ES+) m/z: 367.9 [(M+H)+].

Step 3: 3-(3-bromo-1H-1,2,4-triazol-5-yl)-3-(3,5-dichlorophenoxy)propan-1-ol (400 mg, 1.09 mmol, Eq: 1) was combined with extra dry THF (11.5 ml) to give a colorless solution. Under stirring and argon, cyanomethylenetrimethylphosphorane solution in THF (0.5 M) (2.72 ml, 1.36 mmol, Eq: 1.25) was added dropwise over a period of 5 min. The reaction mixture was stirred 1.5 h at reflux. The reaction mixture was then cooled to RT and extracted with EtOAc (80 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-7-(3,5-dichlorophenoxy)-6,7-dihydro-5H-pyrrolo[1,2-b][1,2,4]triazole as a colorless oil (288 mg, 75%) MS (ES+) m/z: 349.9 [(M+H)+].

1.2.2) Intermediates of Type 7, with m=2

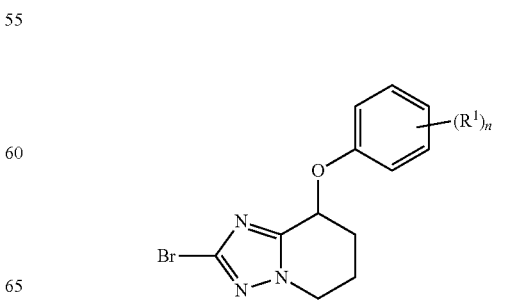

Intermediate 7-7

2-bromo-8-(3-chloro-5-fluorophenoxy)-5,6,7,8-tetrahydro-[1,2,4]triazolo[1,5-a]pyridine

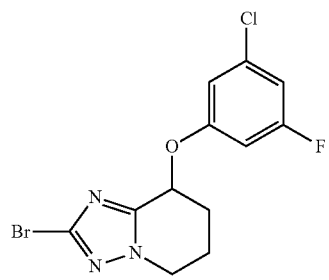 [SMILES: Fc1cc(Cl)cc(OC2CCCn3nc(Br)nc32)c1]

Step 1: 3,5-dibromo-1-(methoxymethyl)-1H-1,2,4-triazole (4 g, 14.8 mmol, Eq: 1, described herein above) was combined with THF (36 ml) to give a colorless solution and cooled in a dry ice/acetone bath to −75° C. n-Butyllithium (1.6 M in hexane, 9.78 ml, 15.7 mmol, Eq: 1.06) was added dropwise over a period of 20 min. The yellow solution was stirred 45 min at −75° C. Then a solution of 4-((tetrahydro-2H-pyran-2-yl)oxy)butanal (3.05 g, 17.7 mmol, Eq: 1.2) in THF (36 ml) was added dropwise over a period of 30 min and the mixture was then stirred for 45 min at −75° C. The dry ice/acetone bath was removed and the reaction mixture was let to warm over 1 h to ca. 15° C. and then quenched with 80 ml of saturated $NH_4Cl$ solution, followed by 55 ml water and 120 ml of EtOAc. The mixture was stirred 5 min. The layers were separated. The aqueous layer was back extracted with EtOAc (2×120 ml). The organic layers were washed with brine (80 ml). The organic layers were combined, dried over sodium sulfate, filtered and evaporated in vacuo. The residue was purified by ISCO chromatography (Hept: EtOAc 80:20 to 0:100) to afford 1-(3-bromo-1-(methoxymethyl)-1H-1,2,4-triazol-5-yl)-4-((tetrahydro-2H-pyran-2-yl)oxy)butan-1-ol as a colorless oil (3.75 g 69%). MS (ES+) m/z: 364.0 [(M+H)$^+$].

Step 2: 1-(3-bromo-1-(methoxymethyl)-1H-1,2,4-triazol-5-yl)-4-((tetrahydro-2H-pyran-2-yl)oxy)butan-1-ol (500 mg, 1.37 mmol, Eq: 1), 3-chloro-5-fluorophenol (241 mg, 1.65 mmol, Eq: 1.2) and triphenylphosphine (450 mg, 1.72 mmol, Eq: 1.25) were combined with THF (25 ml) to give a colorless solution. The reaction mixture was cooled under stirring and argon in an ice bath. DIAD (347 mg, 334 µl, 1.72 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3-chloro-5-fluorophenoxy)-4-((tetrahydro-2H-pyran-2-yl)oxy)butyl)-1-(methoxymethyl)-1H-1,2,4-triazole as a colorless oil (620 mg, 91%). MS (ES+) m/z: 410.0 (−THP) [(M+H)$^+$].

Step 3: 3-bromo-5-(1-(3-chloro-5-fluorophenoxy)-4-((tetrahydro-2H-pyran-2-yl)oxy)butyl)-1-(methoxymethyl)-1H-1,2,4-triazole (620 mg, 1.26 mmol, Eq: 1) was combined with MeOH (10 ml) to give a colorless solution. Under stirring and argon, 37% HCl in water (4.96 g, 4.13 ml, 50.3 mmol, Eq: 40) was added. The reaction mixture was stirred 30 min without heating, followed by 1 h at reflux. The reaction mixture was stirred 30 min without heating, followed by 1 h at reflux. The reaction mixture was then cooled to RT and poured into ice water (35 ml), neutralized with solid sodium bicarbonate and extracted with EtOAc (100 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(3-chloro-5-fluorophenoxy)butan-1-ol as a colorless viscous oil (435 mg, 94%). MS (ES+) m/z: 365.9 [(M+H)$^+$].

Step 4: 4-(3-bromo-1H-1,2,4-triazol-5-yl)-4-(3-chloro-5-fluorophenoxy)butan-1-ol (430 mg, 1.18 mmol, Eq: 1) was combined with extra dry THF (12 ml) to give a colorless solution. Under stirring and argon, cyanomethylenetrimethylphosphorane solution in THF (0.5 M) (2.95 ml, 1.47 mmol, Eq: 1.25) was added dropwise over a period of 5 min. The reaction mixture was stirred 1.5 h at reflux. The reaction mixture was then cooled to RT and extracted with EtOAc (70 ml) and saturated sodium bicarbonate solution (10 ml). The aqueous layer was back extracted with EtOAc (2×40 ml). The organic layers were combined, dried over sodium sulfate, filtered and evaporated in vacuo. The residue was purified by ISCO chromatography (Hept: EtOAc 95:5 to 0:100) to afford 2-bromo-8-(3-chloro-5-fluorophenoxy)-5,6,7,8-tetrahydro-[1,2,4]triazolo[1,5-a]pyridine as a colorless oil (320 mg, 78%) MS (ES+) m/z: 347.9 [(M+H)$^+$].

Intermediate 7-8

2-bromo-8-(3,5-difluorophenoxy)-5,6,7,8-tetrahydro-[1,2,4]triazolo[1,5-a]pyridine

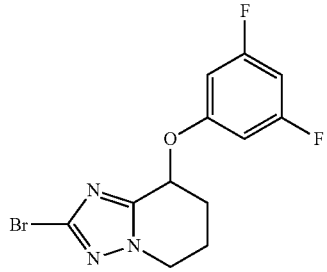 [SMILES: Fc1cc(F)cc(OC2CCCn3nc(Br)nc32)c1]

Step 1: 1-(3-bromo-1-(methoxymethyl)-1H-1,2,4-triazol-5-yl)-4-((tetrahydro-2H-pyran-2-yl)oxy)butan-1-ol (550 mg, 1.51 mmol, Eq: 1, described herein above), 3,5-difluorophenol (196 mg, 1.51 mmol, Eq: 1) and triphenylphosphine (495 mg, 1.89 mmol, Eq: 1.25) were combined with THF (27 ml) to give a colorless solution. The reaction mixture was cooled under stirring and argon in an ice bath. DIAD (382 mg, 367 µl, 1.89 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3,5-difluorophenoxy)-4-((tetrahydro-2H-pyran-2-yl)oxy)butyl)-1-(methoxymethyl)-1H-1,2,4-triazole as a colorless oil (530 mg, 73%). MS (ES+) m/z: 476.0 [(M+H)$^+$].

Step 2: 3-bromo-5-(1-(3,5-difluorophenoxy)-4-((tetrahydro-2H-pyran-2-yl)oxy)butyl)-1-(methoxymethyl)-1H-1,2,4-triazole (530 mg, 1.11 mmol, Eq: 1) was combined with MeOH (8.5 ml) to give a colorless solution. Under stirring and Argon, 37% HCl in water (4.39 g, 3.65 ml, 44.5 mmol, Eq: 40) was added. The reaction mixture was stirred 30 min without heating, followed by 1 h at reflux. The reaction was then cooled to RT and poured into ice water (30 ml), neutralized with solid sodium bicarbonate and extracted with EtOAc (90 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(3,5-difluorophenoxy)butan-1-ol as a colorless viscous oil (372 mg, 96%). MS (ES+) m/z: 348.0 [(M+H)$^+$].

Step 3: 4-(3-bromo-1H-1,2,4-triazol-5-yl)-4-(3,5-difluorophenoxy)butan-1-ol (370 mg, 1.06 mmol, Eq: 1) was combined with extra dry THF (11 ml) to give a colorless solution. Under stirring and argon, cyanomethylenetrimethylphosphorane solution in THF (0.5 M) (2.66 ml, 1.33 mmol, Eq: 1.25) was added dropwise over a period of 5 min. The reaction mixture was stirred 1.5 h at reflux. Then the reaction mixture was cooled to RT and extracted with EtOAc (80 ml) and saturated sodium bicarbonate solution (15 ml). The aqueous layer was back extracted with EtOAc (2×60 ml). The organic layers were washed with brine (80 ml). The organic layers were combined, dried over sodium sulfate, filtered and evaporated in vacuo. The residue was purified by ISCO chromatography (Hept: EtOAc 95:5 to 0:100) to afford 2-bromo-8-(3,5-difluorophenoxy)-5,6,7,8-tetrahydro-[1,2,4]triazolo[1,5-a]pyridine as a colorless oil (254 mg, 72%) MS (ES+) m/z: 330.0 [(M+H)$^+$].

Intermediate 7-9

2-bromo-8-(2,3,4-trifluorophenoxy)-5,6,7,8-tetrahydro-[1,2,4]triazolo[1,5-a]pyridine

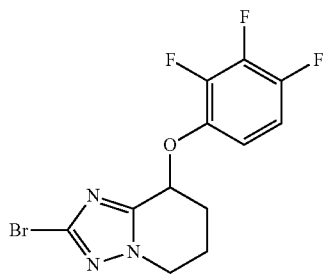 [SMILES: Fc1ccc(OC2CCCn3nc(Br)nc32)c(F)c1F]

Step 1: 1-(3-bromo-1-(methoxymethyl)-1H-1,2,4-triazol-5-yl)-4-((tetrahydro-2H-pyran-2-yl)oxy)butan-1-ol (500 mg, 1.37 mmol, Eq: 1, described herein above), 2,3,4-trifluorophenol (244 mg, 1.65 mmol, Eq: 1.2) and triphenylphosphine (450 mg, 1.72 mmol, Eq: 1.25) were combined with THF (25 ml) to give a colorless solution. The reaction mixture was cooled under stirring and Argon, in an ice bath. DIAD (347 mg, 334 µl, 1.72 mmol, Eq: 1.25) was added dropwise over a period of 5 min. at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-1-(methoxymethyl)-5-(4-((tetrahydro-2H-pyran-2-yl)oxy)-1-(2,3,4-trifluorophenoxy)butyl)-1H-1,2,4-triazole as a light yellow oil (575 mg, 84%). MS (ES+) m/z: 412.0 (-THP) [(M+H)$^+$].

Step 2: 3-bromo-1-(methoxymethyl)-5-(4-((tetrahydro-2H-pyran-2-yl)oxy)-1-(2,3,4-trifluorophenoxy)butyl)-1H-1,2,4-triazole (570 mg, 1.15 mmol, Eq: 1) was combined with MeOH (9 ml) to give a colorless solution. Under stirring and argon, 37% HCl in water (4.54 g, 3.79 ml, 46.1 mmol, Eq: 40) was added. The reaction mixture was stirred 30 min without heating, followed by 1 h at reflux. Then the reaction mixture was cooled to RT and poured into ice water (30 ml), neutralized with solid sodium bicarbonate and extracted with EtOAc (100 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(2,3,4-trifluorophenoxy)butan-1-ol as a colorless viscous oil (400 mg, 94%). MS (ES+) m/z: 366.0 [(M+H)$^+$].

Step 3: 4-(3-bromo-1H-1,2,4-triazol-5-yl)-4-(2,3,4-trifluorophenoxy)butan-1-ol (395 mg, 1.08 mmol, Eq: 1) was combined with extra dry THF (11 ml) to give a colorless solution. Under stirring and argon, cyanomethylenetrimethylphosphorane solution in THF (0.5M) (2.7 ml, 1.35 mmol, Eq: 1.25) was added dropwise over a period of 5 min. The reaction mixture was stirred 1 h at reflux. Then the reaction mixture was cooled to RT and extracted with EtOAc (70 ml) and saturated sodium bicarbonate solution (10 ml). The aqueous layer was back extracted with EtOAc (2×40 ml). The organic layers were combined, dried over sodium sulfate, filtered and evaporated in vacuo. The residue was purified by ISCO chromatography (Hept: EtOAc 95:5 to 50:50) to afford 2-bromo-8-(2,3,4-trifluorophenoxy)-5,6,7,8-tetrahydro-[1,2,4]triazolo[1,5-a]pyridine as a colorless oil (285 mg, 75%) MS (ES+) m/z: 347.9 [(M+H)$^+$].

Intermediate 7-10

2-bromo-8-(2,4-difluorophenoxy)-5,6,7,8-tetrahydro-[1,2,4]triazolo[1,5-a]pyridine

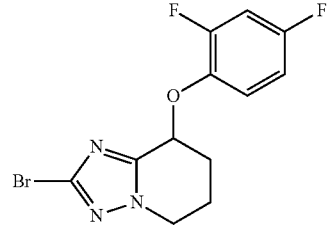 [SMILES: Fc1ccc(OC2CCCn3nc(Br)nc32)c(F)c1]

Step 1: 1-(3-bromo-1-(methoxymethyl)-1H-1,2,4-triazol-5-yl)-4-((tetrahydro-2H-pyran-2-yl)oxy)butan-1-ol (495 mg, 1.36 mmol, Eq: 1, described herein above), 2,4-difluorophenol (212 mg, 1.63 mmol, Eq: 1.2) and triphenylphosphine (450 mg, 1.72 mmol, Eq: 1.25) were combined with THF (25 ml) to give a colorless solution. The reaction mixture was cooled under stirring and argon, in an ice bath. DIAD (344 mg, 330 µl, 1.7 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(2,4-difluorophenoxy)-4-((tetrahydro-2H-pyran-2-yl)oxy)butyl)-1-(methoxymethyl)-1H-1,2,4-triazole as a colorless oil (549 mg, 84%). MS (ES+) m/z: 392.0 (-THP) [(M+H)$^+$].

Step 2: 3-bromo-5-(1-(2,4-difluorophenoxy)-4-((tetrahydro-2H-pyran-2-yl)oxy)butyl)-1-(methoxymethyl)-1H-1,2,4-triazole (545 mg, 1.14 mmol, Eq: 1) was combined with MeOH (9 ml) to give a colorless solution. Under stirring and argon, 37% HCl in water (4.51 g, 3.76 ml, 45.8 mmol, Eq: 40) was added. The reaction mixture was stirred 30 min without heating, followed by 1 h at reflux. The reaction mixture was then cooled to RT and poured into ice water (35 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(2,4-difluorophenoxy)butan-1-ol as a colorless solid (360 mg, 90%). MS (ES+) m/z: 348.0 [(M+H)+].

Step 3: 4-(3-bromo-1H-1,2,4-triazol-5-yl)-4-(2,4-difluorophenoxy)butan-1-ol (355 mg, 1.02 mmol, Eq: 1) was combined with extra dry THF (10.5 ml) to give a colorless solution. Under stirring and argon, cyanomethylenetrimethylphosphorane solution in THF (0.5 M) (2.55 ml, 1.27 mmol, Eq: 1.25) was added dropwise over a period of 5 min. The reaction mixture was stirred 1 h at reflux. Then the reaction mixture was cooled to RT and extracted with EtOAc (80 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(2,4-difluorophenoxy)-5,6,7,8-tetrahydro-[1,2,4]triazolo[1,5-a]pyridine as a colorless oil (285 mg, 75%) MS (ES+) m/z: 330.0 [(M+H)+].

Intermediate 7-11

2-bromo-8-(3-chlorophenoxy)-5,6,7,8-tetrahydro-[1,2,4]triazolo[1,5-a]pyridine

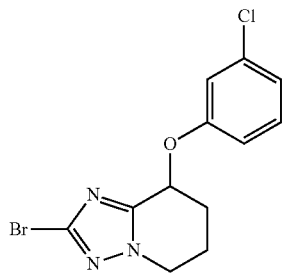 [SMILES: Clc1cccc(OC2CCCn3nc(Br)nc32)c1]

Step 1: 1-(3-bromo-1-(methoxymethyl)-1H-1,2,4-triazol-5-yl)-4-((tetrahydro-2H-pyran-2-yl)oxy)butan-1-ol (500 mg, 1.37 mmol, Eq: 1, described herein above), 3-chlorophenol (212 mg, 1.65 mmol, Eq: 1.2) and triphenylphosphine (450 mg, 1.72 mmol, Eq: 1.25) were combined with THF (25 ml) to give a colorless solution. The reaction mixture was cooled under stirring and argon, in an ice bath. DIAD (347 mg, 334 µl, 1.72 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3-chlorophenoxy)-4-((tetrahydro-2H-pyran-2-yl)oxy)butyl)-1-(methoxymethyl)-1H-1,2,4-triazole as a colorless oil (560 mg, 85%). MS (ES+) m/z: 474.0 [(M+H)+].

Step 2: 3-bromo-5-(1-(3-chlorophenoxy)-4-((tetrahydro-2H-pyran-2-yl)oxy)butyl)-1-(methoxymethyl)-1H-1,2,4-triazole (555 mg, 1.17 mmol, Eq: 1) was combined with MeOH (9 ml) to give a colorless solution. Under stirring and argon, 37% HCl in water (4.61 g, 3.84 ml, 46.8 mmol, Eq: 40) was added. The reaction mixture was stirred 30 min without heating, followed by 1 h at reflux. Then the reaction mixture was cooled to RT and poured into ice water (30 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(3-chlorophenoxy)butan-1-ol as a colorless viscous oil (375 mg, 92%). MS (ES+) m/z: 347.9 [(M+H)+].

Step 3: 4-(3-bromo-1H-1,2,4-triazol-5-yl)-4-(3-chlorophenoxy)butan-1-ol (370 mg, 1.07 mmol, Eq: 1) was combined with extra dry THF (11 ml) to give a colorless solution. Under stirring and argon, cyanomethylenetrimethylphosphorane solution in THF (0.5 M) (2.67 ml, 1.33 mmol, Eq: 1.25) was added dropwise over a period of 5 min. The reaction mixture was stirred 1 h at reflux. The reaction mixture was then cooled to RT and extracted with EtOAc (80 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(3-chlorophenoxy)-5,6,7,8-tetrahydro-[1,2,4]triazolo[1,5-a]pyridine as a colorless oil (263 mg, 75%) MS (ES+) m/z: 329.9 [(M+H)+].

Intermediate 7-12

2-bromo-8-(2-chlorophenoxy)-5,6,7,8-tetrahydro-[1,2,4]triazolo[1,5-a]pyridine

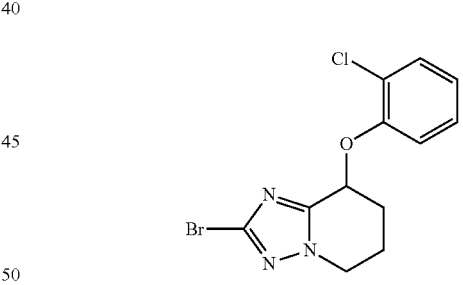

Step 1: 1-(3-bromo-1-(methoxymethyl)-1H-1,2,4-triazol-5-yl)-4-((tetrahydro-2H-pyran-2-yl)oxy)butan-1-ol (492 mg, 1.35 mmol, Eq: 1, described herein above), 2-chlorophenol (208 mg, 1.62 mmol, Eq: 1.2) and triphenylphosphine (443 mg, 1.69 mmol, Eq: 1.25) were combined with THF (25 ml) to give a colorless solution. The reaction mixture was cooled under stirring and argon, in an ice bath. DIAD (347 mg, 334 µl, 1.72 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(2-chlorophenoxy)-4-((tetrahydro-2H-pyran-2-yl)oxy)butyl)-1-(methoxymethyl)-1H-1,2,4-triazole as a colorless oil (560 mg, 85%). MS (ES+) m/z: 392.0 (−THP) [(M+H)+].

Step 2: 3-bromo-5-(1-(2-chlorophenoxy)-4-((tetrahydro-2H-pyran-2-yl)oxy)butyl)-1-(methoxymethyl)-1H-1,2,4-triazole (560 mg, 1.18 mmol, Eq: 1) was combined with MeOH (9 ml) to give a colorless solution. Under stirring and argon, 37% HCl in water (4.65 g, 3.87 ml, 47.2 mmol, Eq: 40) was added. The reaction mixture was stirred 30 min without heating, followed by 1 h at reflux. Cooled to RT and poured into ice water (30 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(2-chlorophenoxy)butan-1-ol as a white solid (362 mg, 88%). MS (ES+) m/z: 347.9 [(M+H)+].

Step 3: 4-(3-bromo-1H-1,2,4-triazol-5-yl)-4-(2-chlorophenoxy)butan-1-ol (360 mg, 1.04 mmol, Eq: 1) was combined with extra dry THF (11 ml) to give a colorless solution. Under stirring and argon, cyanomethylenetrimethylphosphorane solution in THF (0.5 M) (2.6 ml, 1.3 mmol, Eq: 1.25) was added dropwise over a period of 5 min. The reaction mixture was stirred 1 h at reflux. Then the reaction mixture was cooled to RT and extracted with EtOAc (80 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(2-chlorophenoxy)-5,6,7,8-tetrahydro-[1,2,4]triazolo[1,5-a]pyridine as a white solid (260 mg, 76%) MS (ES+) m/z: 329.9 [(M+H)+].

Intermediate 7-13

2-bromo-8-(4-chlorophenoxy)-5,6,7,8-tetrahydro-[1,2,4]triazolo[1,5-a]pyridine

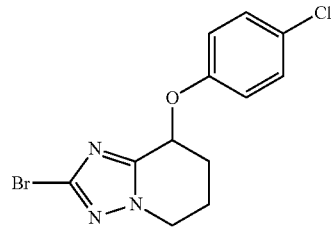 [SMILES: Clc1ccc(OC2CCCn3nc(Br)nc32)cc1]

Step 1: 1-(3-bromo-1-(methoxymethyl)-1H-1,2,4-triazol-5-yl)-4-((tetrahydro-2H-pyran-2-yl)oxy)butan-1-ol (500 mg, 1.37 mmol, Eq: 1, described herein above), 4-chlorophenol (212 mg, 1.65 mmol, Eq: 1.2) and triphenylphosphine (450 mg, 1.72 mmol, Eq: 1.25) were combined with THF (25 ml) to give a colorless solution. The reaction mixture was cooled under stirring and argon, in an ice bath. DIAD (347 mg, 334 µl, 1.72 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(4-chlorophenoxy)-4-((tetrahydro-2H-pyran-2-yl)oxy)butyl)-1-(methoxymethyl)-1H-1,2,4-triazole as a colorless oil (489 mg, 75%). MS (ES+) m/z: 474.9 [(M+H)+].

Step 2: 3-bromo-5-(1-(4-chlorophenoxy)-4-((tetrahydro-2H-pyran-2-yl)oxy)butyl)-1-(methoxymethyl)-1H-1,2,4-triazole (485 mg, 1.02 mmol, Eq: 1) was combined with MeOH (8 ml) to give a colorless solution. Under stirring and argon, 37% HCl in water (4.03 g, 3.36 ml, 40.9 mmol, Eq: 40) was added. The reaction mixture was stirred 30 min without heating, followed by 1 h at reflux. Then the reaction mixture was cooled to RT and poured into ice water (30 ml), neutralized with solid sodium bicarbonate and extracted with EtOAc (90 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(4-chlorophenoxy)butan-1-ol as a colorless viscous oil (320 mg, 90%). MS (ES+) m/z: 347.9 [(M+H)+].

Step 3: 4-(3-bromo-1H-1,2,4-triazol-5-yl)-4-(4-chlorophenoxy)butan-1-ol (310 mg, 894 µmol, Eq: 1) was combined with extra dry THF (11 ml) to give a colorless solution. Under stirring and argon, cyanomethylenetrimethylphosphorane solution in THF (0.5M) (2.24 ml, 1.12 mmol, Eq: 1.25) was added dropwise over a period of 5 min. The reaction mixture was stirred 1 h at reflux. Then the reaction mixture was cooled to RT and extracted with EtOAc (70 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(4-chlorophenoxy)-5,6,7,8-tetrahydro-[1,2,4]triazolo[1,5-a]pyridine as a white solid (182 mg, 61%) MS (ES+) m/z: 329.9 [(M+H)+].

Intermediate 7-14

2-bromo-8-(3,5-dichlorophenoxy)-5,6,7,8-tetrahydro-[1,2,4]triazolo[1,5-a]pyridine

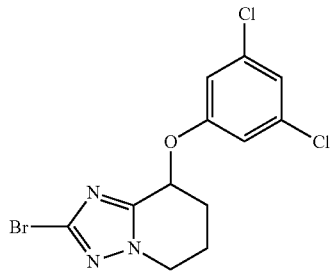 [SMILES: Clc1cc(Cl)cc(OC2CCCn3nc(Br)nc32)c1]

Step 1: 1-(3-bromo-1-(methoxymethyl)-1H-1,2,4-triazol-5-yl)-4-((tetrahydro-2H-pyran-2-yl)oxy)butan-1-ol (509 mg, 1.4 mmol, Eq: 1, described herein above), 3,5-dichlorophenol (273 mg, 1.68 mmol, Eq: 1.2) and triphenylphosphine (458 mg, 1.75 mmol, Eq: 1.25) were combined with THF (25 ml) to give a colorless solution. The reaction mixture was cooled under stirring and Argon, in an ice bath. DIAD (353 mg, 340 µl, 1.75 mmol, Eq: 1.25) was added dropwise over a period of 5 min. at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3,5-dichlorophenoxy)-4-((tetrahydro- 2H-pyran-2-yl)oxy)butyl)-1-(methoxymethyl)-1H-1,2,4-triazole as a colorless oil (670 mg, 94%). GCMS m/z: 423.9 (−THP) [(M+H)⁺].

Step 2: 3-bromo-5-(1-(3,5-dichlorophenoxy)-4-((tetrahydro-2H-pyran-2-yl)oxy)butyl)-1-(methoxymethyl)-1H-1,2,4-triazole (665 mg, 1.31 mmol, Eq: 1) was combined with MeOH (10 ml) to give a colorless solution. Under stirring and Argon, 37% HCl in water (5.15 g, 4.29 ml, 52.2 mmol, Eq: 40) was added (exothermic). The reaction mixture was stirred 30 min. without heating, followed by 1 h at reflux. The reaction mixture was then cooled to RT and poured into ice water (40 ml), neutralized with solid sodium bicarbonate and extracted with EtOAc (100 ml). The aqueous layer was back extracted with EtOAc (2×80 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(3,5-dichlorophenoxy)butan-1-ol as a white foam (435 mg, 87%). MS (ES+) m/z: 381.9 [(M+H)⁺].

Step 3: 4-(3-bromo-1H-1,2,4-triazol-5-yl)-4-(3,5-dichlorophenoxy)butan-1-ol (430 mg, 1.13 mmol, Eq: 1) was combined with extra dry THF (12 ml) to give a colorless solution. Under stirring and argon, cyanomethylenetrimethylphosphorane solution in THF (0.5 M) (2.82 ml, 1.41 mmol, Eq: 1.25) was added dropwise over a period of 5 min. The reaction mixture was stirred 1 h at reflux. Then the reaction mixture was cooled to RT and extracted with EtOAc (100 ml) and saturated sodium bicarbonate solution (15 ml). The aqueous layer was back extracted with EtOAc (2×50 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(3,5-dichlorophenoxy)-5,6,7,8-tetrahydro-[1,2,4]triazolo[1,5-a]pyridine as a white solid (285 mg, 69%) MS (ES+) m/z: 363.9 [(M+H)⁺].

Intermediate 7-15

2-bromo-8-(2,3-difluorophenoxy)-5,6,7,8-tetrahydro-[1,2,4]triazolo[1,5-a]pyridine

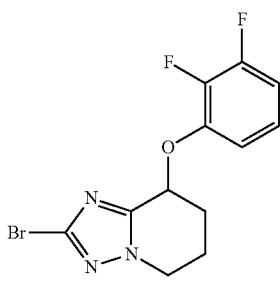 [SMILES: Fc1cccc(OC2CCCn3nc(Br)nc32)c1F]

Step 1: 1-(3-bromo-1-(methoxymethyl)-1H-1,2,4-triazol-5-yl)-4-((tetrahydro-2H-pyran-2-yl)oxy)butan-1-ol (498 mg, 1.37 mmol, Eq: 1, described herein above), 2,3-difluorophenol (213 mg, 1.64 mmol, Eq: 1.2) and triphenylphosphine (448 mg, 1.71 mmol, Eq: 1.25) were combined with THF (25 ml) to give a colorless solution. The reaction mixture was cooled under stirring and argon, in an ice bath. DIAD (346 mg, 332 μl, 1.71 mmol, Eq: 1.25) was added dropwise over a period of 5 min at max +3° C. The ice bath was removed and the reaction mixture was stirred 2 h at RT.

The reaction mixture was evaporated in vacuo and purified by ISCO chromatography (Hept: EtOAc 95:5 to 50:50) to afford 3-bromo-5-(1-(2,3-difluorophenoxy)-4-((tetrahydro-2H-pyran-2-yl)oxy)butyl)-1-(methoxymethyl)-1H-1,2,4-triazole as a colorless oil (560 mg, 86%). GCMS m/z: 392.0 (−THP) [(M+H)⁺].

Step 2: 3-bromo-5-(1-(2,3-difluorophenoxy)-4-((tetrahydro-2H-pyran-2-yl)oxy)butyl)-1-(methoxymethyl)-1H-1,2,4-triazole (555 mg, 1.17 mmol, Eq: 1) was combined with MeOH (9 ml) to give a colorless solution. Under stirring and argon, 37% HCl in water (4.59 g, 3.83 ml, 46.6 mmol, Eq: 40) was added. The reaction mixture was stirred 30 min. without heating, followed by 1 h at reflux. Then the reaction mixture was cooled to RT and poured into ice water (35 ml), neutralized with solid sodium bicarbonate and extracted with EtOAc (90 ml). The aqueous layer was back extracted with EtOAc (2×60 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(2,3-difluorophenoxy)butan-1-ol as a colorless viscous oil (375 mg, 92%). MS (ES+) m/z: 348.0 [(M+H)⁺].

Step 3: 4-(3-bromo-1H-1,2,4-triazol-5-yl)-4-(2,3-difluorophenoxy)butan-1-ol (372 mg, 1.07 mmol, Eq: 1) was combined with extra dry THF (11 ml) to give a colorless solution. Under stirring and argon, cyanomethylenetrimethylphosphorane solution in THF (0.5 M) (2.67 ml, 1.34 mmol, Eq: 1.25) was added dropwise over a period of 5 min. The reaction mixture was stirred 1.5 h at reflux. Then the reaction mixture was cooled to RT and extracted with EtOAc (80 ml) and saturated sodium bicarbonate solution (15 ml). The aqueous layer was back extracted with EtOAc (2×60 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(2,3-difluorophenoxy)-5,6,7,8-tetrahydro-[1,2,4]triazolo[1,5-a]pyridine as a white solid (255 mg, 72%). MS (ES+) m/z: 330.0 [(M+H)⁺].

Intermediate 7-16

2-bromo-8-(3,4-difluorophenoxy)-5,6,7,8-tetrahydro-[1,2,4]triazolo[1,5-a]pyridine

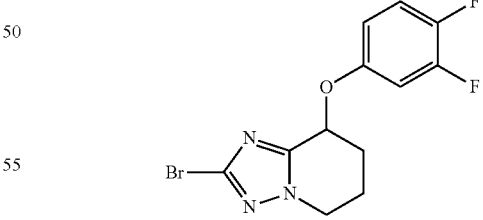

Step 1: 1-(3-bromo-1-(methoxymethyl)-1H-1,2,4-triazol-5-yl)-4-((tetrahydro-2H-pyran-2-yl)oxy)butan-1-ol (500 mg, 1.37 mmol, Eq: 1, described herein above), 3,4-difluorophenol (214 mg, 1.65 mmol, Eq: 1.2) and triphenylphosphine (450 mg, 1.72 mmol, Eq: 1.25) were combined with THF (25 ml) to give a colorless solution. The reaction mixture was cooled under stirring and argon, in an ice bath. DIAD (347 mg, 334 μl, 1.72 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3,4-difluorophenoxy)-4-((tetrahydro-2H-pyran-2-yl)oxy)butyl)-1-(methoxymethyl)-1H-1,2,4-triazole as a colorless oil (550 mg, 84%). MS (ES+) m/z: 392.0 (-THP) [(M+H)⁺].

Step 2: 3-bromo-5-(1-(3,4-difluorophenoxy)-4-((tetrahydro-2H-pyran-2-yl)oxy)butyl)-1-(methoxymethyl)-1H-1,2,4-triazole (550 mg, 1.15 mmol, Eq: 1) was combined with MeOH (9 ml) to give a colorless solution. Under stirring and argon, 37% HCl in water (4.55 g, 3.79 ml, 46.2 mmol, Eq: 40) was added. The reaction mixture was stirred 30 min without heating, followed by 1 h at reflux. Then the reaction mixture was cooled to RT and poured into ice water (35 ml), neutralized with solid sodium bicarbonate and extracted with EtOAc (100 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 90:10 to 0:100) to afford 4-(3-bromo-1H-1,2,4-triazol-5-yl)-4-(3,4-difluorophenoxy)butan-1-ol as a colorless viscous oil (385 mg, 95%). MS (ES+) m/z: 348.0 [(M+H)⁺].

Step 3: 4-(3-bromo-1H-1,2,4-triazol-5-yl)-4-(3,4-difluorophenoxy)butan-1-ol (380 mg, 1.09 mmol, Eq: 1) was combined with extra dry THF (12 ml) to give a colorless solution. Under stirring and argon, cyanomethylenetrimethylphosphorane solution in THF (0.5 M) (2.73 ml, 1.36 mmol, Eq: 1.25) was added dropwise over a period of 5 min. The reaction mixture was stirred 1.5 h at reflux. Then the reaction mixture was cooled to RT and extracted with EtOAc (80 ml) and saturated sodium bicarbonate solution (15 ml). The aqueous layer was back extracted with EtOAc (2×60 ml). The organic layers were washed with brine (15 ml). The organic layers were combined, dried over sodium sulfate, filtered and evaporated in vacuo. The residue was purified by ISCO chromatography (Hept: EtOAc 95:5 to 0:100) to afford 2-bromo-8-(3,4-difluorophenoxy)-5,6,7,8-tetrahydro-[1,2,4]triazolo[1,5-a]pyridine as a colorless oil (292 mg, 81%). MS (ES+) m/z: 330.0 [(M+H)⁺].

1.2.3) Intermediates of Type 7, with m=3

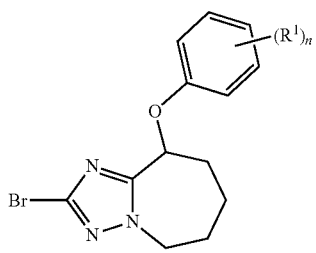

Intermediate 7-17

2-bromo-9-(4-fluorophenoxy)-6,7,8,9-tetrahydro-5H-[1,2,4]triazolo[1,5-a]azepine

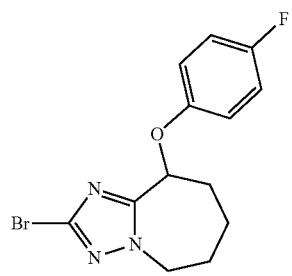 [SMILES: Fc1ccc(OC2CCCCn3nc(Br)nc32)cc1]

Step 1: 3,5-dibromo-1-(methoxymethyl)-1H-1,2,4-triazole (10.2 g, 37.7 mmol, Eq: 1, described herein above) was combined with THF (90 ml) to give a colorless solution. The mixture was then cooled in a dry ice/acetone bath to −75° C. n-butyllithium 1.6 M in hexane (24.9 ml, 39.9 mmol, Eq: 1.06) was added dropwise over a period of 20 min. The yellow solution was stirred 45 min. at −75° C. Then a solution of 5-((tetrahydro-2H-pyran-2-yl)oxy)pentanal (8.41 g, 45.2 mmol, Eq: 1.2) in THF (90 ml) was added dropwise over a period of 30 min. Then the mixture was stirred 45 min at −75° C. The dry ice/acetone bath was removed and the reaction mixture let to warm over 1 h to ca. 15° C. The reaction mixture was quenched with 190 ml of saturated NH₄Cl-solution, followed by 190 ml water and 250 ml EtOAc. The mixture was stirred 5 min. The layers were separated. The aqueous layer was back extracted with EtOAc (2×250 ml). The organic layers were washed with brine (200 ml). The organic layers were combined, dried over sodium sulfate, filtered and evaporated in vacuo. The residue was purified by ISCO chromatography (Hept: EtOAc 80:20 to 20:80) to afford 1-(3-bromo-1-(methoxymethyl)-1H-1,2,4-triazol-5-yl)-5-((tetrahydro-2H-pyran-2-yl)oxy)pentan-1-ol as a light yellow oil (11.4 g 80%). MS (ES+) m/z: 378.1/380.1 [(M+H)⁺].

Step 2: 1-(3-bromo-1-(methoxymethyl)-1H-1,2,4-triazol-5-yl)-5-((tetrahydro-2H-pyran-2-yl)oxy)pentan-1-ol (500 mg, 1.32 mmol, Eq: 1), 4-fluorophenol (178 mg, 1.59 mmol, Eq: 1.2) and triphenylphosphine (433 mg, 1.65 mmol, Eq: 1.25) were combined with THF (25 ml) to give a colorless solution. The reaction mixture was cooled under stirring and argon in an ice bath. DIAD (334 mg, 321 µl, 1.65 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(4-fluorophenoxy)-5-((tetrahydro-2H-pyran-2-yl)oxy)pentyl)-1-(methoxymethyl)-1H-1,2,4-triazole as a light yellow oil (485 mg, 77%). MS (ES+) m/z: 474.1 [(M+H)⁺].

Step 3: 3-bromo-5-(1-(4-fluorophenoxy)-5-((tetrahydro-2H-pyran-2-yl)oxy)pentyl)-1-(methoxymethyl)-1H-1,2,4-triazole (480 mg, 1.02 mmol, Eq: 1) was combined with MeOH (8 ml) to give a colorless solution. Under stirring and argon, 37% HCl in water (4.01 g, 3.34 ml, 40.6 mmol, Eq: 40) was added. The reaction mixture was stirred 30 min without heating, followed by 1 h at reflux. Then the reaction mixture was cooled to RT and poured into ice water (30 ml), neutralized with solid sodium bicarbonate and extracted with EtOAc (100 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 90:10 to 0:100) to afford 5-(3-bromo-1H-1,2,4-triazol-5-yl)-5-(4-fluorophenoxy)pentan-1-ol (325 mg, 944 µmol, Eq: 1) as a colorless viscous oil (330 mg, 94%). MS (ES+) m/z: 346.0 [(M+H)$^+$].

Step 4: 5-(3-bromo-1H-1,2,4-triazol-5-yl)-5-(4-fluorophenoxy)pentan-1-ol (325 mg, 944 µmol, Eq: 1) was combined with extra dry THF (10 ml) to give a colorless solution. Under stirring and argon, cyanomethylenetrimethylphosphorane solution in THF (0.5 M) (2.36 ml, 1.18 mmol, Eq: 1.25) was added dropwise over a period of 5 min. The reaction mixture was stirred 1.5 h at reflux. Then the reaction mixture was cooled to RT and extracted with EtOAc (60 ml) and saturated sodium bicarbonate solution (10 ml). The aqueous layer was back extracted with EtOAc (2×40 ml). The organic layers were combined, dried over sodium sulfate, filtered and evaporated in vacuo. The residue was purified by ISCO chromatography (Hept: EtOAc 95:5 to 50:50) to afford 2-bromo-9-(4-fluorophenoxy)-6,7,8,9-tetrahydro-5H-[1,2,4]triazolo[1,5-a]azepine as a colorless viscous oil (308 mg, 58%). MS (ES+) m/z: 326.0 [(M+H)$^+$].

Intermediate 7-18

2-bromo-9-(2,3,4-trifluorophenoxy)-6,7,8,9-tetrahydro-5H-[1,2,4]triazolo[1,5-a]azepine

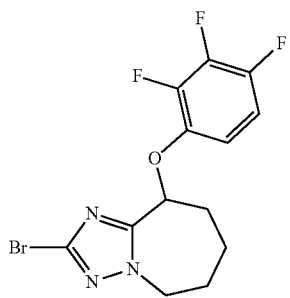 [SMILES: Fc1ccc(OC2CCCCn3nc(Br)nc32)c(F)c1F]

Step 1: 1-(3-bromo-1-(methoxymethyl)-1H-1,2,4-triazol-5-yl)-5-((tetrahydro-2H-pyran-2-yl)oxy)pentan-1-ol (500 mg, 1.32 mmol, Eq: 1, described herein above), 2,3,4-trifluorophenol (235 mg, 1.59 mmol, Eq: 1.2) and triphenylphosphine (433 mg, 1.65 mmol, Eq: 1.25) were combined with THF (25 ml) to give a colorless solution. The reaction mixture was cooled under stirring and argon, in an ice bath. DIAD (334 mg, 321 µl, 1.65 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-1-(methoxymethyl)-5-(5-((tetrahydro-2H-pyran-2-yl)oxy)-1-(2,3,4-trifluorophenoxy)pentyl)-1H-1,2,4-triazole as a light yellow oil (555 mg, 82%). MS (ES+) m/z: 508.1 [(M+H)$^+$].

Step 2: 3-bromo-1-(methoxymethyl)-5-(5-((tetrahydro-2H-pyran-2-yl)oxy)-1-(2,3,4-trifluorophenoxy)pentyl)-1H-1,2,4-triazole (550 mg, 1.08 mmol, Eq: 1) was combined with MeOH (8 ml) to give a colorless solution. Under stirring and argon, 37% HCl in water (4.26 g, 3.55 ml, 43.3 mmol, Eq: 40) was added (exothermic). The reaction mixture was stirred 30 min without heating, followed by 1 h at reflux. Then the reaction was cooled to RT and poured into ice water (30 ml), neutralized with solid sodium bicarbonate and extracted with EtOAc (100 ml).

The aqueous layer was back extracted with EtOAc (2×70 ml). The organic layers were combined, dried over sodium sulfate, filtered and evaporated in vacuo. The residue was purified by ISCO chromatography (Hept: EtOAc 80:20 to 0:100) to afford 5-(3-bromo-1H-1,2,4-triazol-5-yl)-5-(2,3,4-trifluorophenoxy)pentan-1-ol as a colorless oil (390 mg, 94%). MS (ES+) m/z: 380.0 [(M+H)$^+$].

Step 3: 5-(3-bromo-1H-1,2,4-triazol-5-yl)-5-(2,3,4-trifluorophenoxy)pentan-1-ol (385 mg, 1.01 mmol, Eq: 1) was combined with extra dry THF (10 ml) to give a colorless solution. Under stirring and argon, cyanomethylenetrimethylphosphorane solution in THF (0.5 M) (2.53 ml, 1.27 mmol, Eq: 1.25) was added dropwise over a period of 5 min. The reaction mixture was stirred 1.5 h at reflux. Then the reaction mixture was cooled to RT and extracted with EtOAc (60 ml) and saturated sodium bicarbonate solution (10 ml). The aqueous layer was back extracted with EtOAc (2×40 ml). The organic layers were combined, dried over sodium sulfate, filtered and evaporated in vacuo. The residue was purified by ISCO chromatography (Hept: EtOAc 95:5 to 50:50) to afford 2-bromo-9-(2,3,4-fluorophenoxy)-6,7,8,9-tetrahydro-5H-[1,2,4]triazolo[1,5-a]azepine as a white solid (225 mg, 61%). MS (ES+) m/z: 362.0 [(M+H)$^+$].

Intermediate 7-19

2-bromo-9-(3-chloro-5-fluorophenoxy)-6,7,8,9-tetrahydro-5H-[1,2,4]triazolo[1,5-a]azepine

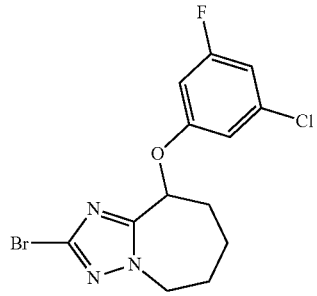 [SMILES: Fc1cc(Cl)cc(OC2CCCCn3nc(Br)nc32)c1]

Step 1: 1-(3-bromo-1-(methoxymethyl)-1H-1,2,4-triazol-5-yl)-5-((tetrahydro-2H-pyran-2-yl)oxy)pentan-1-ol (500 mg, 1.32 mmol, Eq: 1, described herein above), 3-chloro-5-fluorophenol (232 mg, 1.59 mmol, Eq: 1.2) and triphenylphosphine (433 mg, 1.65 mmol, Eq: 1.25) were combined with THF (25 ml) to give a colorless solution. The reaction mixture was cooled under stirring and argon, in an ice bath. DIAD (334 mg, 321 µl, 1.65 mmol, Eq: 1.25) was added dropwise over a period of 5 min at max +3° C. The ice bath was removed and the reaction mixture was stirred 2 h at RT. The reaction mixture was evaporated in vacuo and purified by ISCO chromatography (Hept: EtOAc 95:5 to 50:50) to afford 3-bromo-5-(1-(3-chloro-5-fluorophenoxy)-5-((tetrahydro-2H-pyran-2-yl)oxy)pentyl)-1-(methoxymethyl)-1H-1,2,4-triazole as a colorless oil (565 mg, 84%). MS (ES+) m/z: 506.0 [(M+H)$^+$].

Step 2: 3-bromo-5-(1-(3-chloro-5-fluorophenoxy)-5-((tetrahydro-2H-pyran-2-yl)oxy)pentyl)-1-(methoxymethyl)-1H-1,2,4-triazole (560 mg, 1.1 mmol, Eq: 1) was combined with MeOH (8 ml) to give a colorless solution. Under stirring and Argon 37% HCl in water (4.36 g, 3.63 ml, 44.2 mmol, Eq: 40) was added. The reaction mixture was stirred 30 min without heating, followed by 1 h at reflux. Cooled to RT and poured into ice water (30 ml), neutralized with solid sodium bicarbonate and extracted with EtOAc (100 ml). The aqueous layer was back extracted with EtOAc (2×70 ml). The organic layers were combined, dried over sodium sulfate, filtered and evaporated in vacuo. The residue was purified by ISCO chromatography (Hept: EtOAc 80:20 to 0:100) to afford 5-(3-bromo-1H-1,2,4-triazol-5-yl)-5-(3-chloro-5-fluorophenoxy)pentan-1-ol as a colorless viscous oil (350 mg, 83%). MS (ES+) m/z: 379.9 [(M+H)$^+$].

Step 3: 5-(3-bromo-1H-1,2,4-triazol-5-yl)-5-(3-chloro-5-fluorophenoxy)pentan-1-ol (380 mg, 1 mmol, Eq: 1) was combined with extra dry THF (10 ml) to give a colorless solution. Under stirring and argon, cyanomethylenetrimethylphosphorane solution in THF (0.5 M) (2.51 ml, 1.25 mmol, Eq: 1.25) was added dropwise over a period of 5 min. The reaction mixture was stirred 1.5 h at reflux. Then the reaction mixture was cooled to RT and extracted with EtOAc (60 ml) and saturated sodium bicarbonate solution (10 ml). The aqueous layer was back extracted with EtOAc (2×40 ml). The organic layers were combined, dried over sodium sulfate, filtered and evaporated in vacuo. The residue was purified by ISCO chromatography (Hept: EtOAc 95:5 to 50:50) to afford 2-bromo-9-(3-chloro-5-fluorophenoxy)-6,7,8,9-tetrahydro-5H-[1,2,4]triazolo[1,5-a]azepine as a colorless oil (218 mg, 60%). MS (ES+) m/z: 361.9 [(M+H)$^+$].

1.2.4) Intermediates of Type 8

Intermediate 8-1

(1R,5S,8S)-3-(6-methylpyrimidin-4-yl)-3-azabicyclo[3.2.1]octan-8-amine

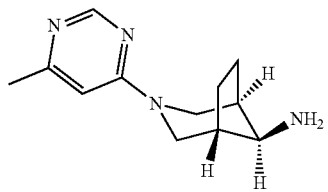 [SMILES: Cc1cc(N2C[C@H]3CC[C@@H](C2)[C@@H]3N)ncn1]

Step 1: In a sealed tube tert-butyl N-[(1R,5S,8S)-3-azabicyclo[3.2.1]octan-8-yl]carbamate (500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuo. The residue was diluted with 20 mL of CH$_2$Cl$_2$ and 20 mL of water. The organic phase was extracted with CH$_2$Cl$_2$ (3×20 mL), dried over MgSO$_4$ and concentrated in vacuum. The crude material was purified by flash chromatography (0% to 100% EtOAc in heptane) to afford tert-butyl N-[(1R,5S,8S)-3-(6-methylpyrimidin-4-yl)-3-azabicyclo[3.2.1]octan-8-yl]carbamate as a yellow solid (496 mg, 71% yield). MS (ES+) m/z: 319.2 [(M+H)$^+$].

Step 2: To a light yellow solution of tert-butyl N-[(1R,5S,8S)-3-(6-methylpyrimidin-4-yl)-3-azabicyclo[3.2.1]octan-8-yl]carbamate (260 mg, 817 μmol) in CH$_2$Cl$_2$ (8 mL) was added TFA (931 mg, 629 μl, 8.17 mmol). The reaction mixture was stirred at room temperature overnight and concentrated in vacuum. The crude material was purified by Ion-exchange column (Si-SCX-2, 10 g, washed with MeOH and liberated with MeOH (NH$_3$ 2M)) to afford (1R,5S,8S)-3-(6-methylpyrimidin-4-yl)-3-azabicyclo[3.2.1]octan-8-amine 8-1 (195 mg, 804 μmol, 98.5% yield) that was used in the next step without further purification. MS (ES+) m/z: 219.2 [(M+H)$^+$].

Intermediate 8-2

(1R,5S,8S)-3-(6-methoxypyridazin-4-yl)-3-azabicyclo[3.2.1]octan-8-amine

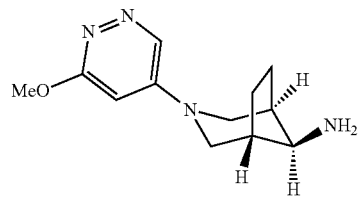 [SMILES: COc1cc(N2C[C@H]3CC[C@@H](C2)[C@@H]3N)cnn1]

Step 1: In analogy to the preparation of the intermediate 8-1 (step 1) from tert-butyl N-[(1R,5S,8S)-3-azabicyclo[3.2.1]octan-8-yl]carbamate (2.00 g, 8.84 mmol) and 3,5-dichloropyridazine (2.0 g, 13.4 mmol) in a sealed tube at 90° C. using EtOH as solvent in the presence of Et3N (3.63 g, 5.0 mL, 35.9 mmol), tert-butyl N-[(1R,5S,8S)-3-(6-chloropyridazin-4-yl)-3-azabicyclo[3.2.1]octan-8-yl]carbamate (1.71 g, 54%) was obtained as a white solid. MS (ES+) m/z: 339.2 [(M+H)$^+$].

Step 2: To a solution of tert-butyl N-[(1R,5S,8S)-3-(6-chloropyridazin-4-yl)-3-azabicyclo[3.2.1]octan-8-yl]carbamate (963 mg, 2.70 mmol) in MeOH (22 mL) in a sealed tube was added a methanol solution of NaOMe (25%, 1.9 mL, 8.3 mmol). The reaction mixture was heated at 85° C. overnight. The reaction mixture was adsorbed on Isolute HM-N and a column chromatography gave tert-butyl N-[(1R,5S,8S)-3-(6-methoxypyridazin-4-yl)-3-azabicyclo[3.2.1]octan-8-yl]carbamate (362 mg, 38%) as a white solid. MS (ES+) m/z: 335.2 [(M+H)$^+$].

Step 3: In analogy to the preparation of intermediate 8-1 (step 2) from tert-butyl N-[(1R,5S,8S)-3-(6-methoxypyridazin-4-yl)-3-azabicyclo[3.2.1]octan-8-yl]carbamate (0.93 g, 2.72 mmol) in CH$_2$Cl$_2$ in the presence of TFA (1.12 g, 0.76 mL, 9.86 mmol), (1R,5S,8S)-3-(6-methoxypyridazin-4-yl)-3-azabicyclo[3.2.1]octan-8-amine 8-2 (225 mg, 96%) was obtained as a white solid and used directly in the next step without further purification. MS (ES+) m/z: 235.2 [(M+H)$^+$].

Intermediate 8-3

(1R,5S,8S)-3-(6-methylpyridazin-4-yl)-3-azabicyclo[3.2.1]octan-8-amine

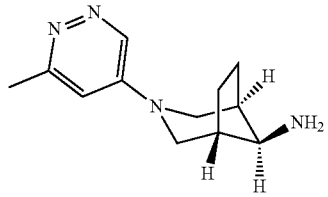 [SMILES: Cc1cc(N2C[C@H]3CC[C@@H](C2)[C@@H]3N)cnn1]

In a similar manner as for the intermediates 8-1 and 8-2, the title compound 8-3 was produced starting from tert-butyl N-[(1R,5S,8S)-3-azabicyclo[3.2.1]octan-8-yl]carbamate and 5-chloro-3-methyl-pyridazine as a white solid. MS (ES+) m/z: 219.3 [(M+H)+].

1.3) General Procedure 1: Buchwald Coupling Reaction

In a sealed tube, to a solution of an intermediate 7 (0.25 mmol) in 2-Me-THF (7 ml) was added 1.0 equivalent of an intermediate 8. The reaction mixture was degased and NaOtBu (1.5 eq.) was added at RT and the stirring continued for 10 minutes before tBu-Xphos (0.06 eq.) and Pd$_2$(dba)$_3$ (0.03 eq.) were added. The reaction mixture was heated at 70-80° C. until completion of the reaction (usually between 1 and 3 hours) and concentrated under vacuum. A purification was done either by flash column chromatography or reverse phase preparative HPLC to afford the desired product of formula (I).

Following examples 1 to 64 are single enantiomers but the absolute configuration was not determined. The enantiomers are mentioned in the examples in the order in which they were eluted from the column.

Examples 1 and 2

(R)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine and (S)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine

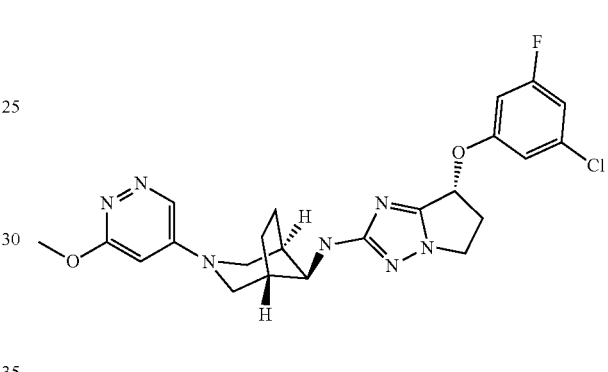

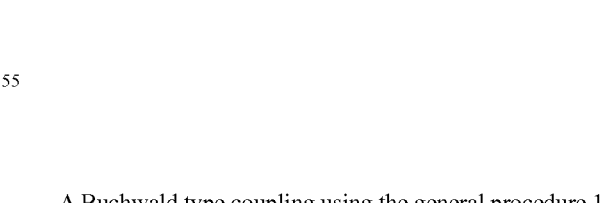

A Buchwald type coupling using the general procedure 1, between 2-bromo-7-(3,5-difluorophenoxy)-6,7-dihydro-5H-pyrrolo[1,2-b][1,2,4]triazole 7-1 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solid (example 1): 27 mg, MS (ES+) m/z: 470.2 [(M+H)+] and (example 2): 28 mg, MS (ES+) m/z: 470.2 [(M+H)+].

Examples 3 and 4

(R)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine and (S)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine

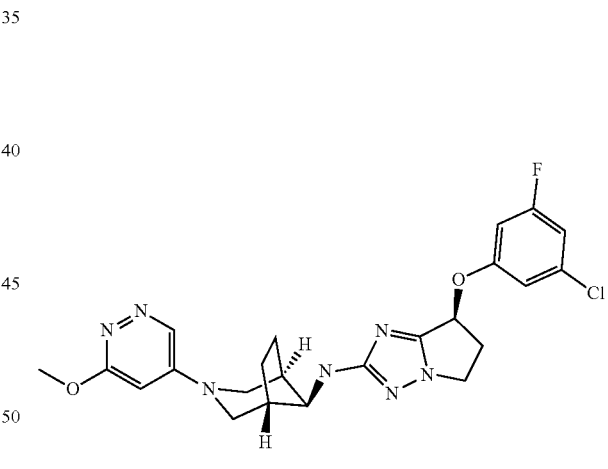

A Buchwald type coupling using the general procedure 1, between 2-bromo-7-(3-chloro-5-fluorophenoxy)-6,7-dihydro-5H-pyrrolo[1,2-b][1,2,4]triazole 7-2 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solids (example 3): 18 mg, MS (ES+) m/z: 486.1 [(M+H)+] and (example 4): 20 mg, MS (ES+) m/z: 486.1 [(M+H)+].

Examples 5 and 6

(R)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine and (S)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine

Examples 7 and 8

(R)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine and (S)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine

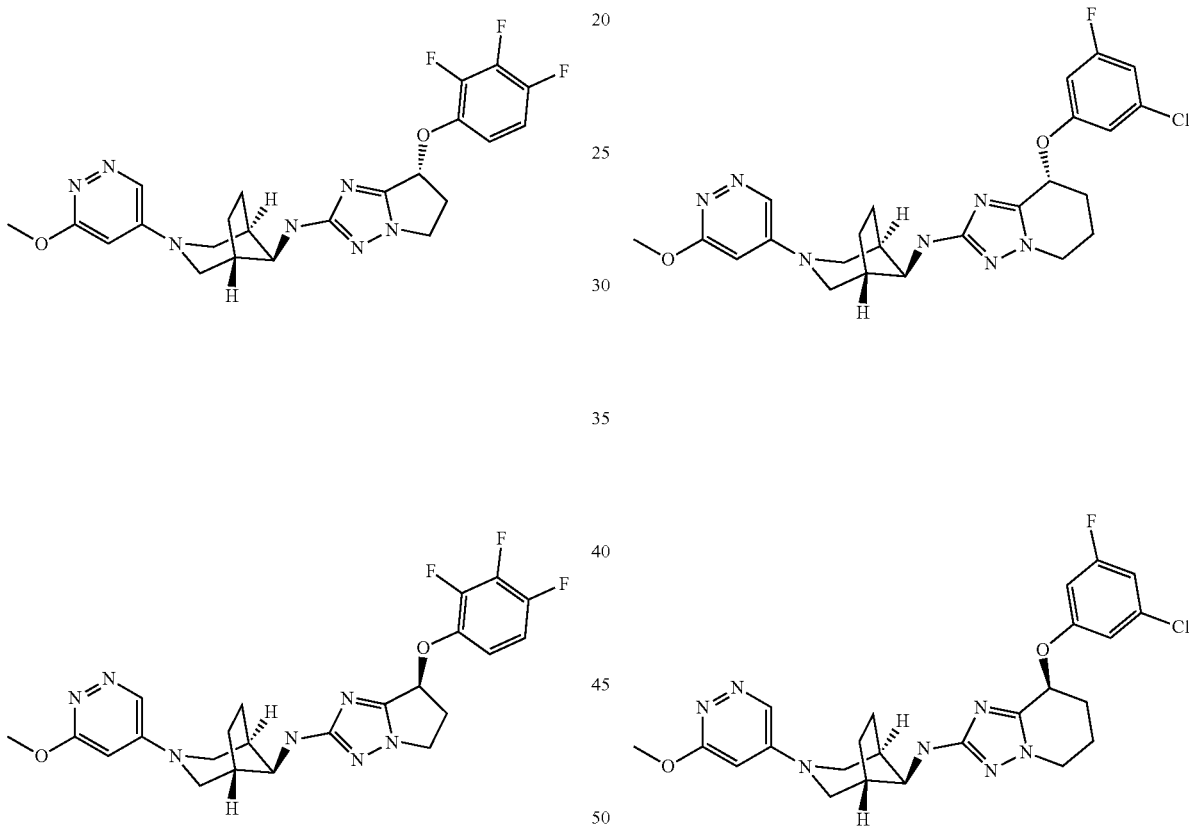

A Buchwald type coupling using the general procedure 1, between 2-bromo-7-(2,3,4-trifluorophenoxy)-6,7-dihydro-5H-pyrrolo[1,2-b][1,2,4]triazole 7-3 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solids (example 5): 20 mg, MS (ES+) m/z: 488.2 [(M+H)$^+$] and (example 6): 20 mg, MS (ES+) m/z: 488.2 [(M+H)$^+$].

A Buchwald type coupling using the general procedure 1, between 2-bromo-8-(3-chloro-5-fluorophenoxy)-5,6,7,8-tetrahydro-[1,2,4]triazolo[1,5-a]pyridine 7-7 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solids (example 7): 34 mg, MS (ES+) m/z: 500.1 [(M+H)$^+$] and (example 8): 31 mg, MS (ES+) m/z: 500.1 [(M+H)$^+$].

Examples 9 and 10

(R)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine and (S)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine

Examples 11 and 12

(R)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine and (S)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine

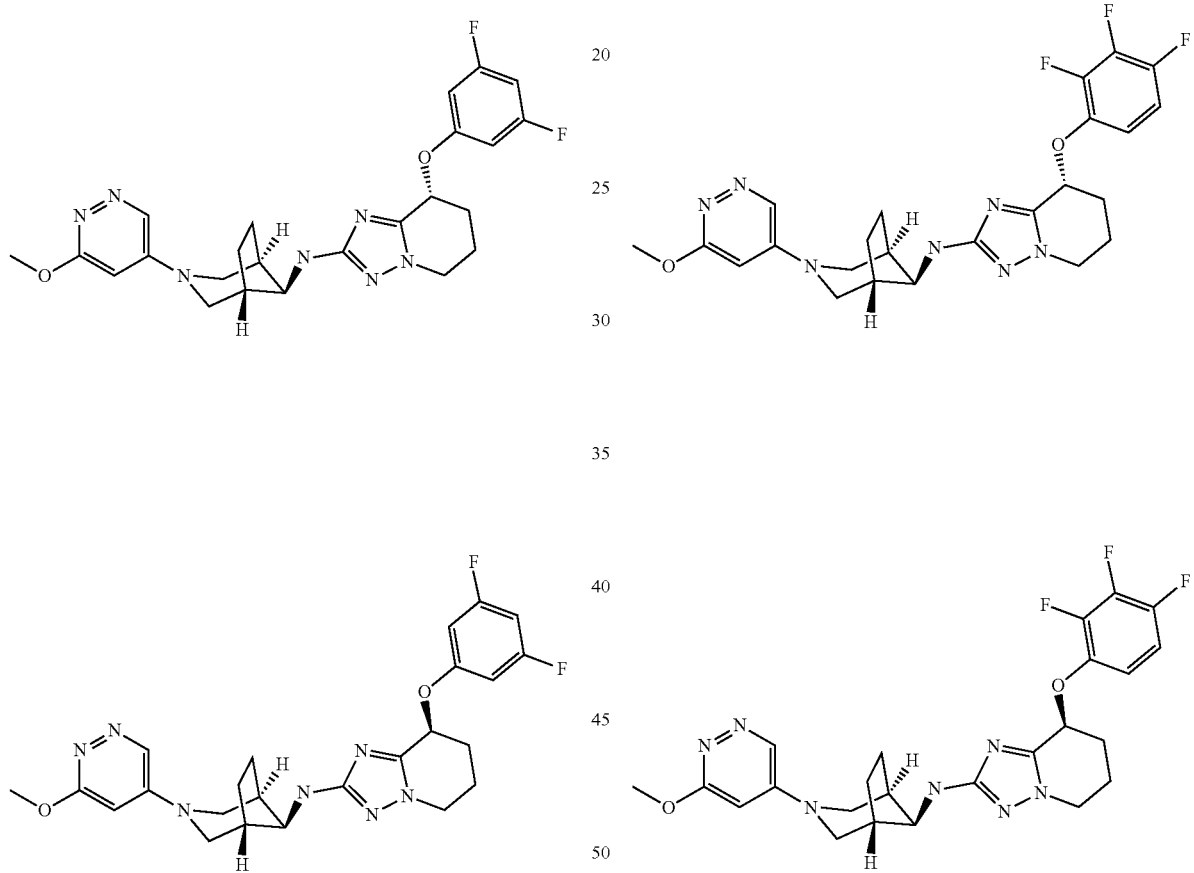

A Buchwald type coupling using the general procedure 1, between 2-bromo-8-(3,5-difluorophenoxy)-5,6,7,8-tetrahydro-[1,2,4]triazolo[1,5-a]pyridine 7-8 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solids (example 9): 37 mg, MS (ES+) m/z: 484.2 [(M+H)$^+$] and (example 10): 36 mg, MS (ES+) m/z: 484.2 [(M+H)$^+$].

A Buchwald type coupling using the general procedure 1, between 2-bromo-8-(2,3,4-trifluorophenoxy)-5,6,7,8-tetrahydro-[1,2,4]triazolo[1,5-a]pyridine 7-9 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solids (example 11): 42 mg, MS (ES+) m/z: 502.2 [(M+H)$^+$] and (example 12): 41 mg, MS (ES+) m/z: 502.2 [(M+H)$^+$].

Examples 13 and 14

(R)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine and (S)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine

Examples 15 and 16

(R)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine and (S)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine

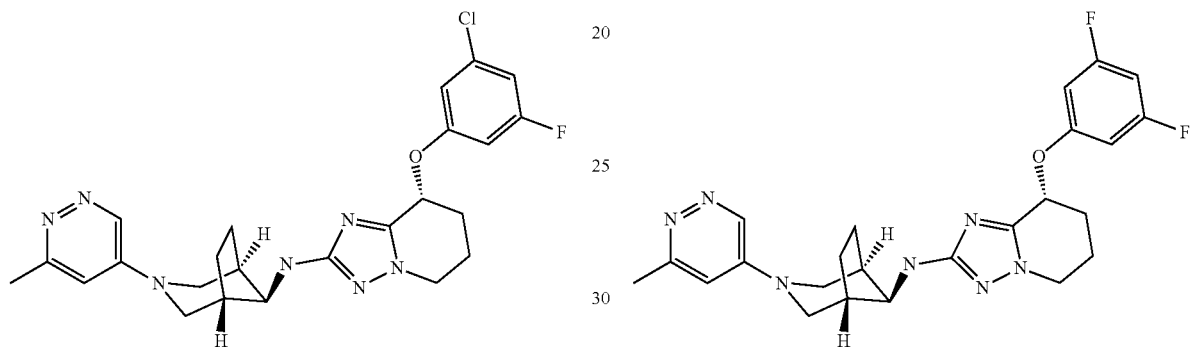

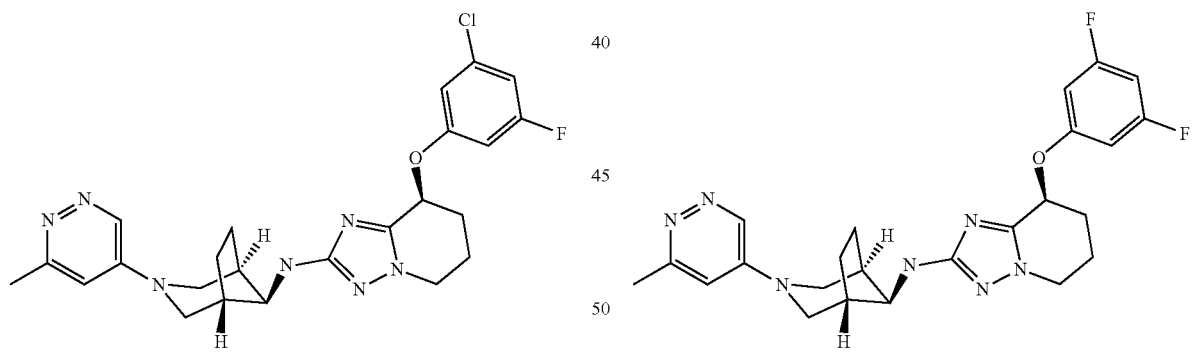

A Buchwald type coupling using the general procedure 1, between 2-bromo-8-(3-chloro-5-fluorophenoxy)-5,6,7,8-tetrahydro-[1,2,4]triazolo[1,5-a]pyridine 7-7 and (1R,5S,8S)-3-(6-methylpyridazin-4-yl)-3-azabicyclo[3.2.1]octan-8-amine 8-3, followed by a separation of the enantiomeres by preparative chiral HPLC afforded the title products as white solids (example 13): 32 mg, MS (ES+) m/z: 484.2 [(M+H)$^+$] and (example 14): 33 mg, MS (ES+) m/z: 484.2 [(M+H)$^+$].

A Buchwald type coupling using the general procedure 1, between 2-bromo-8-(3,5-difluorophenoxy)-5,6,7,8-tetrahydro-[1,2,4]triazolo[1,5-a]pyridine 7-8 and (1R,5S,8S)-3-(6-methylpyridazin-4-yl)-3-azabicyclo[3.2.1]octan-8-amine 8-3, followed by a separation of the enantiomeres by preparative chiral HPLC afforded the title products as white solids (example 15): 29 mg, MS (ES+) m/z: 468.2 [(M+H)$^+$] and (example 16): 25 mg, MS (ES+) m/z: 468.2 [(M+H)$^+$].

Examples 17 and 18

(R)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine and (S)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine

Examples 19 and 20

(R)-8-(2,4-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine and (S)-8-(2,4-difluorophenoxy)-N-((1R,5S,8S)-3-(6-methoxypyridazin-4-yl)-3-azabicyclo[3.2.1]octan-8-yl)-5,6,7,8-tetrahydro-[1,2,4]triazolo[1,5-a]pyridin-2-amine

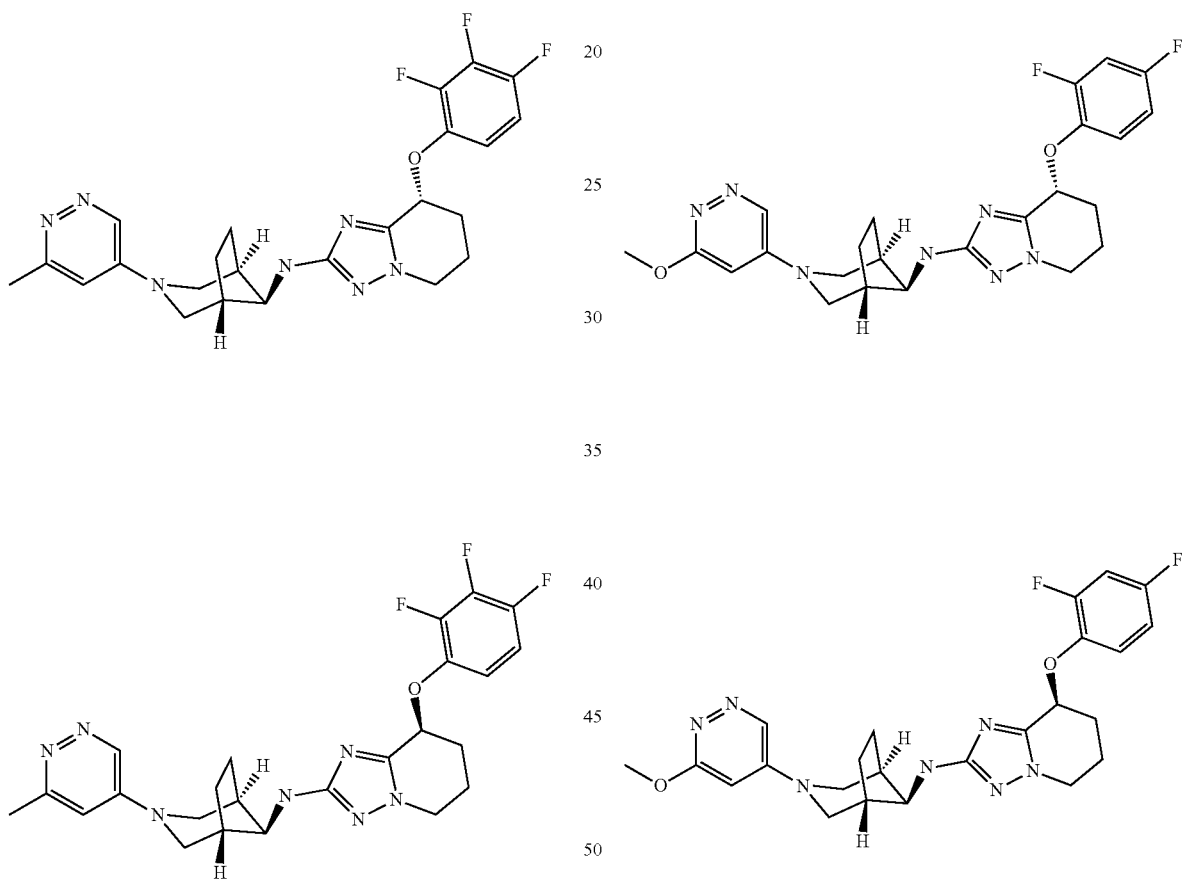

A Buchwald type coupling using the general procedure 1, between 2-bromo-8-(2,3,4-trifluorophenoxy)-5,6,7,8-tetrahydro-[1,2,4]triazolo[1,5-a]pyridine 7-9 and (1R,5S,8S)-3-(6-methylpyridazin-4-yl)-3-azabicyclo[3.2.1]octan-8-amine 8-3, followed by a separation of the enantiomeres by preparative chiral HPLC afforded the title products as white solids (example 17): 26 mg, MS (ES+) m/z: 486.2 [(M+H)$^+$] and (example 18): 26 mg, MS (ES+) m/z: 486.2 [(M+H)$^+$].

A Buchwald type coupling using the general procedure 1, between 2-bromo-8-(2,4-difluorophenoxy)-5,6,7,8-tetrahydro-[1,2,4]triazolo[1,5-a]pyridine 7-10 and (1R,5S,8S)-3-(6-methoxypyridazin-4-yl)-3-azabicyclo[3.2.1]octan-8-amine 8-2, followed by a separation of the enantiomers by preparative chiral HPLC afforded the title products as white solids (example 19): 28 mg, MS (ES+) m/z: 484.2 [(M+H)$^+$] and (example 20): 28 mg, MS (ES+) m/z: 484.2 [(M+H)$^+$].

Examples 21 and 22

(R)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine and (S)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine

Examples 23 and 24

(R)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine and (S)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine

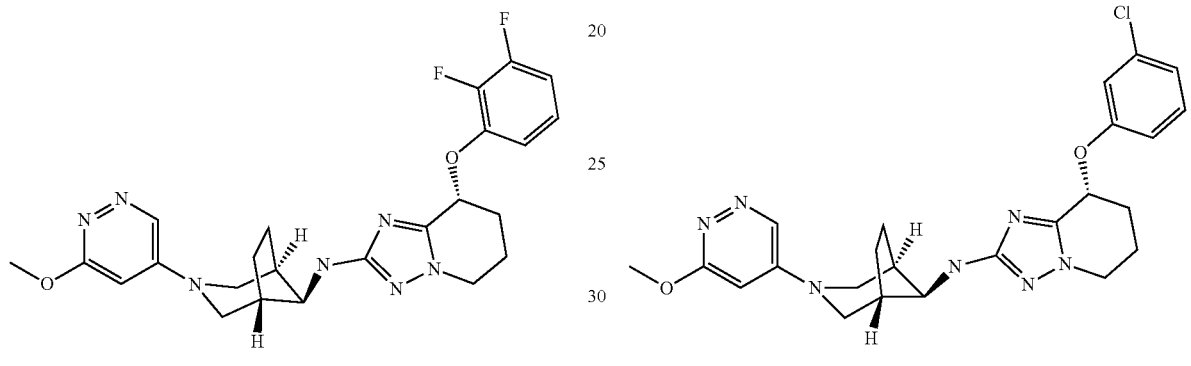

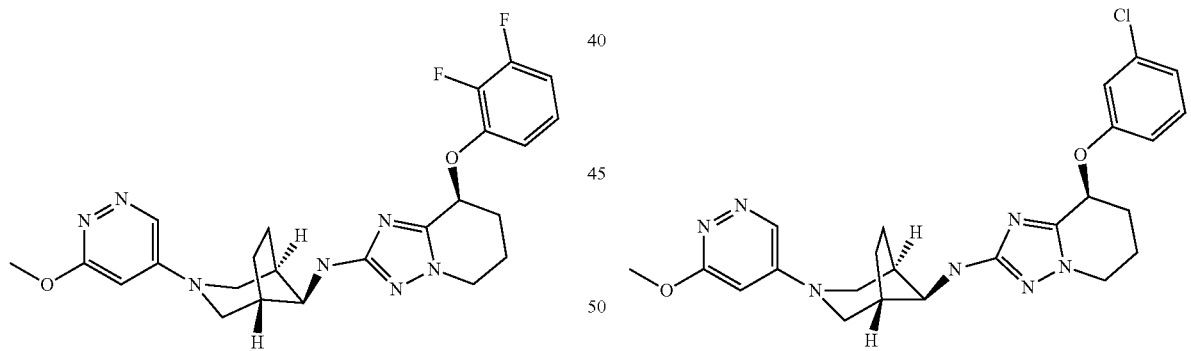

A Buchwald type coupling using the general procedure 1, between 2-bromo-8-(2,3-difluorophenoxy)-5,6,7,8-tetrahydro-[1,2,4]triazolo[1,5-a]pyridine 7-15 and (1R,5S,8S)-3-(6-methoxypyridazin-4-yl)-3-azabicyclo[3.2.1]octan-8-amine 8-2, followed by a separation of the enantiomers by preparative chiral HPLC afforded the title products as white solids (example 21): 27 mg, MS (ES+) m/z: 484.2 [(M+H)$^+$] and (example 22): 26 mg, MS (ES+) m/z: 484.2 [(M+H)$^+$].

A Buchwald type coupling using the general procedure 1, between 2-bromo-8-(3-chlorophenoxy)-5,6,7,8-tetrahydro-[1,2,4]triazolo[1,5-a]pyridine 7-11 and (1R,5S,8S)-3-(6-methoxypyridazin-4-yl)-3-azabicyclo[3.2.1]octan-8-amine 8-2, followed by a separation of the enantiomers by preparative chiral HPLC afforded the title products as white solids (example 23): 22 mg, MS (ES+) m/z: 482.2 [(M+H)$^+$] and (example 24): 22 mg, MS (ES+) m/z: 482.2 [(M+H)$^+$].

Examples 25 and 26

(R)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine and (S)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine

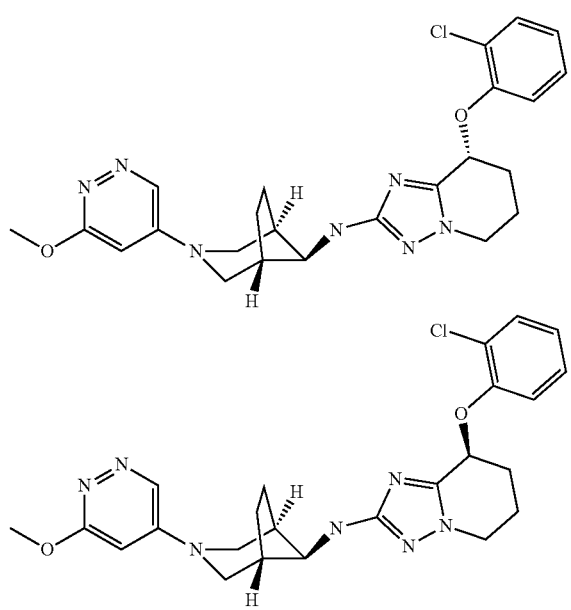

A Buchwald type coupling using the general procedure 1, between 2-bromo-8-(2-chlorophenoxy)-5,6,7,8-tetrahydro-[1,2,4]triazolo[1,5-a]pyridine 7-12 and (1R,5S,8S)-3-(6-methoxypyridazin-4-yl)-3-azabicyclo[3.2.1]octan-8-amine 8-2, followed by a separation of the enantiomeres by preparative chiral HPLC afforded the title products as white solids (example 25): 26 mg, MS (ES+) m/z: 482.2 [(M+H)$^+$] and (example 26): 26 mg, MS (ES+) m/z: 482.2 [(M+H)$^+$].

Examples 27 and 28

(R)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine and (S)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine

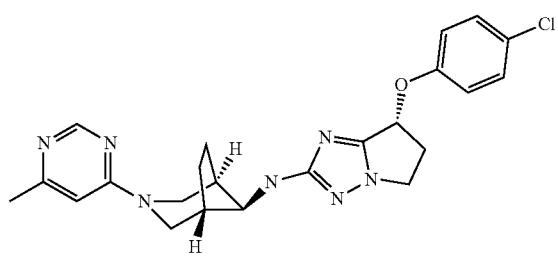

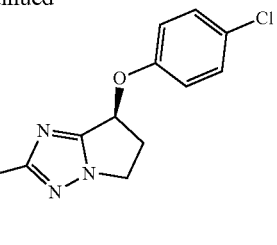

A Buchwald type coupling using the general procedure 1, between 2-bromo-7-(4-chlorophenoxy)-6,7-dihydro-5H-pyrrolo[1,2-b][1,2,4]triazole 7-4 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 27): 36 mg, MS (ES+) m/z: 452.1 [(M+H)$^+$] and (example 28): 36 mg, MS (ES+) m/z: 452.1 [(M+H)$^+$].

Examples 29 and 30

(R)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine and (S)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine

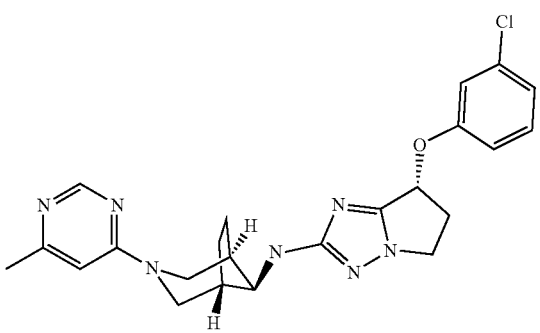

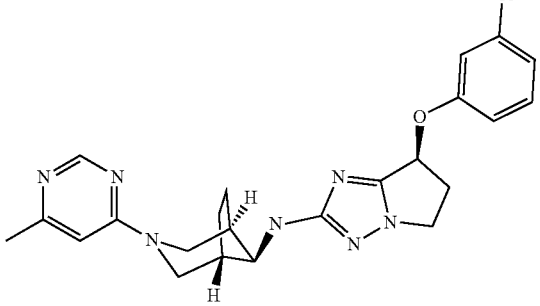

A Buchwald type coupling using the general procedure 1, between 2-bromo-7-(3-chlorophenoxy)-6,7-dihydro-5H-pyrrolo[1,2-b][1,2,4]triazole 7-5 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 29): 26 mg, MS (ES+) m/z: 452.1 [(M+H)$^+$] and (example 30): 25 mg, MS (ES+) m/z: 452.1 [(M+H)$^+$].

Examples 31 and 32

(R)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

Examples 33 and 34

(R)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

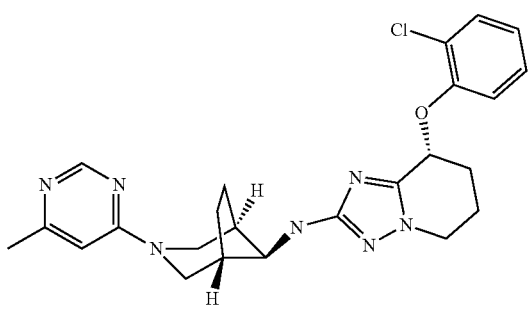

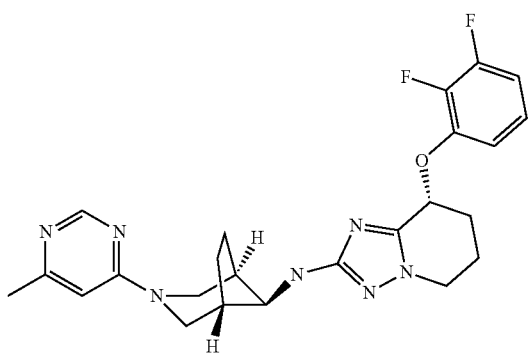

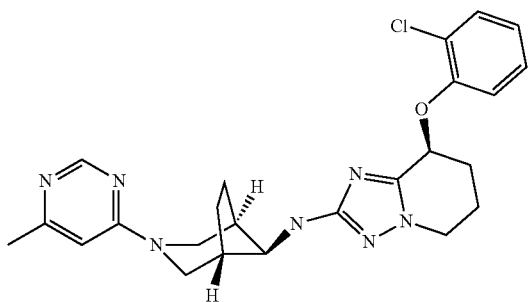

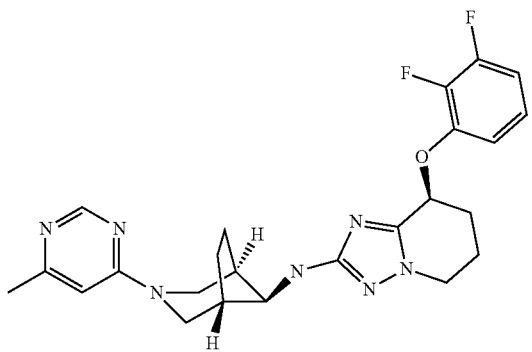

A Buchwald type coupling using the general procedure 1, between 2-bromo-8-(2-chlorophenoxy)-5,6,7,8-tetrahydro-[1,2,4]triazolo[1,5-a]pyridine 7-12 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 31): 20 mg, MS (ES+) m/z: 466.2 [(M+H)$^+$] and (example 32): 20 mg, MS (ES+) m/z: 466.2 [(M+H)$^+$].

A Buchwald type coupling using the general procedure 1, between 2-bromo-8-(2,3-difluorophenoxy)-5,6,7,8-tetrahydro-[1,2,4]triazolo[1,5-a]pyridine 7-15 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 33): 36 mg, MS (ES+) m/z: 468.2 [(M+H)$^+$] and (example 34): 31 mg, MS (ES+) m/z: 468.2 [(M+H)$^+$].

Examples 35 and 36

(R)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine and (S)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine

Examples 37 and 38

(R)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

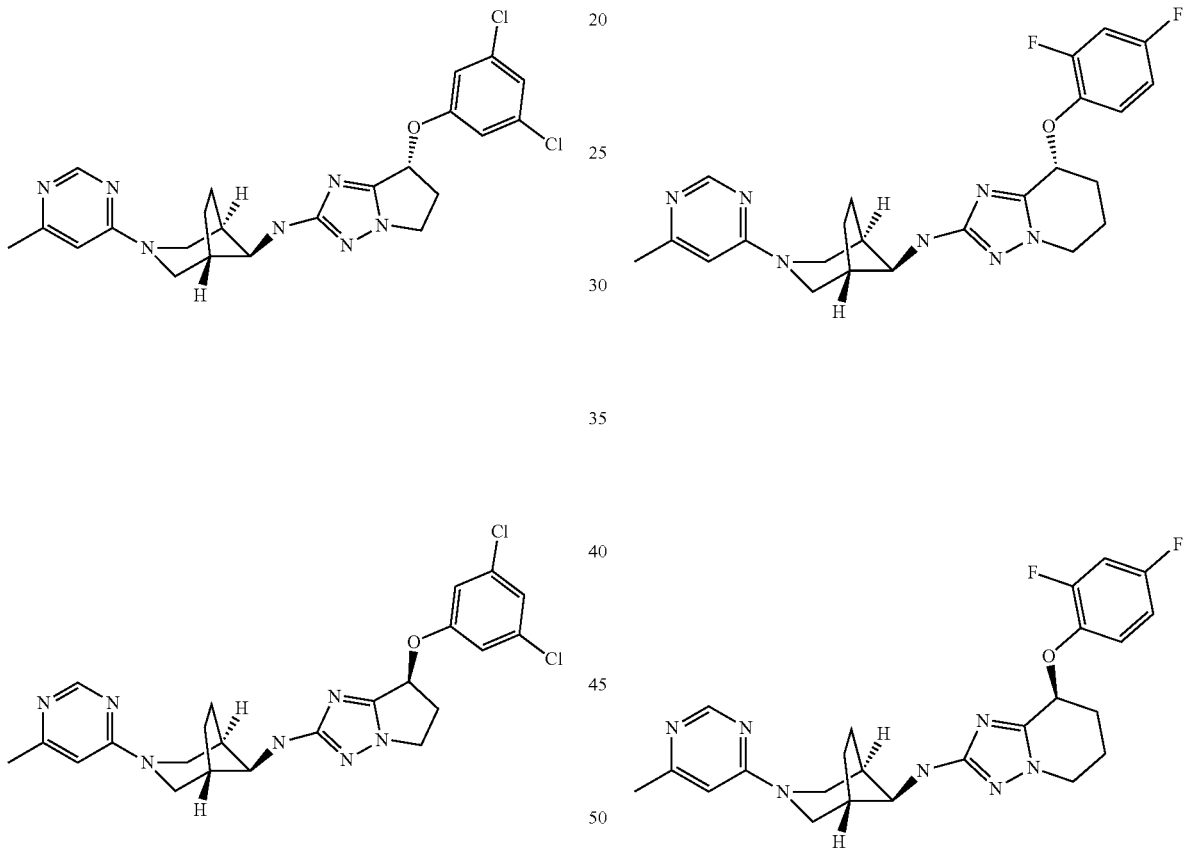

A Buchwald type coupling using the general procedure 1, between 2-bromo-7-(3,5-dichlorophenoxy)-6,7-dihydro-5H-pyrrolo[1,2-b][1,2,4]triazole 7-6 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 35): 27 mg, MS (ES+) m/z: 486.1 [(M+H)+] and (example 36): 27 mg, MS (ES+) m/z: 486.1 [(M+H)+].

A Buchwald type coupling using the general procedure 1, between 2-bromo-8-(2,4-difluorophenoxy)-5,6,7,8-tetrahydro-[1,2,4]triazolo[1,5-a]pyridine 7-10 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 37): 34 mg, MS (ES+) m/z: 468.2 [(M+H)+] and (example 38): 35 mg, MS (ES+) m/z: 468.2 [(M+H)+].

Examples 39 and 40

(R)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine and (S)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine

Examples 41 and 42

(R)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

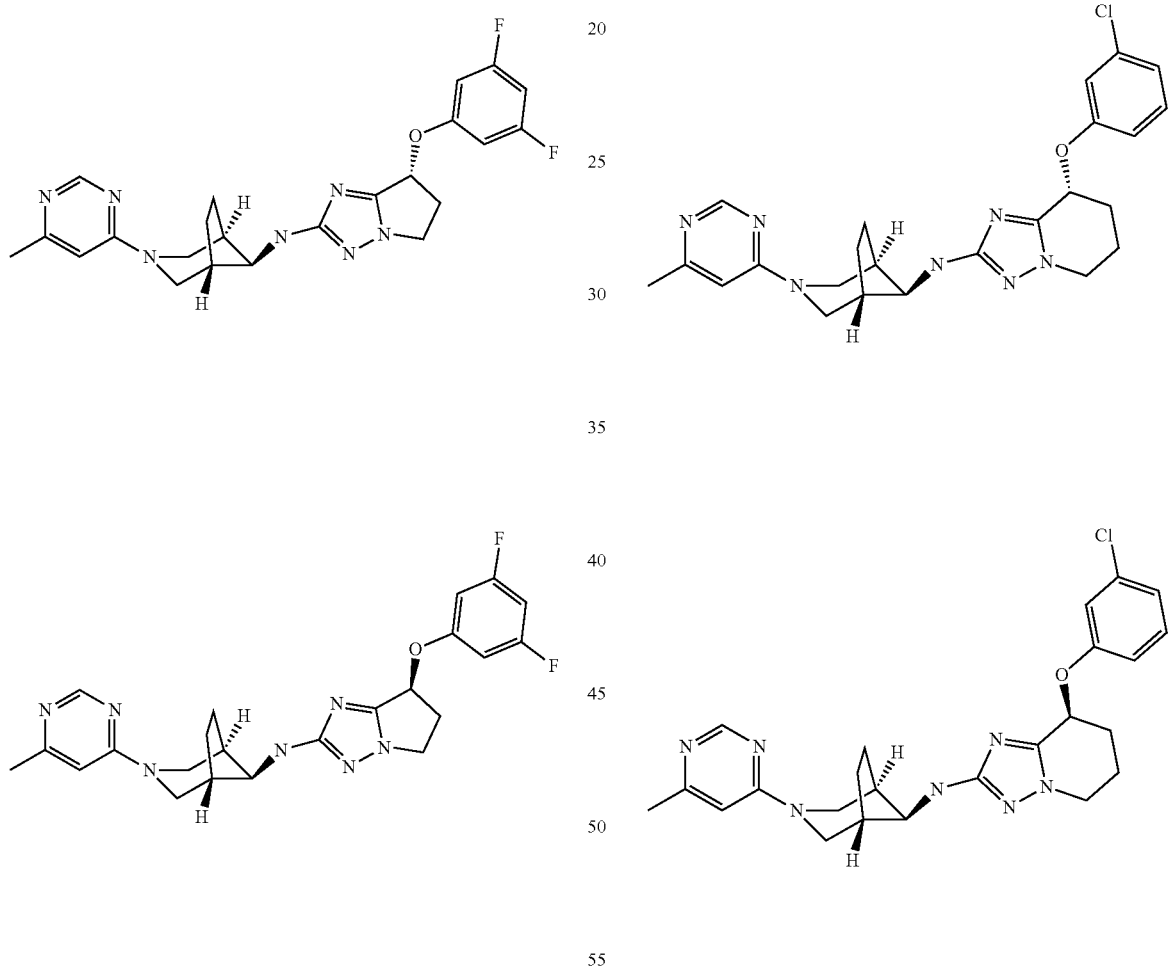

A Buchwald type coupling using the general procedure 1, between 2-bromo-7-(3,5-difluorophenoxy)-6,7-dihydro-5H-pyrrolo[1,2-b][1,2,4]triazole 7-1 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 39): 32 mg, MS (ES+) m/z: 454.2 [(M+H)$^+$] and (example 40): 31 mg, MS (ES+) m/z: 454.2 [(M+H)$^+$].

A Buchwald type coupling using the general procedure 1, between 2-bromo-8-(3-chlorophenoxy)-5,6,7,8-tetrahydro-[1,2,4]triazolo[1,5-a]pyridine 7-11 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 41): 30 mg, MS (ES+) m/z: 466.2 [(M+H)$^+$] and (example 42): 28 mg, MS (ES+) m/z: 466.2 [(M+H)$^+$].

Examples 43 and 44

(R)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

Examples 45 and 46

(R)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

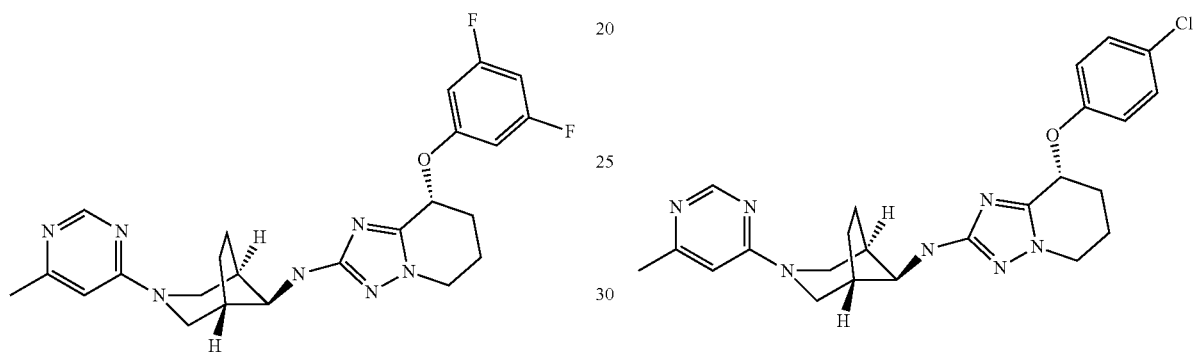

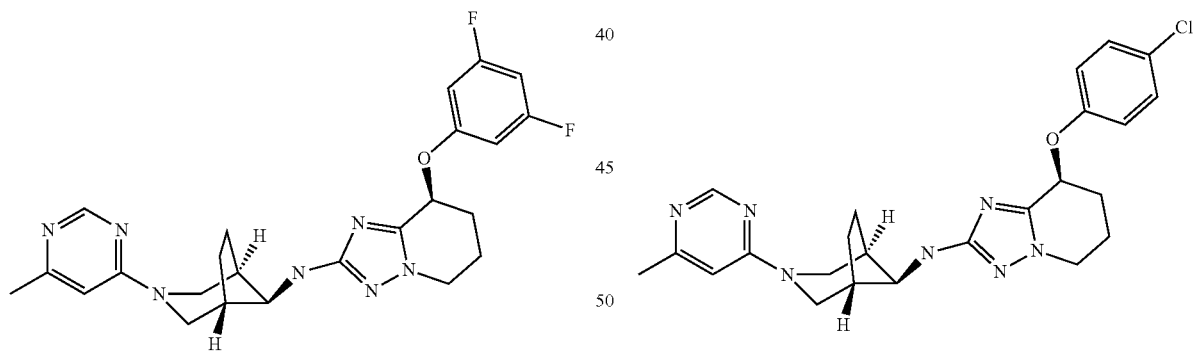

A Buchwald type coupling using the general procedure 1, between 2-bromo-8-(3,5-difluorophenoxy)-5,6,7,8-tetrahydro-[1,2,4]triazolo[1,5-a]pyridine 7-8 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 43): 36 mg, MS (ES+) m/z: 468.2 [(M+H)$^+$] and (example 44): 34 mg, MS (ES+) m/z: 468.2 [(M+H)$^+$].

A Buchwald type coupling using the general procedure 1, between 2-bromo-8-(4-chlorophenoxy)-5,6,7,8-tetrahydro-[1,2,4]triazolo[1,5-a]pyridine 7-13 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 45): 27 mg, MS (ES+) m/z: 466.2 [(M+H)$^+$] and (example 46): 27 mg, MS (ES+) m/z: 466.2 [(M+H)$^+$].

Examples 47 and 48

(R)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine and (S)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine

Examples 49 and 50

(R)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

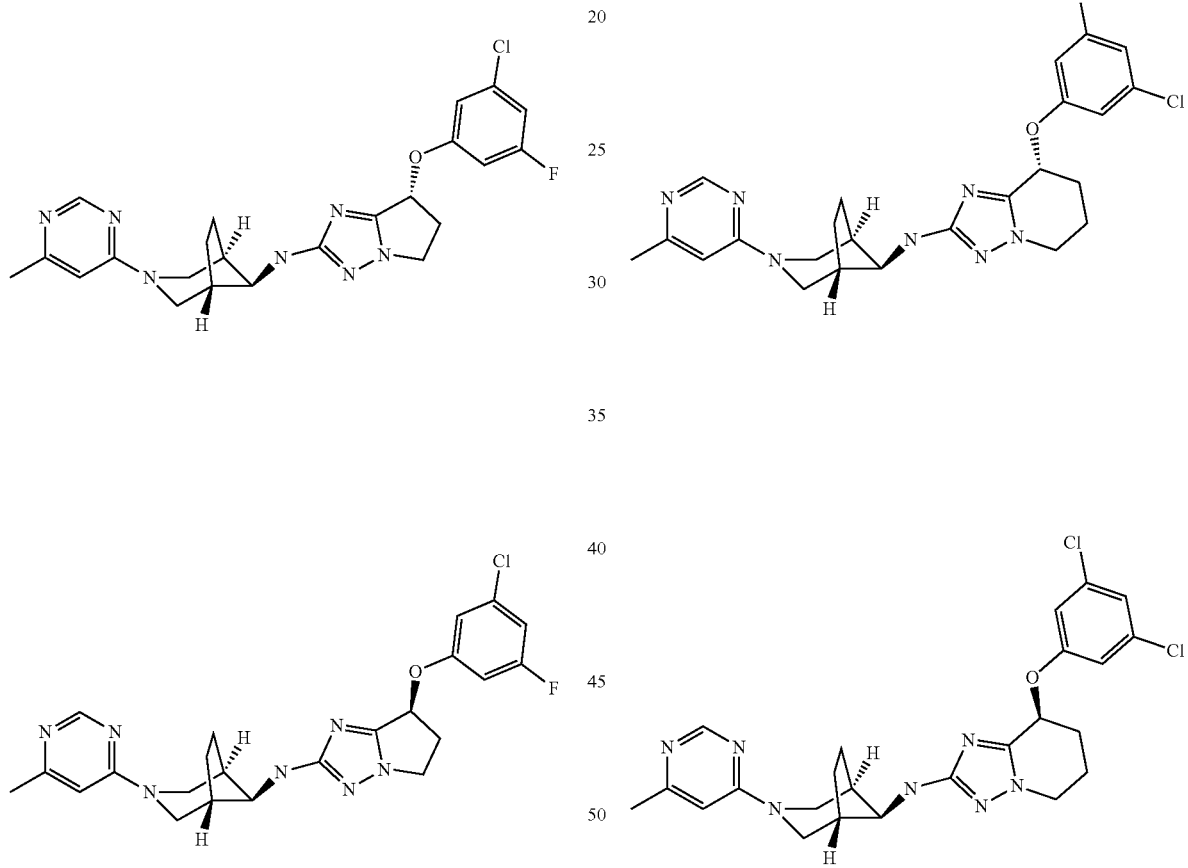

A Buchwald type coupling using the general procedure 1, between 2-bromo-7-(3-chloro-5-fluorophenoxy)-6,7-dihydro-5H-pyrrolo[1,2-b][1,2,4]triazole 7-2 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 47): 28 mg, MS (ES+) m/z: 470.1 [(M+H)$^+$] and (example 48): 27 mg, MS (ES+) m/z: 470.1 [(M+H)$^+$].

A Buchwald type coupling using the general procedure 1, between 2-bromo-8-(3,5-dichlorophenoxy)-5,6,7,8-tetrahydro-[1,2,4]triazolo[1,5-a]pyridine 7-14 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 49): 19 mg, MS (ES+) m/z: 500.1 [(M+H)$^+$] and (example 50): 18 mg, MS (ES+) m/z: 500.1 [(M+H)$^+$].

Examples 51 and 52

(R)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine and (S)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine

Examples 53 and 54

(R)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

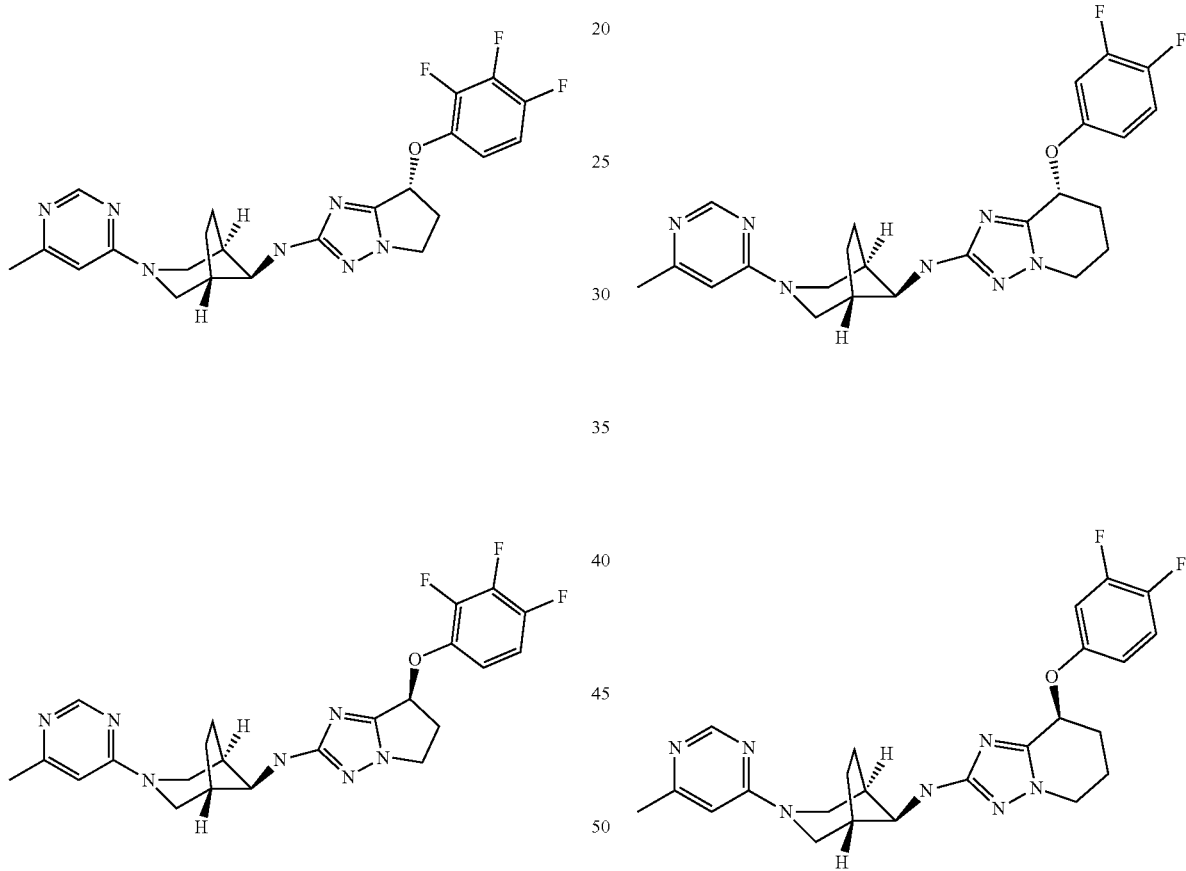

A Buchwald type coupling using the general procedure 1, between 2-bromo-7-(2,3,4-trifluorophenoxy)-6,7-dihydro-5H-pyrrolo[1,2-b][1,2,4]triazole 7-3 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 51): 36 mg, MS (ES+) m/z: 472.2 [(M+H)$^+$] and (example 52): 35 mg, MS (ES+) m/z: 472.2 [(M+H)$^+$].

A Buchwald type coupling using the general procedure 1, between 2-bromo-8-(3,4-difluorophenoxy)-5,6,7,8-tetrahydro-[1,2,4]triazolo[1,5-a]pyridine 7-16 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 53): 35 mg, MS (ES+) m/z: 468.2 [(M+H)$^+$] and (example 54): 36 mg, MS (ES+) m/z: 468.2 [(M+H)$^+$].

Examples 55 and 56

(R)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine and (S)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine

Examples 57 and 58

(R)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine and (S)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine

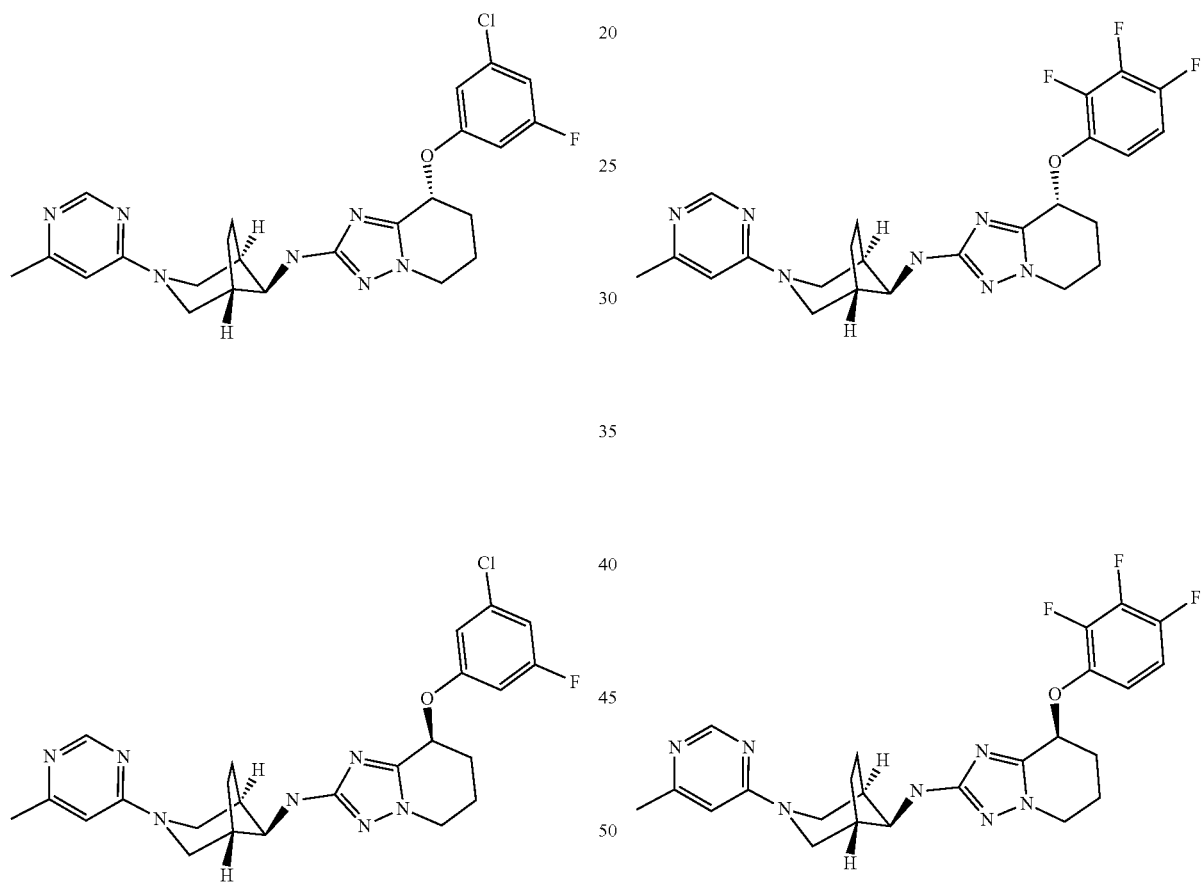

A Buchwald type coupling using the general procedure 1, between 2-bromo-8-(3-chloro-5-fluorophenoxy)-5,6,7,8-tetrahydro-[1,2,4]triazolo[1,5-a]pyridine 7-7 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 55): 26 mg, MS (ES+) m/z: 484.2 [(M+H)$^+$] and (example 56): 26 mg, MS (ES+) m/z: 484.2 [(M+H)$^+$].

A Buchwald type coupling using the general procedure 1, between 2-bromo-8-(2,3,4-trifluorophenoxy)-5,6,7,8-tetrahydro-[1,2,4]triazolo[1,5-a]pyridine 7-9 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 57): 27 mg, MS (ES+) m/z: 486.2 [(M+H)$^+$] and (example 58): 29 mg, MS (ES+) m/z: 486.2 [(M+H)$^+$].

Examples 59 and 60

(R)-9-(4-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine and (S)-9-(4-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine

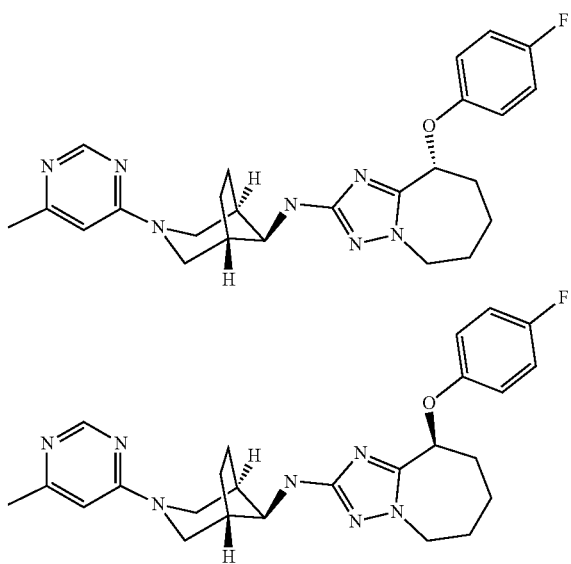

A Buchwald type coupling using the general procedure 1, between 2-bromo-9-(4-fluorophenoxy)-6,7,8,9-tetrahydro-5H-[1,2,4]triazolo[1,5-a]azepine 7-17 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 59): 32 mg, MS (ES+) m/z: 464.2 [(M+H)$^+$] and (example 60): 32 mg, MS (ES+) m/z: 464.2 [(M+H)$^+$].

Examples 61 and 62

(R)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine and (S)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine

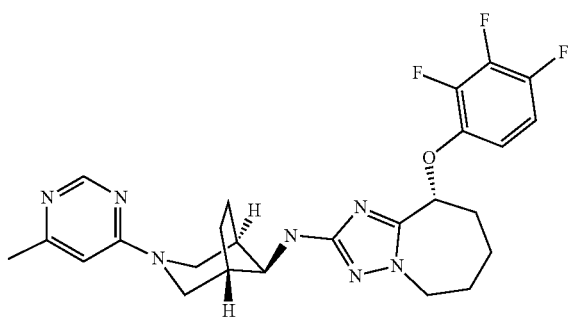

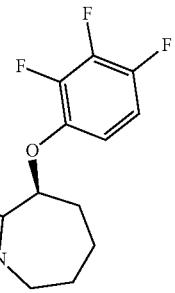

A Buchwald type coupling using the general procedure 1, between 2-bromo-9-(2,3,4-fluorophenoxy)-6,7,8,9-tetrahydro-5H-[1,2,4]triazolo[1,5-a]azepine 7-18 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 61): 36 mg, MS (ES+) m/z: 500.2 [(M+H)$^+$] and (example 62): 33 mg, MS (ES+) m/z: 500.2 [(M+H)$^+$].

Examples 63 and 64

(R)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine and (S)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine

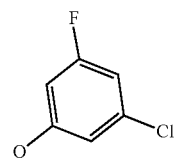

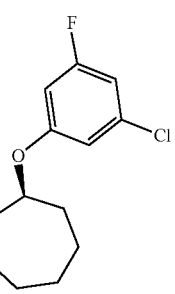

A Buchwald type coupling using the general procedure 1, between 2-bromo-9-(3-chloro-5-fluorophenoxy)-6,7,8,9-tetrahydro-5H-[1,2,4]triazolo[1,5-a]azepine 7-19 and (1R,5S,8S)-3-(6-methylpyrimidin-4-yl)-3-azabicyclo[3.2.1]octan-8-amine 8-1, followed by a separation of the enantiomeres by preparative chiral HPLC afforded the title products as white solids (example 63): 13 mg, MS (ES+) m/z: 498.2 [(M+H)+] and (example 64): 18 mg, MS (ES+) m/z: 498.2 [(M+H)+].

2) Biological Examples 2.1) Assay Procedure: Cellular γ-Secretase Assay

Human neuroglioma H4 cells overexpressing human APP695 with the Swedish double mutation (K595N/M596L) were plated at 30,000 cells/well/100 μL in 96-well plates in IMDM containing 10% FCS, 0.2 mg/L Hygromycin B and incubated at 37° C., 5% $CO_2$.

3-4 h post plating, compounds are a diluted in media and 50 μL is added as 1.5-fold concentrate to achieve the final concentration. Compound incubation is performed for 24 h. Final doses typically range from 4 μM down to 0.0013 μM in half-log steps resulting in an eight-point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa® assay kit (Human Amyloid beta 1-42 Kit, Perkin Elmer Inc.). 20 μL of the cell culture supernatant was transferred to an assay plate. Then 10 μL of a mixture of the AlphaLisa® coupled capture antibody and the biotinylated detection antibody was added and incubated for 3 h at RT while softly shaking the assay plate. After a further addition of 20 μL of the Donor beads the assay plate was incubated for 30 min at RT and constant shaking without exposure to direct light. The assay plate was then read on a Paradigm AlphaLisa® Reader using the build-in program with excitation at 680 nm and emission at 570 nm. The measured signals were then used to calculate $IC_{50}$ values for inhibition of Aβ42 secretion by nonlinear regression fit analysis using XLfit 5.3 software (from IDBS Ltd).

2.2) Results

The table below shows the data for all compounds for the inhibition of Aβ42 secretion:

| Example | Aβ42 $IC_{50}$ (μM) |
|---|---|
| 1 | 0.0128 |
| 2 | 0.0738 |
| 3 | 0.0081 |
| 4 | 0.0413 |
| 5 | 0.0114 |
| 7 | 0.0063 |
| 8 | 0.0341 |
| 9 | 0.0106 |
| 10 | 0.0393 |
| 11 | 0.0113 |
| 12 | 0.0601 |
| 13 | 0.0199 |
| 14 | 0.0627 |
| 15 | 0.0357 |
| 17 | 0.0497 |
| 19 | 0.0368 |
| 21 | 0.0318 |
| 22 | 0.0943 |
| 23 | 0.0119 |
| 24 | 0.0575 |
| 25 | 0.0157 |
| 26 | 0.0338 |
| 27 | 0.0165 |
| 28 | 0.0714 |
| 29 | 0.0175 |
| 30 | 0.0519 |
| 31 | 0.0138 |
| 32 | 0.0335 |
| 33 | 0.0171 |
| 34 | 0.0536 |
| 35 | 0.0160 |
| 36 | 0.0224 |
| 37 | 0.0216 |
| 39 | 0.0156 |
| 40 | 0.0761 |
| 41 | 0.0099 |
| 42 | 0.0275 |
| 43 | 0.0124 |
| 44 | 0.0340 |
| 45 | 0.0103 |
| 46 | 0.0282 |
| 47 | 0.0117 |
| 48 | 0.0277 |
| 49 | 0.0066 |
| 50 | 0.0200 |
| 51 | 0.0177 |
| 53 | 0.0113 |
| 54 | 0.0413 |
| 55 | 0.0081 |
| 56 | 0.0295 |
| 57 | 0.0105 |
| 58 | 0.0432 |
| 59 | 0.0428 |
| 60 | 0.0849 |
| 61 | 0.0136 |
| 62 | 0.0658 |
| 63 | 0.0138 |
| 64 | 0.0347 |

The invention claimed is:

1. A compound of formula (I)

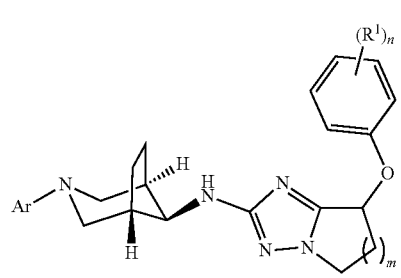

wherein:
R¹ is halogen, lower alkyl, lower alkyl substituted by halogen, lower alkoxy, or lower alkoxy substituted by halogen,
and R¹ may be different if n=2 or 3;
m is 1, 2 or 3;
n is 1, 2 or 3;
Ar is a six membered heteroaryl group, selected from

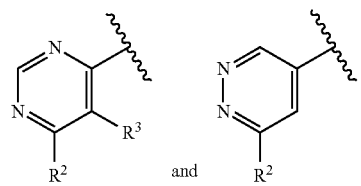

wherein:
R² is hydrogen, halogen, lower alkyl, lower alkyl substituted by halogen, or lower alkoxy;
R³ is hydrogen or halogen;
or a pharmaceutically acceptable salt thereof.

2. The compound according to claim 1, or a pharmaceutically acceptable salt thereof, wherein the compound has formula (Ia)

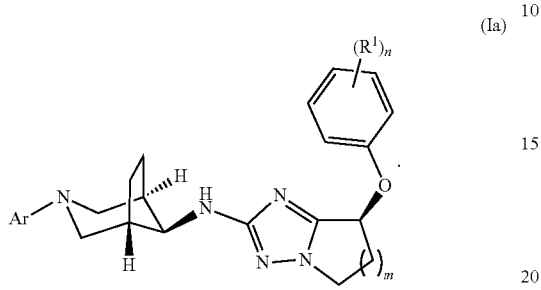

(Ia)

3. The compound of claim 1, or a pharmaceutically acceptable salt thereof, wherein the compound has formula (Ib)

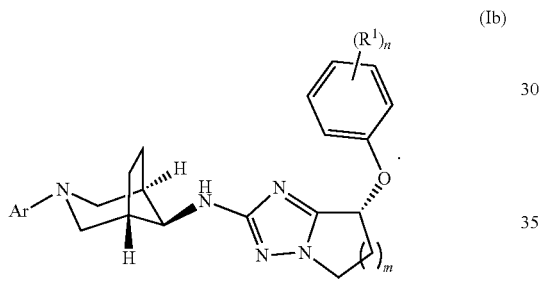

(Ib)

4. The compound of formula (I) according to claim 1, or a pharmaceutically acceptable salt thereof, wherein R¹ is halogen.

5. The compound of formula (I) according to claim 1, or a pharmaceutically acceptable salt thereof, wherein R¹ is fluorine or chlorine.

6. The compound of formula (I) according to claim 1, or a pharmaceutically acceptable salt thereof, wherein m is 1 or 2.

7. The compound of formula (I) according to claim 1, or a pharmaceutically acceptable salt thereof, wherein:
R² is lower alkyl or lower alkoxy; and
R³ is hydrogen.

8. The compound of formula (I) according to claim 1, or a pharmaceutically acceptable salt thereof, wherein:
R² is methyl or methoxy; and
R³ is hydrogen.

9. The compound of formula (I) according to claim 1, or a pharmaceutically acceptable salt thereof, wherein:
R¹ is halogen;
m is 1 or 2;
R² is lower alkyl or lower alkoxy; and
R³ is hydrogen.

10. The compound of formula (I) according to claim 1, or a pharmaceutically acceptable salt thereof, wherein:
R¹ is fluorine or chlorine;
m is 1 or 2;
R² is methyl or methoxy; and
R³ is hydrogen.

11. A compound according to claim 1, selected from:
(R)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(S)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(R)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(S)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;
(R)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;
(S)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;
(R)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(S)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(R)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;
(S)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;
(R)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;
(S)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine;
(R)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(S)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(R)-8-(2,4-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(2,4-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(S)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;
(R)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(S)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(R)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(S)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(R)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(S)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(R)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(S)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(R)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(S)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;
(R)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;
(S)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;
(R)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(S)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;
(R)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(S)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;
(R)-9-(4-fluorophenoxy)-N-((1R,5S,8s)-3-(6-methylpyrimidin-4-yl)-3-azabicyclo[3.2.1]-octan-8-yl)-6,7,8,9-tetrahydro-5H-[1,2,4]triazolo[1,5-a]azepin-2-amine;

(S)-9-(4-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine;

(R)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine;

(S)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine;

(R)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine; and (S)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine;

or a pharmaceutically acceptable salt thereof.

12. A compound according to claim 1, selected from:

(R)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;

(S)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;

(R)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;

(S)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine;

(R)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;

(S)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine;

(R)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(S)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(R)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(S)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine;

(R)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(S)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

(R)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(S)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine;

(R)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(S)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine;

(R)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine; and (S)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine;

or a pharmaceutically acceptable salt thereof.

13. A process for preparing a compound according to claim 1, or a pharmaceutically acceptable salt thereof, the process comprising:

reacting a compound 7

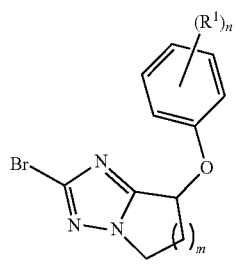

with an amine 8

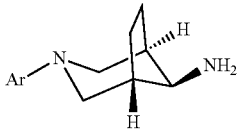

to form said compound, and optionally, converting the compound obtained into a pharmaceutically acceptable salt thereof.

14. A pharmaceutical composition comprising a compound according to claim 1, or a pharmaceutically acceptable salt thereof, and a pharmaceutically acceptable excipient.

15. A pharmaceutical composition comprising a compound according to claim 11, or a pharmaceutically acceptable salt thereof, and a pharmaceutically acceptable excipient.

16. A compound, or a pharmaceutically acceptable salt thereof, when the compound is:

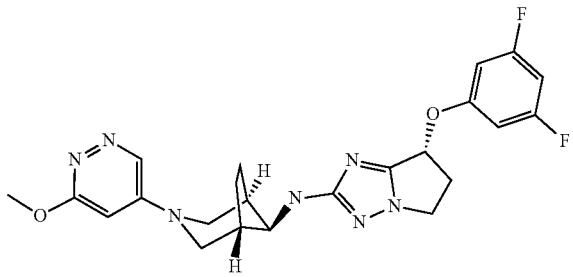

(R)-7-(3,5-difluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine.

17. The compound of claim 1, or a pharmaceutically acceptable salt thereof, wherein the compound is:

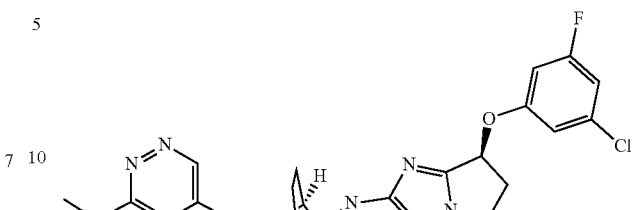

(S)-7-(3-chloro-5-fluorophenoxy)-N-((1R,5S,8s)-3-(6-methoxypyridazin-4-yl)-3-azabicyclo[3.2.1]octan-8-yl)-6,7-dihydro-5H-pyrrolo[1,2-b][1,2,4]triazol-2-amine.

18. The compound of claim 1, or a pharmaceutically acceptable salt thereof, wherein the compound is:

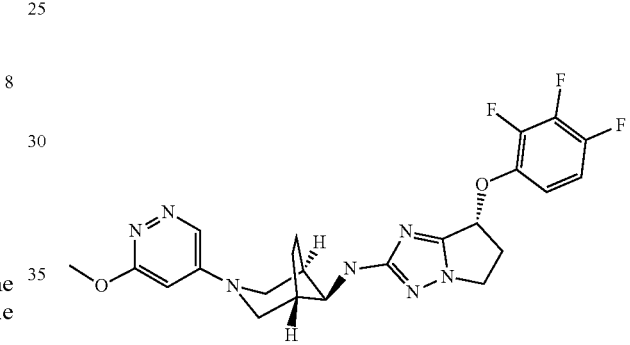

(R)—N-((1R,5S,8s)-3-(6-methoxypyridazin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine.

19. The compound of claim 1, or a pharmaceutically acceptable salt thereof, wherein the compound is:

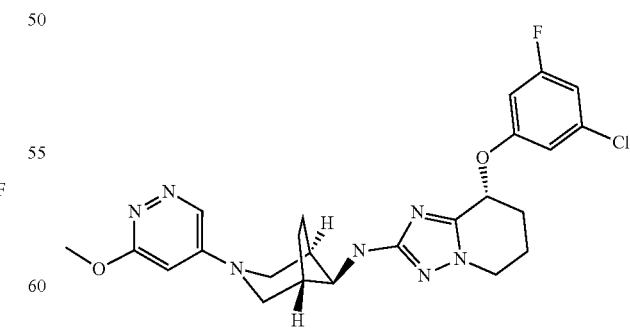

(R)-8-(3-chloro-5-fluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine.

20. A compound, or a pharmaceutically acceptable salt thereof, wherein the compound is:

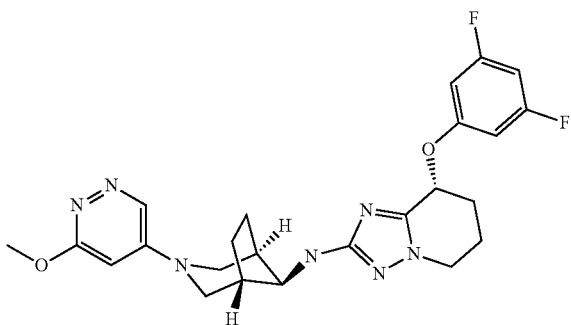 [SMILES: COc1cc(N2C[C@H]3CC[C@@H](C2)[C@@H]3Nc2nc3n(n2)CCC[C@H]3Oc2cc(F)cc(F)c2)cnn1]

(R)-8-(3,5-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine.

21. The compound of claim 1, or a pharmaceutically acceptable salt thereof, wherein the compound is:

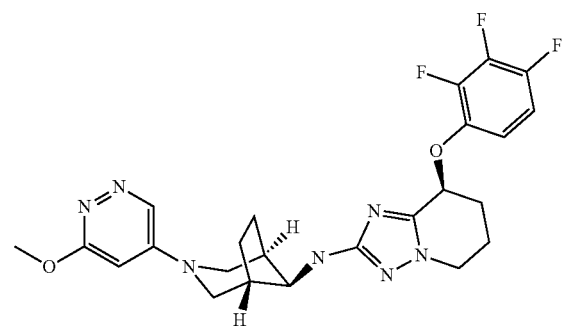 [SMILES: COc1cc(N2C[C@H]3CC[C@@H](C2)[C@@H]3Nc2nc3n(n2)CCC[C@@H]3Oc2ccc(F)c(F)c2F)cnn1]

(S)—N-((1R,5S,8s)-3-(6-methoxypyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine.

22. The compound of claim 1, or a pharmaceutically acceptable salt thereof, wherein the compound is:

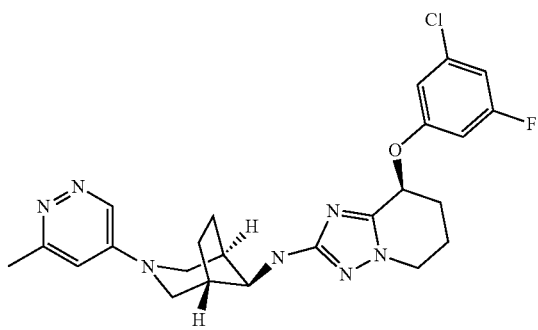 [SMILES: Cc1cc(N2C[C@H]3CC[C@@H](C2)[C@@H]3Nc2nc3n(n2)CCC[C@@H]3Oc2cc(F)cc(F)c2)cnn1]

(S)-8-(3-chloro-5-fluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine.

23. The compound of claim 1, or a pharmaceutically acceptable salt thereof, wherein the compound is:

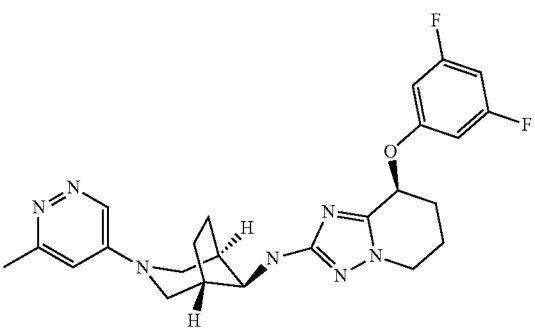

(S)-8-(3,5-difluorophenoxy)-N-((1R,5S,8s)-3-(6-methylpyridazin-4-yl)-3-azabicyclo[3.2.1]octan-8-yl)-5,6,7,8-tetrahydro-[1,2,4]triazolo[1,5-a]pyridin-2-amine.

24. A compound, or a pharmaceutically acceptable salt thereof, wherein the compound is:

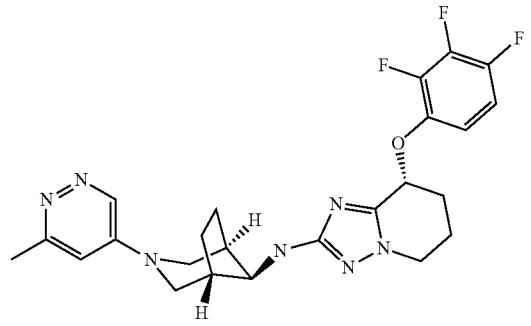 [SMILES: Cc1cc(N2C[C@H]3CC[C@@H](C2)[C@@H]3Nc2nc3n(n2)CCC[C@H]3Oc2ccc(F)c(F)c2F)cnn1]

(R)—N-((1R,5S,8s)-3-(6-methylpyridazin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine.

25. The compound of claim 1, or a pharmaceutically acceptable salt thereof, wherein the compound is:

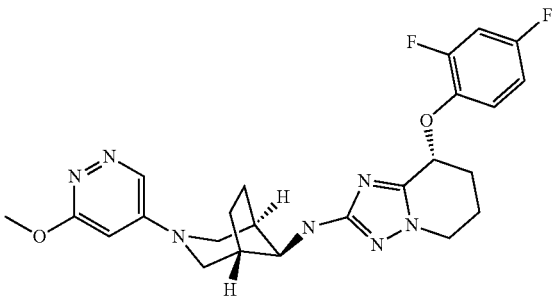 [SMILES: COc1cc(N2C[C@H]3CC[C@@H](C2)[C@@H]3Nc2nc3n(n2)CCC[C@H]3Oc2ccc(F)cc2F)cnn1]

(R)-8-(2,4-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine.

26. The compound of claim 1, or a pharmaceutically acceptable salt thereof, wherein the compound is:

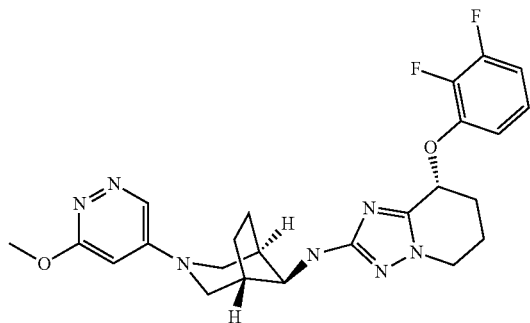 [SMILES: COc1cc(N2C[C@H]3CC[C@@H](C2)[C@@H]3Nc2nc3n(n2)CCC[C@H]3Oc2cccc(F)c2F)cnn1]

(R)-8-(2,3-difluorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine.

27. The compound of claim 1, or a pharmaceutically acceptable salt thereof, wherein the compound is:

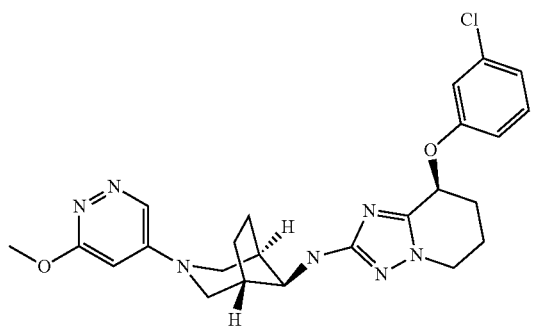 [SMILES: COc1cc(N2C[C@H]3CC[C@@H](C2)[C@@H]3Nc2nc3n(n2)CCC[C@@H]3Oc2cccc(Cl)c2)cnn1]

(S)-8-(3-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine.

28. A compound, or a pharmaceutically acceptable salt thereof, wherein the compound is:

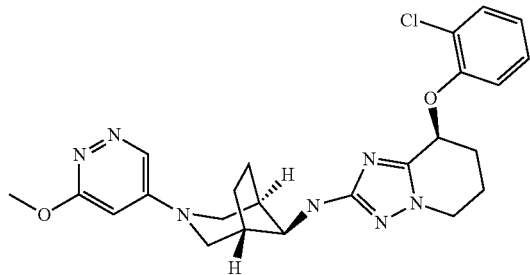 [SMILES: COc1cc(N2C[C@H]3CC[C@@H](C2)[C@@H]3Nc2nc3n(n2)CCC[C@@H]3Oc2ccccc2Cl)cnn1]

(S)-8-(2-chlorophenoxy)-N-((1R,5S,8s)-3-(6-methoxypyridazin-4-yl)-3-azabicyclo[3.2.1]octan-8-yl)-5,6,7,8-tetrahydro-[1,2,4]triazolo[1,5-a]pyridin-2-amine.

29. The compound of claim 1, or a pharmaceutically acceptable salt thereof, wherein the compound is:

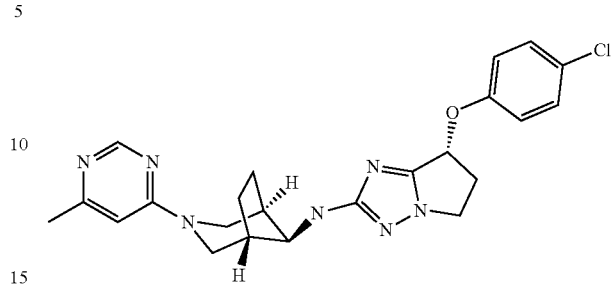

(R)-7-(4-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine.

30. The compound of claim 1, or a pharmaceutically acceptable salt thereof, wherein the compound is:

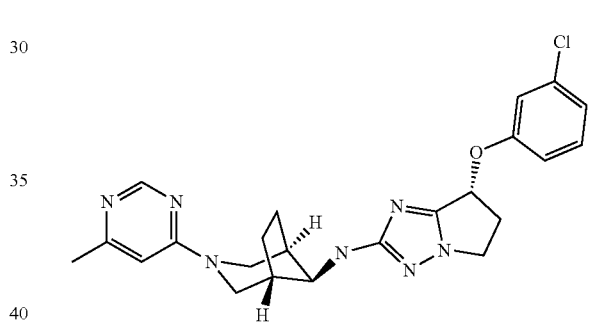

(R)-7-(3-chlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine.

31. The compound of claim 1, or a pharmaceutically acceptable salt thereof, wherein the compound is:

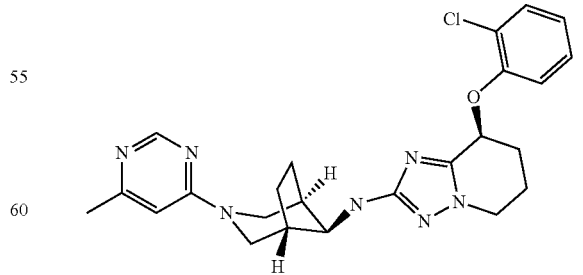

(S)-8-(2-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

32. The compound of claim 1, or a pharmaceutically acceptable salt thereof, wherein the compound is:

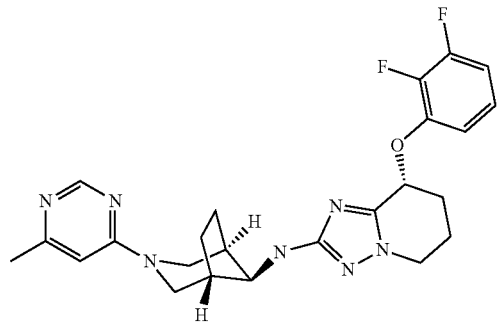 [SMILES: Cc1cc(N2C[C@H]3CC[C@@H](C2)[C@@H]3Nc2nc3n(n2)CCC[C@H]3Oc2cccc(F)c2F)ncn1]

(R)-8-(2,3-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

33. A compound, or a pharmaceutically acceptable salt thereof, wherein the compound is:

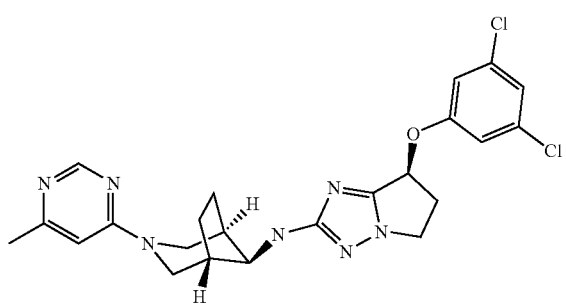 [SMILES: Cc1cc(N2C[C@H]3CC[C@@H](C2)[C@@H]3Nc2nc3n(n2)CC[C@@H]3Oc2cc(Cl)cc(Cl)c2)ncn1]

(S)-7-(3,5-dichlorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine.

34. The compound of claim 1, or a pharmaceutically acceptable salt thereof, wherein the compound is:

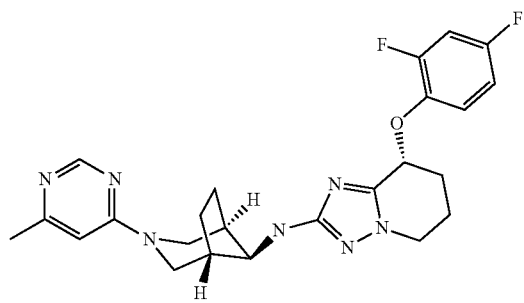 [SMILES: Cc1cc(N2C[C@H]3CC[C@@H](C2)[C@@H]3Nc2nc3n(n2)CCC[C@H]3Oc2ccc(F)cc2F)ncn1]

(R)-8-(2,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

35. The compound of claim 1, or a pharmaceutically acceptable salt thereof, wherein the compound is:

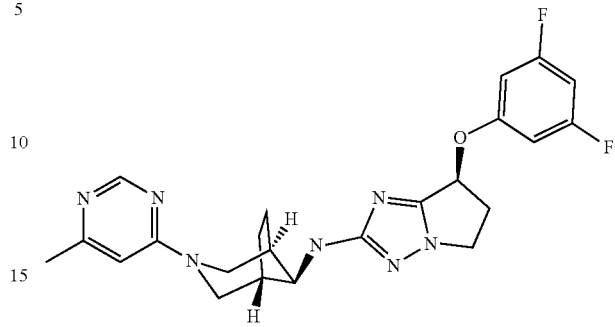

(S)-7-(3,5-difluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine.

36. The compound of claim 1, or a pharmaceutically acceptable salt thereof, wherein the compound is:

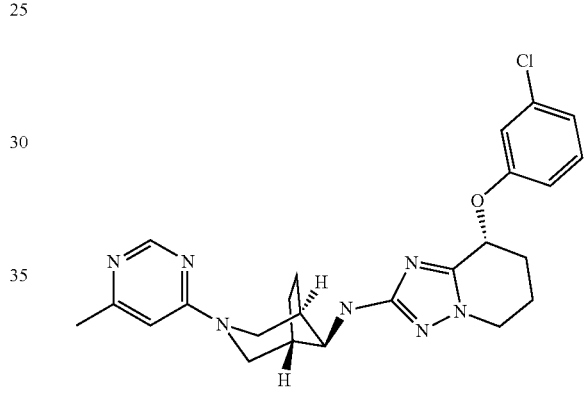

(R)-8-(3-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

37. A compound, or a pharmaceutically acceptable salt thereof, wherein the compound is:

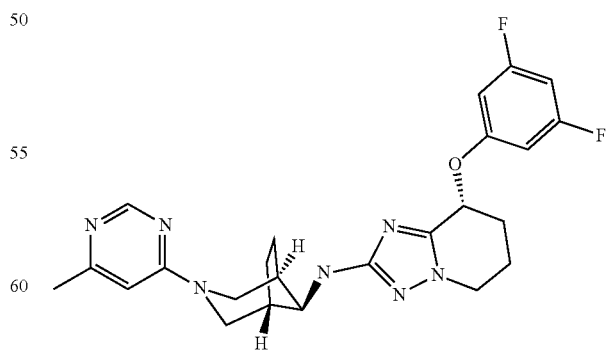

(R)-8-(3,5-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

38. The compound of claim 1, or a pharmaceutically acceptable salt thereof, wherein the compound is:

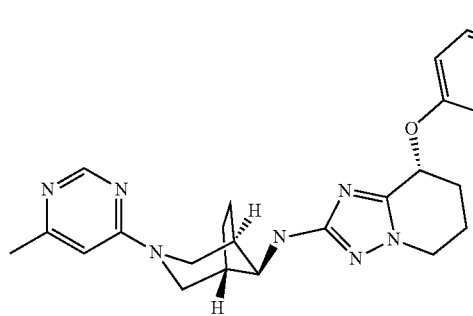

(R)-8-(4-chlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

39. The compound of claim 1, or a pharmaceutically acceptable salt thereof, wherein the compound is:

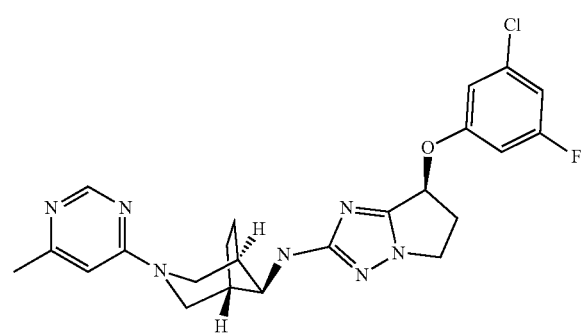

(S)-7-(3-chloro-5-fluorophenoxy)-N-((1R,5S,8s)-3-(6-methylpyrimidin-4-yl)-3-azabicyclo[3.2.1]octan-8-yl)-6,7-dihydro-5H-pyrrolo[1,2-b][1,2,4]triazol-2-amine.

40. The compound of claim 1, or a pharmaceutically acceptable salt thereof, wherein the compound is:

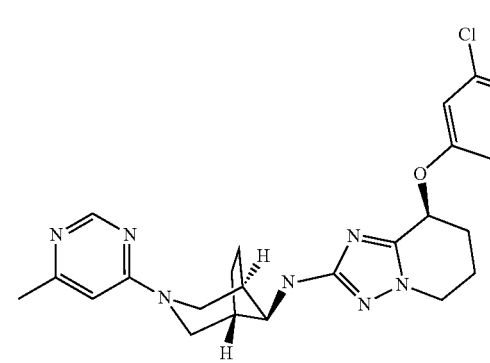

(S)-8-(3,5-dichlorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

41. A compound, or a pharmaceutically acceptable salt thereof, wherein the compound is:

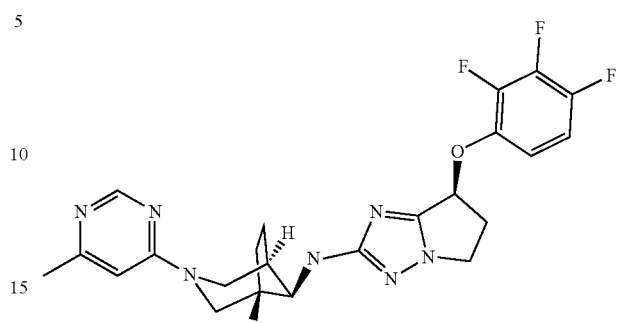

(S)—N-((1R,5S,8s)-3-(6-methylpyrimidin-4-yl)-3-azabicyclo[3.2.1]octan-8-yl)-7-(2,3,4-trifluorophenoxy)-6,7-dihydro-5H-pyrrolo[1,2-b][1,2,4]triazol-2-amine.

42. The compound of claim 1, or a pharmaceutically acceptable salt thereof, wherein the compound is:

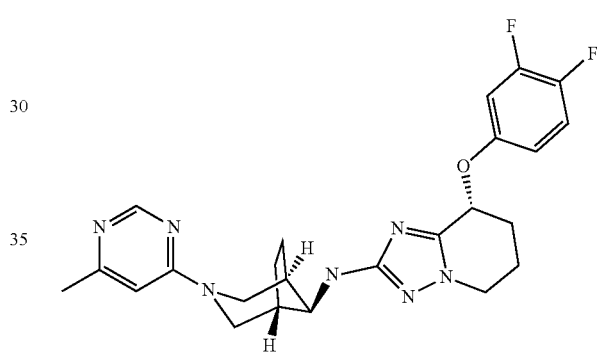

(R)-8-(3,4-difluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

43. The compound of claim 1, or a pharmaceutically acceptable salt thereof, wherein the compound is:

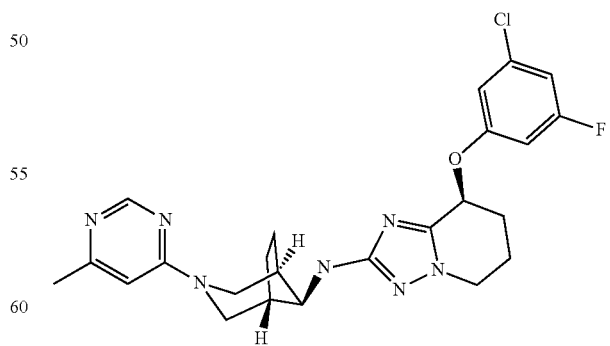

(S)-8-(3-chloro-5-fluorophenoxy)-N-((1R,5S,8s)-3-(6-methylpyrimidin-4-yl)-3-azabicyclo[3.2.1]octan-8-yl)-5,6,7,8-tetrahydro-[1,2,4]triazolo[1,5-a]pyridin-2-amine.

44. The compound of claim 1, or a pharmaceutically acceptable salt thereof, wherein the compound is:

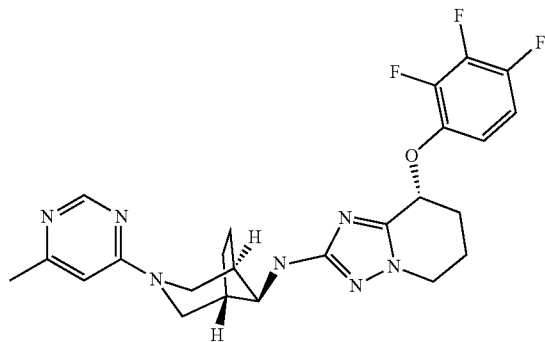

(R)—N-((1R,5S,8s)-3-(6-methylpyrimidin-4-yl)-3-azabicyclo[3.2.1]octan-8-yl)-8-(2,3,4-trifluorophenoxy)-5,6,7,8-tetrahydro-[1,2,4]triazolo[1,5-a]pyridin-2-amine.

45. A compound, or a pharmaceutically acceptable salt thereof, wherein the compound is:

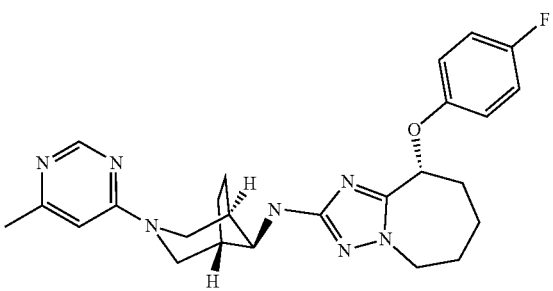

(R)-9-(4-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine.

46. The compound of claim 1, or a pharmaceutically acceptable salt thereof, wherein the compound is:

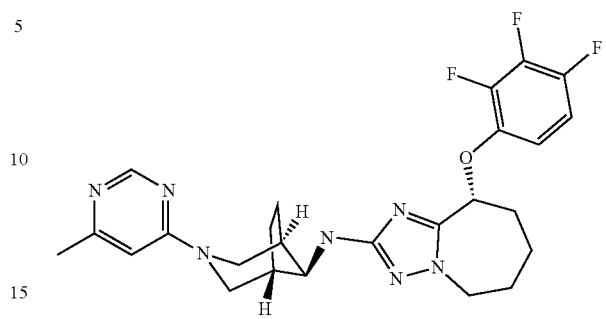

(R)—N-((1R,5S,8s)-3-(6-methylpyrimidin-4-yl)-3-azabicyclo[3.2.1]octan-8-yl)-9-(2,3,4-trifluorophenoxy)-6,7,8,9-tetrahydro-5H-[1,2,4]triazolo[1,5-a]azepin-2-amine.

47. The compound of claim 1, or a pharmaceutically acceptable salt thereof, wherein the compound is:

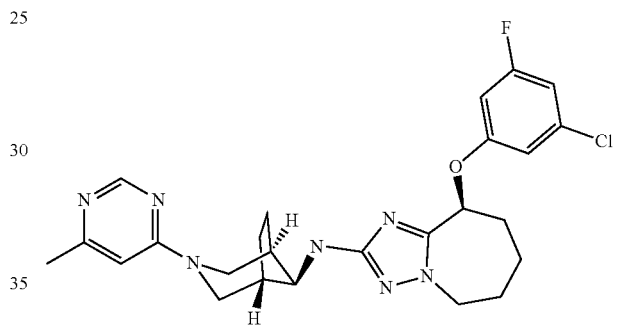

(S)-9-(3-chloro-5-fluorophenoxy)-N-((1R,5S,8s)-3-(6-methylpyrimidin-4-yl)-3-azabicyclo[3.2.1]octan-8-yl)-6,7,8,9-tetrahydro-5H-[1,2,4]triazolo[1,5-a]azepin-2-amine.

* * * * *